US012168673B2

(12) United States Patent
Subramanian et al.

(10) Patent No.: US 12,168,673 B2
(45) Date of Patent: Dec. 17, 2024

(54) PRODRUGS DERIVED FROM NICOTINIC ACID AND RIBOSE

(71) Applicant: Mitopower, Inc., Palo Alto, CA (US)

(72) Inventors: G. Mani Subramanian, Los Altos Hills, CA (US); Gangadhara Ganapati, Palo Alto, CA (US); Manoj Chandrasinhji Desai, Martinez, CA (US); Nikhil Saji Zachariah, Bangalore (IN); Ajay Kumar K S, Bangalore (IN); Gautham Tumkur Pranesh, Bangalore (IN)

(73) Assignee: Mitopower, Inc., Palo Alto, CA (US)

( * ) Notice: Subject to any disclaimer, the term of this patent is extended or adjusted under 35 U.S.C. 154(b) by 103 days.

(21) Appl. No.: 18/177,444

(22) Filed: Mar. 2, 2023

(65) Prior Publication Data

US 2023/0279035 A1 Sep. 7, 2023

Related U.S. Application Data

(60) Provisional application No. 63/315,640, filed on Mar. 2, 2022.

(51) Int. Cl.
*C07H 13/02* (2006.01)
*A61P 13/12* (2006.01)
*C07H 11/04* (2006.01)

(52) U.S. Cl.
CPC .............. *C07H 13/02* (2013.01); *A61P 13/12* (2018.01); *C07H 11/04* (2013.01)

(58) Field of Classification Search
CPC ..... C07H 13/02; C07H 11/04; C07F 9/65515; A61P 13/12
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,710,795 A | 1/1973 | Higuchi et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,891,474 A | 4/1999 | Busetti et al. |
| 5,900,252 A | 5/1999 | Calanchi et al. |
| 5,922,356 A | 7/1999 | Koseki et al. |
| 5,948,433 A | 9/1999 | Burton et al. |
| 5,972,366 A | 10/1999 | Haynes et al. |
| 5,972,891 A | 10/1999 | Kamei et al. |
| 5,980,945 A | 11/1999 | Ruiz |
| 5,983,134 A | 11/1999 | Ostrow |
| 5,985,307 A | 11/1999 | Hanson et al. |
| 5,985,317 A | 11/1999 | Venkateshwaran et al. |
| 5,993,855 A | 11/1999 | Yoshimoto et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |

(Continued)

FOREIGN PATENT DOCUMENTS

| | | |
|---|---|---|
| WO | 2005/025506 A2 | 3/2005 |
| WO | 2008/106227 A1 | 9/2008 |

(Continued)

OTHER PUBLICATIONS

Alberts et al (The Fundamentals of Cancer Prevention, 2nd ed, chapter 10, 2008). (Year: 2008).*
Jarman et al. (J. Chem. Soc. 1969, 6, 918-920). (Year: 1969).*
Garcia-Pèrez et al. Vacuum pyrolysis of sugarcane bagasse (Journal of Analytical and Applied Pyrolysis, 2002, 65, 111-136). (Year : 2002).*
Martin et al. Evaluation of xylose in bagasse by analytical chemistry (Journal of Nature, 1992, 4, 3-9). (Year: 1992).*
Martin et al. Evaluation of xylose in bagasse by analytical chemistry (Journal of Nature, 1992, 4, 3-9). (English translation by Translations Service Center, United States Patent and Trademark Office Aug. 6, 2024 Steven M. Spar (Year: 1992).*
Xie et al. (Biomedicine & Pharmacotherapy, 2018, 99, 715-724). (Year: 2018).*
The Harvard Medical School, Type 1 Diabetes Mellitus, website dated Jan. 13, 2022, acessed online at https://www.health.harvard.edu/ on Aug. 8, 2024 (Year: 2022).*

(Continued)

*Primary Examiner* — Layla D Berry
*Assistant Examiner* — Sarah Grace Scrivener

(57) ABSTRACT

Prodrugs of nicotinic acid which include ribosyl groups are provided. The compounds and pharmaceutical compositions thereof may be used to treat or prevent to treat or prevent a variety of medical disorders, which are characterized by mitochondrial dysfunction such as, for example, metabolic disorders, cardiovascular disorders, cerebrovascular disorders, liver disorders, kidney disorders or muscle disorders.

24 Claims, 18 Drawing Sheets

(56) References Cited

U.S. PATENT DOCUMENTS

| | | | |
|---|---|---|---|
| 6,045,830 | A | 4/2000 | Gari et al. |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,264,970 | B1 | 7/2001 | Hata et al. |
| 6,267,981 | B1 | 7/2001 | Okamoto et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Tgari et al. |
| 6,419,961 | B1 | 7/2002 | Gari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 11,286,274 | B2 * | 3/2022 | Ganapati ............ C07H 19/048 |

FOREIGN PATENT DOCUMENTS

| | | | |
|---|---|---|---|
| WO | 2018/033639 A1 | 2/2018 | |
| WO | WO-2018236814 A2 * | 12/2018 | ........... A61K 31/706 |
| WO | 2020/131578 A2 | 6/2020 | |

OTHER PUBLICATIONS

Biron et al. (Scientific reports, 2013, 3, 1354). (Year: 2013).*
Definition of prevent, Oxford English Dictionary Online, http://dictionary.oed.com/, accessed online Mar. 27, 2010, especially definition 9a. at p. 2. (Year: 2010).*
Guillory, K., Chapter 5, pp. 202-205 in Polymorphism in Pharmaceutical Solids, (Brittain, H. ed.), Marcel Dekker, Inc., New York, NY, 1999Guillory, K., Chapter 5, pp. 202-205 in Polymorphism in Pharmaceutical Solids, (Brittain, H. ed.), Marcel Dekker, Inc., New York, NY, 1999).
Brittain, H., Chapter 6, pp. 205-208 in Polymorphism in Pharmaceutical Solids, (Brittain, H. ed.), Marcel Dekker, Inc. New York, 1999.
Holodiag, Pharmaparc II, Voie de l'Innovation, 27 100 Val de Reuil, France; accessed Jun. 29, 2023 http://www.holodiag.comHOLODIAG, Pharmaparc II, Voie de l'Innovation, 27 100 Val de Reuil, France (http://www.holodiag.com).
Jens T. Carstensen, Drug Stability: Principles & Practice, 2d. Ed., Marcel Dekker, NY, NY, 1995, pp. 379-380.
Sefton, CRC Crit. Ref. Biomed. Eng. 14:201 (1987.
Saudek CD, Selam JL, Pitt HA, Waxman K, Rubio M, Jeandidier N, Turner D, Fischell RE, Charles MA. A preliminary trial of the programmable implantable medication system for insulin delivery. N Engl J Med. Aug. 31, 1989;321(9):574-9.
Langer, Robert. "New methods of drug delivery." Science 249.4976 (1990): 1527-1533.
Haffner, Curt D., et al. "Discovery, synthesis, and biological evaluation of thiazoloquin (az) olin (on) es as potent CD38 inhibitors." Journal of medicinal chemistry 58.8 (2015): 3548-3571.
Pocai A, Carrington PE, Adams JR, Wright M, Eiermann G, Zhu L, Du X, Petrov A, Lassman ME, Jiang G, Liu F, Miller C, Tota LM, Zhou G, Zhang X, Sountis MM, Santoprete A, Capito' E, Chicchi GG, Thornberry N, Bianchi E, Pessi A, Marsh DJ, SinhaRoy R. Glucagon-like peptide 1/glucagon receptor dual agonism reverses obesity in mice. Diabetes. Oct. 2009;58(10):2258-66. doi: 10.2337/db09-0278. Epub Jul. 14, 2009. PMID: 19602537; PMCID: PMC2750209.
Muppidi, Avinash, et al. "Design of potent and proteolytically stable oxyntomodulin analogs." ACS chemical biology 11.2 (2016): 324-328.
Scott, R., et al. "Oxyntomodulin analogue increases energy expenditure via the glucagon receptor." Peptides 104 (2018): 70-77.
(Deyrup, Met al.) Improved delivery through biological membranes. Synthesis and antiviral activity of a series of ribavirin chemical delivery systems: 2' and 3' derivatives. Antiviral Chemistry and Chemotherapy, vol. 2, No. 6, 1991, pp. 337-355.
(Bhagrath, Met al.) Improved delivery through biological membranes. Synthesis, characterization and antiviral activity of a series of ribavirin chemical delivery systems: 5' and carboxamide derivatives. Antiviral Chemistry and Chemotherapy, vol. 2, No. 5, 1991, pp. 265-286.

* cited by examiner

PRODRUGS DERIVED FROM NICOTINIC ACID AND RIBOSE

CROSS-REFERENCE TO RELATED APPLICATIONS

This application claims the benefit under 35 U.S.C. § 119(e) of U.S. Provisional Application No. 63/315,640, filed Mar. 2, 2022, which is hereby incorporated by reference in its entirety.

FIELD

Disclosed are novel prodrugs of nicotinic acid which include ribosyl groups and pharmaceutical compositions thereof which may be used to treat or prevent a variety of medical disorders, which may be characterized by mitochondrial dysfunction. The compounds and pharmaceutical compositions thereof may be used to treat or prevent metabolic disorders, cardiovascular disorders, cerebrovascular disorders, liver disorders, kidney disorders or muscle disorders.

BACKGROUND

Mitochondrial dysfunction is a hallmark of chronic and acute inflammatory and metabolic conditions, and often associated with NAD+ depletion. There are 3 established NAD+ synthesis pathways: salvage pathway utilizes nicotinamide, de novo synthesis utilizes tryptophan, and the Preiss Handler pathway utilized nicotinic acid. The Preiss Handler pathway is particularly relevant in metabolically active organs including liver, kidney, brain, and skeletal muscle. In addition, nicotinic acid directly modulates key metabolic enzymes involved in lipid metabolism.

Nicotinic acid or niacin have been used to treat hypertriglyceridemia and more recently mitochondrial myopathy. The benefits are based on the unique mechanism of direct modulation of several key metabolic enzymes and broad benefits of enhancing NAD+ levels in key vital organs. However, nicotinic acid is associated with dose limiting adverse events of flushing that limits its use. Flushing is mediated by the interaction of nicotinic acid with GPR109A receptor. Furthermore, nicotinic acid is rapidly cleared with poor penetration and/or retention in vital organs. This necessitates substantial dosing to achieve efficacy; dose escalation of nicotinic acid is poorly tolerated by the majority of patients.

There is a major unmet need for a novel approach to improve bioavailability and to significantly enhance intracellular concentrations of nicotinic acid to maximize the pharmacology of nicotinic acid. This is currently not possible with nicotinic acid. Maintaining sustained levels of nicotinic acid in key vital organs like the kidney, liver, and muscle will provides higher efficacy in diseases associated with severe organ damage.

SUMMARY

These and other needs are provided herein as the disclosed may uniquely reverse the mitochondrial and metabolic dysfunction in vital organs. In one aspect, a compound of structural Formula (I):

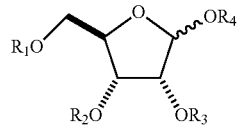

or pharmaceutically acceptable salts, hydrates or solvates thereof is provided where $R_1$ is —H, $R_8C(O)$—,

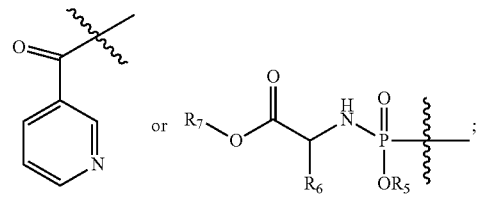

$R_2$ is —H or $R_9C(O)$—; $R_3$ is —H or $R_{10}C(O)$—; $R_4$ is —H, alkyl, substituted alkyl, alkenyl, substituted alkenyl, aryl, substituted aryl, arylalkyl, substituted arylalkyl, heteroaryl, substituted heteroaryl, heteroarylalkyl, substituted heteroarylalkyl, $R_{11}C(O)$— or

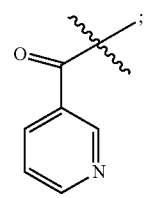 [SMILES: *C(=O)c1cccnc1]

$R_6$ is —H, alkyl, substituted alkyl, alkenyl, substituted alkenyl, aryl, substituted aryl, arylalkyl, substituted arylalkyl, heteroaryl, substituted heteroaryl, heteroarylalkyl or substituted heteroarylalkyl; and $R_5$, $R_7$, $R_8$, $R_9$, $R_{10}$ and $R_{11}$ are independently alkyl, substituted alkyl, alkenyl, substituted alkenyl, aryl, substituted aryl, arylalkyl, substituted arylalkyl, heteroaryl, substituted heteroaryl, heteroarylalkyl or substituted heteroarylalkyl; provided that at least one of $R_1$ or $R_4$ is

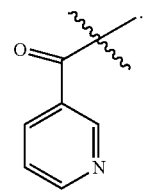

The compounds of structural Formula (I) may provide more efficient delivery and subsequent conversion to NAD+ with the potential for greater efficacy and safety compared to nicotinic acid.

Also provided are derivatives, including salts, esters, enol ethers, enol esters, solvates, hydrates, metabolites and prodrugs of the compounds described herein. Further provided are pharmaceutical compositions which include the compounds provided herein and a pharmaceutically acceptable vehicle.

In still another aspect, methods of treating, preventing, or ameliorating symptoms of medical disorders such as, for example metabolic disorders, cardiovascular disorders, cerebrovascular disorders, liver disorders, a kidney disorders or muscle disorders.

DETAILED DESCRIPTION

Definitions

Figure 1:
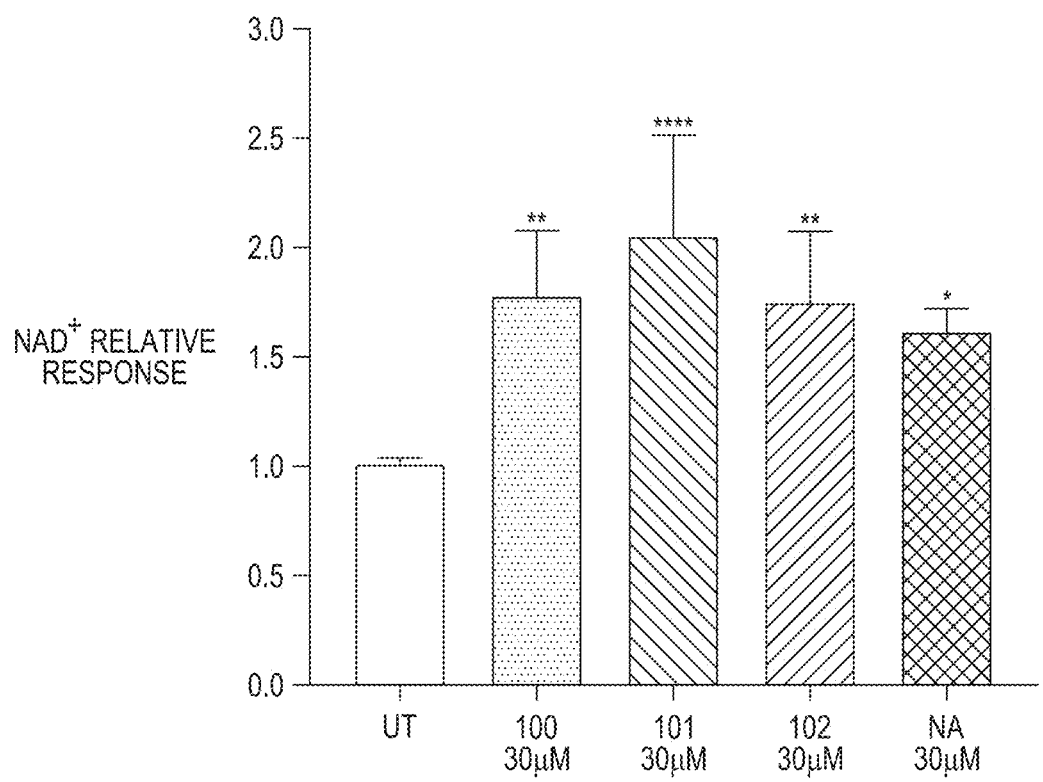
FIG. 1 depicts NAD+ increase in Jurkat cells in RPMI media supplemented with 30 μM of compounds 100, 101 and 102.

Unless defined otherwise, all technical and scientific terms used herein have the same meaning as is commonly understood by one of ordinary skill in the art to which this invention belongs. If a plurality of definitions for a term exist herein, those in this section prevail unless stated otherwise. Unless defined otherwise, all technical and scientific terms used herein have the same meaning as is commonly understood by one of ordinary skill in the art to which this invention belongs. If a plurality of definitions for a term exist herein, those in this section prevail unless stated otherwise. Unless defined otherwise, all technical and scientific terms used herein have the same meaning as is commonly understood by one of ordinary skill in the art to which this invention belongs. If a plurality of definitions for a term exist herein, those in this section prevail unless stated otherwise.

As used herein, and unless otherwise specified, the terms "about" and "approximately," when used in connection with a property with a numeric value or range of values indicate that the value or range of values may deviate to an extent deemed reasonable to one of ordinary skill in the art while still describing the particular property. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. It should be understood that u to v carbons includes u+1 to v, u+2 to v, u+3+v, etc. carbons, u+1 to u+3 to v, u+1 to u+4 to v, u+2 to u+4 to v, etc. and cover all possible permutation of u and v.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane. Typical alkyl groups include, but are not limited to, methyl; ethyl; propyls such as propan-1-yl, propan-2-yl, etc.; butyls such as butan-1-yl, butan-2-yl, 2-methyl-propan-1-yl, 2-methyl-propan-2-yl, etc.; and the like. In some aspects, an alkyl group comprises from 1 to 20 carbon atoms ($C_1$-$C_{20}$ alkyl). In other aspects, an alkyl group comprises from 1 to 10 carbon atoms ($C_1$-$C_{10}$ alkyl). In still other aspects, an alkyl group comprises from 1 to 6 carbon atoms ($C_1$-$C_6$ alkyl).

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some aspects, an alkenyl group comprises from 1 to 20 carbon atoms ($C_1$-$C_{20}$ alkenyl). In other aspects, an alkenyl group comprises from 1 to 10 carbon atoms ($C_1$-$C_{10}$ alkenyl). In still other aspects, an alkenyl group comprises from 1 to 6 carbon atoms ($C_1$-$C_6$ alkenyl).

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some aspects, an alkynyl group comprises from 1 to 20 carbon atoms ($C_1$-$C_{20}$ alkynyl). In other aspects, an alkynyl group comprises from 1 to 10 carbon atoms ($C_1$-$C_{10}$ alkynyl). In still other aspects, an alkynyl group comprises from 1 to 6 carbon atoms ($C_1$-$C_6$ alkynyl).

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some aspects, an aryl group comprises from 6 to 20 carbon atoms ($C_6$-$C_{20}$ aryl). In other aspects, an aryl group comprises from 6 to 15 carbon atoms ($C_6$-$C_{15}$ aryl). In still other aspects, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In some aspects, an arylalkyl group is ($C_6$-$C_{30}$) arylalkyl, e.g., the alkyl moiety of the arylalkyl group is ($C_1$-$C_{10}$) alkyl and the aryl moiety is ($C_6$-$C_{20}$) aryl. In other aspects, an arylalkyl group is ($C_6$-$C_{20}$) arylalkyl, e.g., the alkyl moiety of the arylalkyl group is ($C_1$-$C_8$) alkyl and the aryl moiety is ($C_6$-$C_{12}$) aryl. In still other aspects, an arylalkyl group is ($C_6$-$C_{15}$) arylalkyl, e.g., the alkyl moiety of the arylalkyl group is ($C_1$-$C_5$) alkyl and the aryl moiety is ($C_6$-$C_{10}$) aryl.

"Arylalkenyl," by itself or as part of another substituent, refers to an acyclic alkenyl group in which one of the hydrogen atoms bonded to a carbon atom, is replaced with an aryl group as, as defined herein. In some aspects, an arylalkenyl group is ($C_6$-$C_{30}$) arylalkenyl, e.g., the alkenyl moiety of the arylalkenyl group is ($C_1$-$C_{10}$) alkenyl and the aryl moiety is ($C_6$-$C_{20}$) aryl. In other aspects, an arylalkenyl group is ($C_6$-$C_{20}$) arylalkenyl, e.g., the alkenyl moiety of the arylalkenyl group is ($C_1$-$C_8$) alkenyl and the aryl moiety is ($C_6$-$C_{12}$) aryl. In still other aspects, an arylalkenyl group is ($C_6$-$C_{15}$) arylalkenyl, e.g., the alkenyl moiety of the arylalkenyl group is ($C_1$-$C_5$) alkenyl and the aryl moiety is ($C_6$-$C_{10}$) aryl.

"Arylalkynyl," by itself or as part of another substituent, refers to an acyclic alkynyl group in which one of the hydrogen atoms bonded to a carbon atom, is replaced with an aryl group as, as defined herein. In some aspects, an arylalkynyl group is ($C_6$-$C_{30}$) arylalkynyl, e.g., the alkynyl moiety of the arylalkynyl group is ($C_1$-$C_{10}$) alkynyl and the aryl moiety is ($C_6$-$C_{20}$) aryl. In other aspects, an arylalkynyl group is ($C_6$-$C_{20}$) arylalkynyl, e.g., the alkynyl moiety of the arylalkenyl group is ($C_1$-$C_8$) alkynyl and the aryl moiety is ($C_6$-$C_{12}$) aryl. In still other aspects, an arylalkynyl group is ($C_6$-$C_{15}$) arylalkynyl, e.g., the alkynyl moiety of the arylalkynyl group is ($C_1$-$C_5$) alkynyl and the aryl moiety is ($C_6$-$C_{10}$) aryl.

"Cycloalkyl," by itself or as part of another substituent, refers to a saturated cyclic monovalent hydrocarbon radical derived by the removal of one hydrogen atom from a single carbon atom of a parent cycloalkane. Typical cycloalkyl groups include, but are not limited to, cyclopropyl, cyclobutyl, cyclopentyl cyopentenyl; etc.; and the like. In some aspects, a cycloalkyl group comprises from 3 to 20 carbon atoms ($C_1$-$C_{15}$ cycloalkyl). In other aspects, a cycloalkyl group comprises from 3 to 10 carbon atoms ($C_1$-$C_{10}$ cycloalkyl). In still other aspects, a cycloalkyl group comprises from 3 to 8 carbon atoms ($C_1$-$C_8$ cycloalkyl). The term "cyclic monovalent hydrocarbon radical" also includes multicyclic hydrocarbon ring systems having a single radical and between 3 and 12 carbon atoms. Exemplary multicyclic cycloalkyl rings include, for example, norbornyl, pinyl, and adamantyl.

"Cycloalkenyl," by itself or as part of another substituent, refers to an unsaturated cyclic monovalent hydrocarbon radical derived by the removal of one hydrogen atom from a single carbon atom of a parent cycloalkene. Typical cycloalkenyl groups include, but are not limited to, cyclopropene, cyclobutene cyclopentene; etc.; and the like. In some aspects, a cycloalkenyl group comprises from 3 to 20 carbon atoms ($C_1$-$C_{20}$ cycloalkenyl). In other aspects, a cycloalkenyl group comprises from 3 to 10 carbon atoms ($C_1$-$C_{10}$ cycloalkenyl). In still other aspects, a cycloalkenyl group comprises from 3 to 8 carbon atoms ($C_1$-$C_8$ cycloalkenyl). The term 'cyclic monovalent hydrocarbon radical" also includes multicyclic hydrocarbon ring systems having a single radical and between 3 and 12 carbon atoms.

"Cycloheteroalkyl," by itself or as part of another substituent, refers to a cycloalkyl group as defined herein in which one or more one or more of the carbon atoms (and optionally any associated hydrogen atoms), are each, independently of one another, replaced with the same or different heteroatoms or heteroatomic groups as defined in "heteroalkyl" below. In some aspects, a cycloheteroalkyl group comprises from 3 to 20 carbon and hetero atoms (1-20 cycloheteroalkyl). In other aspects, a cycloheteroalkyl group comprises from 3 to 10 carbon and hetero atoms ($_{1-10}$ cycloheteroalkyl). In still other aspects, a cycloheteroalkyl group comprises from 3 to 8 carbon and hetero atoms (1.8 cycloheteroalkyl). The term "cyclic monovalent heteroalkyl radical" also includes multicyclic heteroalkyl ring systems having a single radical and between 3 and 12 carbon and at least one hetero atom.

"Cycloheteroalkenyl," by itself or as part of another substituent, refers to a cycloalkenyl group as defined herein in which one or more one or more of the carbon atoms (and optionally any associated hydrogen atoms), are each, independently of one another, replaced with the same or different heteroatoms or heteroatomic groups as defined in "heteroalkenyl" below. In some aspects, a cycloheteroalkenyl group comprises from 3 to 20 carbon and hetero atoms (1-20 cycloheteroalkenyl). In other aspects, a cycloheteroalkenyl group comprises from 3 to 10 carbon and hetero atoms (1.10) cycloheteroalkenyl). In still other aspects, a cycloheteroalkenyl group comprises from 3 to 8 carbon and heteroatoms (1.8 cycloheteroalkenyl). The term "cyclic monovalent heteroalkenyl radical" also includes multicyclic heteroalkenyl ring systems having a single radical and between 3 and 12 carbon and at least one hetero atoms.

"Compounds," refers to compounds encompassed by structural formulae disclosed herein and includes any specific compounds within these formulae whose structure is disclosed herein. Compounds may be identified either by their chemical structure and/or chemical name. The chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass the stereoisomerically pure form depicted in the structure (e.g., geometrically pure, enantiomerically pure or diastereomerically pure). The chemical structures depicted herein also encompass the enantiomeric and stereoisomeric derivatives of the compound depicted. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Halo," by itself or as part of another substituent refers to a radical—F, —Cl, —Br or —I.

"Heteroalkyl," refer to an alkyl, group, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$ =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl. In some aspects, an heteroalkyl group comprises from 1 to 20 carbon and hetero atoms (1-20 heteroalkyl). In other aspects, an heteroalkyl group comprises from 1 to 10 carbon and hetero atoms ($_{1-10}$ heteroalkyl). In still other aspects, an heteroalkyl group comprises from 1 to 6 carbon and hetero atoms ($_{1-6}$ heteroalkyl).

"Heteroalkenyl," refers to an alkenyl group in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$ =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl. In some aspects, an heteroalkenyl group comprises from 1 to 20 carbon and hetero atoms ($_{1-20}$ heteroalkenyl). In other aspects, an heteroalkenyl group comprises from 1 to 10 carbon and hetero atoms ($_{1-10}$ heteroalkenyl). In still other aspects, an heteroalkenyl group comprises from 1 to 6 carbon and hetero atoms ($_{1-6}$ heteroalkenyl).

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some aspects, the heteroaryl group comprises from 5 to 20 ring atoms (5-20 membered heteroaryl). In other aspects, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl," by itself or as part of another substituent refers to an acyclic alkyl group in which one of the hydrogen atoms bonded to a carbon atom, typically a terminal or sp$^3$ carbon atom, is replaced with a heteroaryl group. In some aspects, the heteroarylalkyl group is a 6-21 membered heteroarylalkyl, e.g., the alkyl moiety of the heteroarylalkyl is ($C_1$-$C_6$) alkyl and the heteroaryl moiety is a 5-15-membered heteroaryl. In other aspects, the heteroarylalkyl is a 6-13 membered heteroarylalkyl, e.g., the alkyl moiety is ($C_1$-$C_3$) alkyl and the heteroaryl moiety is a 5-10 membered heteroaryl.

"Heteroarylalkenyl," by itself or as part of another substituent refers to an acyclic alkenyl group in which one of the hydrogen atoms bonded to a carbon atom, is replaced with a heteroaryl group. In some aspects, the heteroarylalkenyl group is a 6-21 membered heteroarylalkyl, e.g., the alkenyl moiety of the heteroarylalkenyl is ($C_1$-$C_6$) alkenyl and the heteroaryl moiety is a 5-15-membered heteroaryl. In other aspects, the heteroarylalkenyl is a 6-13 membered heteroarylalkenyl, e.g., the alkenyl moiety is ($C_1$-$C_3$) alkyl and the heteroaryl moiety is a 5-10 membered heteroaryl.

"Heteroarylalkynyl," by itself or as part of another substituent refers to an acyclic alkenyl group in which one of the hydrogen atoms bonded to a carbon atom, is replaced with a heteroaryl group. In some aspects, the heteroarylalkynyl group is a 6-21 membered heteroarylalkyl, e.g., the alkynyl moiety of the heteroarylalkynyl is ($C_1$-$C_6$) alkynyl and the heteroaryl moiety is a 5-15-membered heteroaryl. In other aspects, the heteroarylalkynyl is a 6-13 membered heteroarylalkynyl, e.g., the alkynyl moiety is ($C_1$-$C_3$) alkyl and the heteroaryl moiety is a 5-10 membered heteroaryl.

"Hydrates," refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202-205 in *Polymorphism in Pharmaceutical Solids*, (Brittain, H. ed.), Marcel Dekker, Inc., New York, NY, 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routinely offer services that include preparation and/or characterization of hydrates such as, for example, HOLODIAG, Pharmaparc II, Voie de l'Innovation, 27 100 Val de Reuil, France (http://www.holodiag.com).

"Parent Aromatic Ring System," refers to an unsaturated cyclic or polycyclic ring system having a conjugated p electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System," refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, b-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt," refers to a salt of a compound which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4- hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Preventing," or "prevention," refers to a reduction in risk of acquiring a disease or disorder (i.e., causing at least one of the clinical symptoms of the disease not to develop in a patient that may be exposed to or predisposed to the disease but does not yet experience or display symptoms of the disease). The application of a therapeutic for preventing or prevention of a disease or disorder is known as 'prophylaxis.' In some aspects, the compounds provided herein provide superior prophylaxis because of lower long term side effects over long time periods.

"Prodrug" as used herein, refers to a derivative of a drug molecule that requires a transformation within the body to release the active drug. Prodrugs are frequently, although not necessarily, pharmacologically inactive until converted to the parent drug.

"Promoiety" as used herein, refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group," refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Spirocycloheteroalkyl," by itself or as part of another substituent refers to a double ring alkyl structure which shares one atom and which comprise at least one hetero atom independently selected from the group consisting of N, O, and S in the ring.

"Solvates," refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 202-205 in *Polymorphism in Pharmaceutical Solids*, (Brittain, H. ed.), Marcel Dekker, Inc., New York, NY, 1999)). The above methods for preparing solvates are well within the ambit of those of skill in the art, are completely conventional and do not require any experimentation beyond what is typical in the art. Solvates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include $R^a$, halo, —O, =O, —$OR^b$, —$SR^b$, —S=S, —$NR^cR^c$, —$NR^b$, =N—$OR^b$, trihalomethyl, —$CF_3$, —CN, —OCN, —SCN, —NO, —$NO_2$, —N—$OR^b$, —N—$NR^cR^c$, —$NR^cS(O)_2R^b$ =$N_2$, —$N_3$, —$S(O)_2R^b$, —$S(O)_2NR^bR^b$, —$S(O)_2O$—, —$S(O)_2OR$, —$OS(O)_2R^b$, —$OS(O)_2O$—, —$OS(O)_2OR$, —$OS(O)_2NR^cNR^c$, —$P(O)(O$—$)_2$, —$P(O)(OR^b)(O)$, —$P(O)(OR^b)(OR^b)$, —$C(O)R^b$, —$C(O)NR$—$OR^b$—$C(S)$ $R^b$, —$C(NR^b)R^b$, —$C(O)O$—, —$C(O)OR$, —$C(S)OR$, —$C(O)NR^cR^c$, —$C(NR^b)NR^cR^c$, —$OC(O)R^b$, —$OC(S) R^b$, —$OC(O)O$—, —$OC(O)OR$, —$OC(O)NR^cR^c$, —$OC(NCN)$ $NR^cR^c$, —$OC(S)OR^b$, —$NR^bC(O)R^b$, —$NR^cC(S)R^b$, —$NR^bC(O)O$—, —$NR^bC(O)OR$, —$NR^bC(NCN)OR$, —$NR^bS(O)_2NR^cR^c$, —$NR^bC(S)OR$, —$NR^bC(O)NR^cR^c$, —$NR^bC(S)NR^cR^c$, —$NR^bC(S)NR^bC(O)R^a$, —$NR^bS(O)_2OR$, —$NR^bS(O)_2R^b$, —$NR^bC(NCN)$ $NR^cR^c$, —$NR^bC(NR^b)R^b$ and —$NR^bC(NR^b)NR^cR^c$, where each $R^a$ is independently, aryl, substituted aryl, heteroalkyl, substituted heteroalkyl, heteroaryl or substituted heteroaryl; each $R^b$ is independently hydrogen, alkyl, heteroalkyl, substituted heteroalkyl, arylalkyl, substituted arylalkyl, heteroarylalkyl or substituted heteroarylalkyl; and each $R^c$ is independently $R^b$ or alternatively, the two $R^c$s taken together with the nitrogen atom to which they are bonded form a 4-, 5-, 6- or 7 membered-cycloheteroalkyl, substituted cycloheteroalkyl or a cycloheteroalkyl fused with an aryl group which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. In other aspects, substituent groups useful for substituting saturated carbon atoms in the specified group or radical include $R^a$, halo, —$OR^b$, —$NR^cR^c$, trihalomethyl, —CN, —$NR^bS(O)_2R^b$, —$C(O)R^b$, —$C(O)NR$—$OR^b$, —$C(O)OR$, —$C(O)NR^cR^c$, —$OC(O)R^b$, —$OC(O)OR$, —$OS(O)_2NR^cNR^c$, —$OC(O)NR^cR^c$, and —$NR^bC(O)OR$, where each $R^a$ is independently alkyl, aryl, heteroaryl, each $R^b$ is independently hydrogen, $R^a$, heteroalkyl, arylalkyl, heteroarylalkyl; and each $R^c$ is independently $R^b$ or alternatively, the two $R^c$s taken together with the nitrogen atom to which they are bonded form a 4-, 5-, 6 or −7 membered-cycloheteroalkyl ring. In still other aspects, substituent groups useful for substituting saturated carbon atoms in the specified group or radical include $R^a$, halo, —$OR^b$, —$NR^cR^c$, trihalomethyl, —CN, —C(O)$R^b$, —C(O)OR, —C(O)$NR^cR^c$, —OC(O)$R^b$, —OC(O)$NR^cR^c$, and —$NR^c$C(O)OR, where each $R^a$ is independently alkyl, aryl, heteroaryl, each $R^b$ is independently hydrogen, $R^a$, heteroalkyl, arylalkyl, heteroarylalkyl; and each R is independently $R^b$ or alternatively, the two $R^c$s taken together with the nitrogen atom to which they are bonded form a 4-, 5-, 6 or −7 membered-cycloheteroalkyl ring.

Substituent groups useful for substituting unsaturated carbon atoms in the specified group or radical include —$R^a$, halo, —O, —$OR^b$, —$SR^b$, —S—, —$NR^cR^c$, trihalomethyl, —$CF_3$, —CN, —OCN, —SCN, —NO, —$NO_2$, —$N_3$, —S(O)$_2$O, —S(O)$_2$OR, —OS(O)$_2R^b$, —OS(O)$_2$OR, —OS(O)$_2$O—, —P(O)(O—)$_2$, —P(O)($OR^b$)(O), —P(O)($OR^b$)($OR^b$), —C(O)$R^b$, —C(S)$R^b$, —C(NR$^b$) $R^b$, —C(O)O—, —C(O)OR, —C(S)OR, —C(O)$NR^cR^c$, —C($NR^b$)$NR^cR^c$, —OC(O)$R^b$, —OC(S)$R^b$, —OC(O) O—, —OC(O)OR, —OC(S)OR, —OC(O)$NR^cR^c$, —OS(O)$_2NR^cNR^c$, —$NR^b$C(O)$R^b$, —$NR^b$C(S)$R^b$, —$NR^b$C(O)O—, —$NR^b$C(O)OR, —$NR^b$S(O)$_2$OR$^a$, —$NR^b$S(O)$_2R^a$, —$NR^b$C(S)$OR^b$, —$NR^b$C(O)$NR^cR^c$, —$NR^c$C(NR)$R^b$—$NR^b$C($NR^b$)$NR^cR^c$ and —C(NR)$NR^b$C(NR)$NR^cR^c$ where $R^a$, $R^b$ and R are as previously defined. In other aspects, substituent groups useful for substituting unsaturated carbon atoms in the specified group or radical include —$R^a$, halo, —$OR^b$, —$SR^b$, —$NR^cR^c$, trihalomethyl, —CN, —S(O)$_2$OR, —C(O)$R^b$, —C(O)OR, —C(O)$NR^cR^c$, —OC(O)$R^b$, —OC(O)OR, —OS(O)$_2NR^cR^c$, —$NR^b$C(O)$R^b$ and —$NR^b$C(O)OR, where $R^a$, $R^b$ and R are as previously defined. In still other aspects, substituent groups useful for substituting unsaturated carbon atoms in the specified group or radical include —$R^a$, halo, —$OR^b$, —$NR^cR^c$, trihalomethyl, —S(O)$_2$OR, —C(O)$R^b$, —C(O)OR, —C(O)$NR^cR^c$, —OC(O)$R^b$, —$NR^b$C(O)$R^b$ and —$NR^b$C(O)OR, where $R^a$, $R^b$ and R are as previously defined.

Substituent groups useful for substituting nitrogen atoms in heteroalkyl and cycloheteroalkyl groups include, but are not limited to, —$R^a$, —O, —$OR^b$, —$SR^b$, —S—, —$NR^cR^c$, trihalomethyl, —$CF_3$, —CN, —NO, —$NO_2$, —S(O)$_2R^b$, —S(O)$_2$O—, —S(O)$_2$OR, —OS(O)$_2R^b$, —OS(O)$_2$O, —OS(O)$_2OR^b$, —P(O)(O—)$_2$, —P(O)($OR^b$)(O), —P(O)($OR^b$)($OR^b$), —C(O)$R^b$, —C(S)$R^b$, —C(NR)$R^b$, —C(O)$OR^b$, —C(S)OR, —C(O)$NR^cR^c$, —C($NR^b$)$NR^cR^c$, —OC(O)$R^b$, —OC(S)$R^b$, —OC(O)OR, —OC(S)OR, —$NR^b$C(O)$R^b$, —$NR^b$C(S)$R^b$, —$NR^b$C(O)OR, —$NR^b$C(S)OR, —$NR^c$C(O)$NR^cR^c$, —$NR^b$C($NR^b$)$R^b$, —$NR^b$C($NR^b$)$NR^cR^c$ and —C($NR^b$)$NR^b$C($NR^b$)$NR^cR^c$ where $R^a$, $R^b$ and R are as previously defined. In some aspects, substituent groups useful for substituting nitrogen atoms in heteroalkyl and cycloheteroalkyl groups include, $R^a$, halo, —$OR^b$, —$NR^cR^c$, trihalomethyl, —CN, —S(O)$_2OR^b$, —OS(O)$_2R^b$, —C(O)$R^b$, —C(NR)$R^b$, —C(O)OR, —C(O)$NR^cR^c$, —OC(O)$R^b$, —OC(O)OR, —OS(O)$_2NR^cNR$, —$NR^b$C(O)$R^b$ and —$NR^b$C(O)OR, where $R^a$, $R^b$ and $R^c$ are as previously defined. In still other aspects, substituent groups useful for substituting nitrogen atoms in heteroalkyl and cycloheteroalkyl groups include, $R^a$, halo, —$OR^b$, —$NR^cR^c$, trihalomethyl, —CN, —S(O)$_2OR^b$, —C(O)$R^b$, —C(NR$^b$)$R^b$, —C(O)OR, —C(O)$NR^cR^c$, —OC(O)$R^b$, —$NR^b$C(O)$R^b$ and —$NR^b$C(O)OR, where $R^a$, $R^b$ and R are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Subject," "individual," or "patient," is used interchangeably herein and refers to a vertebrate, preferably a mammal. Mammals include, but are not limited to, murines, rodents, simians, humans, farm animals, sport animals and pets. In some aspects, the subject, individual, or patient is a member of the species *Homo sapiens*. In other aspects, the subject, individual, or patient includes all mammals except *Homo sapiens*.

"Treating," or "treatment," of any disease or disorder refers, in some aspects, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for long-term side effects over multiple years. In other aspects "treating" or "treatment" refers to ameliorating at least one physical parameter, which may not be discernible by the patient. In yet other aspects, "treating" or "treatment" refers to inhibiting the disease or disorder, either physically (e.g., stabilization of a discernible symptom), physiologically (e.g., stabilization of a physical parameter) or both. In yet other aspects, "treating" or "treatment" refers to delaying the onset of the disease or disorder.

"Therapeutically effective amount," means the amount of a compound that, when administered to a patient for treating a disease, is sufficient to treat the disease. The "therapeutically effective amount" will vary depending on the compound, the disease and its severity and the age, weight, adsorption, distribution, metabolism and excretion etc., of the patient to be treated.

"Vehicle," refers to a diluent, excipient or carrier with which a compound is administered to a subject. In some aspects, the vehicle is pharmaceutically acceptable.

Compounds

Provided herein is a compound of Formula (I):

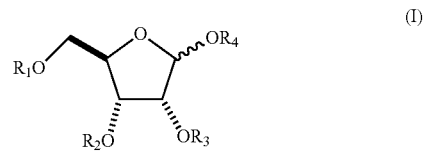

or pharmaceutically acceptable salts, hydrates or solvates thereof where; $R_1$ is —H, $R_8$C(O)—, or

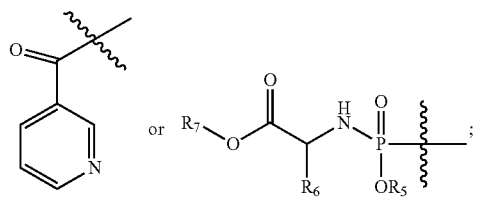;

$R_2$ is —H or $R_9C(O)$—; $R_3$ is —H or $R_{10}C(O)$—; $R_4$ is —H, alkyl, substituted alkyl, alkenyl, substituted alkenyl, aryl, substituted aryl, arylalkyl, substituted arylalkyl, heteroaryl, substituted heteroaryl, heteroarylalkyl, substituted heteroarylalkyl, $R_{11}C(O)$— or

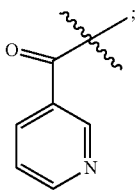

$R_6$ is —H, alkyl, substituted alkyl, alkenyl, substituted alkenyl, aryl, substituted aryl, arylalkyl, substituted arylalkyl, heteroaryl, substituted heteroaryl, heteroarylalkyl or substituted heteroarylalkyl; and $R_5$, $R_7$, $R_8$, $R_9$, $R_{10}$ and $R_{11}$ are independently alkyl, substituted alkyl, alkenyl, substituted alkenyl, aryl, substituted aryl, arylalkyl, substituted arylalkyl, heteroaryl, substituted heteroaryl, heteroarylalkyl or substituted heteroarylalkyl; provided that at least one of $R_1$ or $R_4$ is

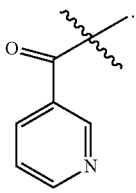 [SMILES: *C(=O)c1cccnc1]

In some embodiments, $R_4$ is —H, alkyl, substituted alkyl, alkenyl, substituted alkenyl, aryl, arylalkyl, heteroaryl, heteroarylalkyl, $R_{11}C(O)$—, or

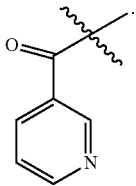 [SMILES: *C(=O)c1cccnc1]

In other embodiments, $R_4$ is —H, alkyl, substituted alkyl, alkenyl, substituted alkenyl, $R_{11}C(O)$— or

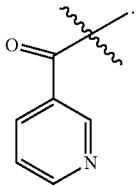 [SMILES: *C(=O)c1cccnc1]

In still other embodiments, $R_4$ is alkyl, alkenyl, $R_{11}C(O)$— or

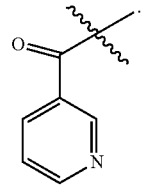 [SMILES: *C(=O)c1cccnc1]

In some embodiments, $R_8$, $R_9$, $R_{10}$ and Rn are independently alkyl, substituted alkyl, alkenyl, substituted alkenyl, aryl, arylalkyl, heteroaryl, or heteroarylalkyl. In other embodiments, $R_8$ and $R_{11}$ are alkyl, substituted alkyl, alkenyl, substituted alkenyl or heteroaryl and $R_9$ and $R_{10}$ are independently alkyl, substituted alkyl, alkenyl or substituted alkenyl. In still other embodiments, $R_8$ and $R_{11}$ are alkyl, substituted alkyl, alkenyl, substituted alkenyl or heteroaryl and $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$. In still other embodiments, $R_8$ and $R_{11}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$ or heteroaryl and $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$. In still other embodiments, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_1$ is

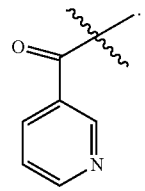 [SMILES: *C(=O)c1cccnc1]

In some embodiments, $R_5$ is alkyl, alkenyl, aryl, substituted aryl, arylalkyl, heteroaryl, or heteroarylalkyl. In other embodiments, $R_5$ is alkyl, alkenyl, aryl or substituted aryl. In still other embodiments, $R_5$ is aryl.

In some embodiments, $R_6$ is —H, alkyl, substituted alkyl, alkenyl, substituted alkenyl, aryl, arylalkyl, heteroaryl or heteroarylalkyl. In other embodiments, $R_6$ is —H, alkyl, substituted alkyl, arylalkyl or heteroarylalkyl.

In some embodiments, $R_7$ is alkyl, alkenyl, aryl, substituted aryl, arylalkyl, heteroaryl, or heteroarylalkyl. In other embodiments, $R_7$ is alkyl, alkenyl or arylalkyl.

In some embodiments, $R_5$ is alkyl, alkenyl, aryl or substituted aryl, $R_6$ is alkyl, substituted alkyl, arylalkyl or heteroarylalkyl and $R_7$ is alkyl, alkenyl or arylalkyl. In other embodiments, $R_5$ is aryl or arylalkyl, $R_6$ is alkyl, substituted alkyl, arylalkyl or heteroarylalkyl and $R_7$ is alkyl, alkenyl or arylalkyl.

In some embodiments, a compound of structural Formula (II):

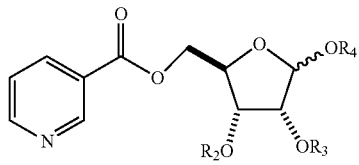

(II)

is provided. In other embodiments, $R_9$, $R_{10}$ and $R_{11}$ are independently alkyl or substituted alkyl. In still other embodiments, $R_9$, $R_{10}$ and $R_{11}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_2$ is $R_9C(O)$—, $R_3$ is $R_{10}C(O)$— and $R_4$ is —H. In other embodiments, $R_9$ and $R_{10}$ are independently alkyl or substituted alkyl. In still other embodiments, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_2$ is $R_9C(O)$—, $R_3$ is $R_{10}C(O)$— and $R_4$ is alkyl. In other embodiments, $R_9$ and $R_{10}$ are independently alkyl or substituted alkyl. In still other embodiments, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_2$ is $R_9C(O)$—, $R_3$ is $R_{10}C(O)$— and $R_4$ is $R_{11}C(O)$—. In other embodiments, $R_9$, $R_{10}$ and $R_{11}$ are independently alkyl or substituted alkyl. In still other embodiments, $R_9$, $R_{10}$ and $R_{11}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_2$ is —H, $R_3$ is $R_{10}C(O)$— and $R_4$ is $R_{11}C(O)$—. In other embodiments, $R_{10}$ and $R_{11}$ are independently alkyl or substituted alkyl. In still other embodiments, $R_{10}$ and $R_{11}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_2$ is $R_9C(O)$—, $R_3$ is —H and $R_4$ is $R_{11}C(O)$—. In other embodiments, $R_9$, and $R_1$ are independently alkyl or substituted alkyl. In still other embodiments, $R_9$, and $R_1$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, a compound of structural Formula (III):

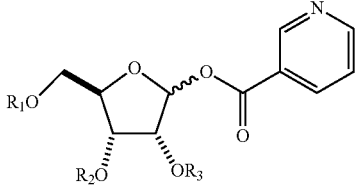

(III)

is provided. In some embodiments, $R_8$, $R_9$ and $R_{10}$ are independently alkyl or substituted alkyl. In other embodiments, $R_8$, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_1$ is $R_8C(O)$—, $R_2$ is $R_9C(O)$— and $R_3$ is $R_{10}C(O)$—. In other embodiments, where $R_8$, $R_9$ and $R_{10}$ are independently alkyl or substituted alkyl. In still other embodiments, $R_8$, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_1$ is —H, $R_2$ is $R_9C(O)$— and $R_3$ is $R_{10}C(O)$—. In other embodiments, $R_9$ and $R_{10}$ are independently alkyl or substituted alkyl. In still other embodiments, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_1$ is $R_8C(O)$—, $R_2$ is —H and $R_3$ is $R_{10}C(O)$—. In other embodiments, $R_8$, and $R_{10}$ are independently alkyl or substituted alkyl. In still other embodiments, $R_8$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_1$ is $R_8C(O)$—, $R_2$ is $R_9C(O)$— and $R_3$ is —H. In other embodiments, $R_8$ and $R_9$ are independently alkyl or substituted alkyl. In still other embodiments, $R_8$ and $R_9$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, a compound Formula (IV

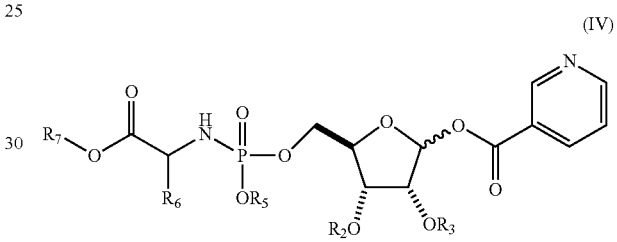

(IV)

is provided. In other embodiments, $R_9$ and $R_{10}$ are independently alkyl or substituted alkyl. In still other embodiments, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$.

In some embodiments, $R_2$ is $R_9C(O)$— and $R_3$ is $R_{10}C(O)$— and $R_9$ and $R_{10}$ are independently alkyl or substituted alkyl. In other embodiments, $R_5$ is aryl or arylalkyl, $R_6$ is alkyl, substituted alkyl, arylalkyl or heteroarylalkyl and $R_7$ is alkyl, alkenyl or arylalkyl. In still other embodiments, $R_9$ and $R_{10}$ are independently —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$. In still other embodiments, $R_5$ is phenyl, napthyl or benzyl, $R_6$ is $CH_3$, —$C_2H_5$, and $R_7$ is —$CH_3$, —$C_2H_5$, —$C_3H_7$, —$CH(CH_3)_2$, —$CH_2CH(CH_3)_2$, —$CH(C_2H_5)(CH_2)_2CH_3$ or cyclopropyl.

In some embodiments, $R_2$ is —H and $R_3$ is $R_{10}C(O)$— and $R_{10}$ is alkyl or substituted alkyl. In other embodiments, $R_5$ is aryl or arylalkyl, $R_6$ is alkyl, substituted alkyl, arylalkyl or heteroarylalkyl and $R_7$ is alkyl, alkenyl or arylalkyl. In still other embodiments, $R_{10}$ is —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$. In still other embodiments, $R_5$ is aryl or arylalkyl, $R_6$ is alkyl, substituted alkyl, arylalkyl or heteroarylalkyl and $R_7$ is alkyl, alkenyl or arylalkyl. In still other embodiments, $R_5$ is phenyl, napthyl or benzyl, $R_6$ is $CH_3$, —$C_2H_5$, and $R_7$ is —$CH_3$, —$C_2H_5$, —$C_3H_7$, —$CH(CH_3)_2$, —$CH_2CH(CH_3)_2$, —$CH(C_2H_5)(CH_2)_2CH_3$ or cyclopropyl.

In some embodiments, $R_2$ is $R_9C(O)$— and $R_3$ is —H and $R_9$ is alkyl or substituted alkyl. In other embodiments, $R_5$ is aryl or arylalkyl, $R_6$ is alkyl, substituted alkyl, arylalkyl or heteroarylalkyl and $R_7$ is alkyl, alkenyl or arylalkyl. In still other embodiments, $R_9$ is —$CH_3$, —$C_2H_5$, —$C_3H_7$, —$CH(CH_3)_2$, —$CH_2CH(CH_3)_2$, —$CH(C_2H_5)(CH_2)_2CH_3$, or —$CH(NH_2)CH(CH_3)_2$. In still other embodiments, $R_5$ is phenyl, napthyl or benzyl, $R_6$ is $CH_3$, —$C_2H_5$, and $R_7$ is —$CH_3$, —$C_2H_5$, —$C_3H_7$, —$CH(CH_3)_2$, —$CH_2CH(CH_3)_2$, —$CH(C_2H_5)(CH_2)_2CH_3$ or cyclopropyl.

Exemplary compounds are provided in Table 1 below.

TABLE 1

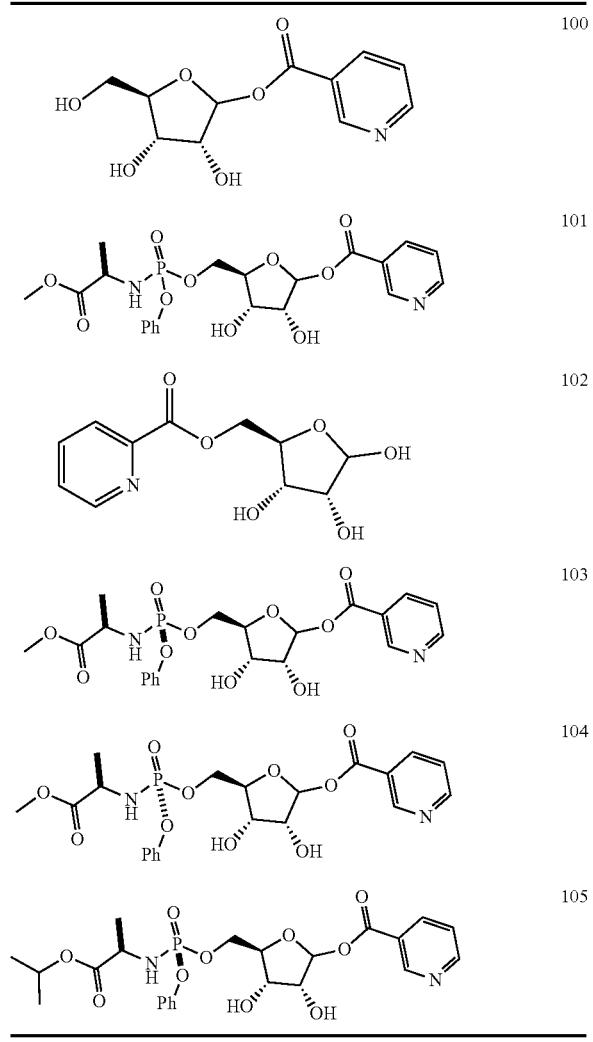

The compounds above can be made by well know procedures some of which are exemplified in the experimental section.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration, intrathecal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN©, complexing agents such as cyclodextrin or dissolution by enhanced ionization (i.e., dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the *U.S. Pharmacopeia* (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof, and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly, intrathecaly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous, intrathecal and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carriers. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pDMI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

For use to treat or prevent infectious disease, the compounds described herein, or pharmaceutical compositions thereof, are administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 micrograms per kilogram to about 5 milligrams per kilogram).

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known agents by comparing the $IC_{50}$, MIC and/or $I_{100}$ of the specific compound disclosed herein with that of a known agent and adjusting the initial dosages accordingly. The optimal dosage may be obtained from these initial values by routine optimization.

In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, In: *The Pharmacological Basis of Therapeutics*, Ch. 1, p. 1).

In some embodiments, the therapeutically effective amount of a compound of structural Formula (I) to treat a disease/disorder or condition disclosed herein, or to bring about a biological effect (e.g., increase $NAD^+$ level, enhance mitochondrial or cellular function, improve metabolic health or cell viability, or provide cytoprotection), is about 1-1000 mg, 1-100 mg, 100-500 mg or 500-1000 mg (e.g., per day or per dose), or as deemed appropriate by the treating physician, which can be administered in a single dose or in divided doses. In further embodiments, the therapeutically effective amount of a compound of structural Formula (I) is about 1-50 mg, 50-100 mg, 100-200 mg, 200-300 mg, 300-400 mg, 400-500 mg, 500-600 mg, 600-700 mg, 700-800 mg, 800-900 mg or 900-1000 mg (e.g., per day or per dose). In additional embodiments, the therapeutically effective amount of a compound of structural Formula (I) is about 50 mg, 100 mg, 150 mg, 200 mg, 250 mg, 300 mg, 400 mg, 500 mg, 600 mg, 700 mg, 800 mg, 900 mg or 1000 mg (e.g., per day or per dose).

In some embodiments, the therapeutically effective amount of a compound of structural Formula (I) is about 100-500 mg, 100-200 mg, 200-300 mg, 300-400 mg or 400-500 mg per day, which can be administered in a single dose (e.g., N mg once daily) or in divided doses (e.g., N/2 mg twice daily). In further embodiments, the therapeutically effective amount of a compound of structural Formula (I) is about 100 mg, 150 mg, 200 mg, 250 mg, 300 mg, 400 mg or 500 mg per day. In certain embodiments, the therapeutically effective amount of a compound of structural Formula (I) is about 200-300 mg per day, or about 200 mg, 250 mg or 300 mg per day.

The therapy may be repeated intermittently. In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating symptoms of medical disorders such as, for example, a metabolic disorder, a cardiovascular disorder, a cerebrovascular disorder, a liver disorder, a kidney disorder or a muscle disorder with the compounds of structural Formula (I) and pharmaceutical compositions thereof are disclosed herein. In some embodiments, the metabolic disorder is type 1 or 2 diabetes, impaired glucose tolerance, insulin resistance, obesity, hyperlipidemia, dyslipidemia, hypercholesterolemia or hypertriglyceridemia; the cardiovascular disorder is cardiomyopathy, heart failure, or myocardial ischemia, infarction or ischemia-reperfusion injury (IRI); the cerebrovascular disorder is stroke or cerebral ischemia, neuroinflammation, multiple sclerosis, hepatic encephalopathy, neurodegeneration, Parkinson's, disease or Alzheimer's disease; the liver disorder is non-alcoholic fatty liver disease (NAFLD), non-alcoholic steatohepatitis (NASH), alcoholic liver disease, alcoholic hepatitis, alcoholic steatohepatitis, liver fibrosis, cirrhosis, liver failure, acute liver failure or chronic liver failure; the kidney disorder is acute kidney injury or renal ischemia or IRI, chronic renal injury including renal failure, glomerulonephritis, diabetic kidney disease; and the muscle disorder is muscle atrophy, cachexia, sarcopenia, muscular dystrophy, Duchenne muscular dystrophy (DMD), myositis, neuromuscular degeneration, ataxia, spinocerebellar ataxia, adult-onset mitochondrial myopathy, Friedreich's ataxia or ataxia-telangiectasia. In practicing the methods, therapeutically effective amounts of the compounds or pharmaceutical compositions, described herein, supra, are administered to the patient with the disorder or condition.

The compounds described herein can increase NAD$^+$ levels in a subject, including in cells, tissues and organs and potentially in the blood. By increasing NAD$^+$ levels, the compounds of structural Formula (I) can improve mitochondrial and cellular function (e.g., DNA repair) in target cells, tissues and organs and improve cell viability. Benefits of improved mitochondrial function include without limitation enhanced mitochondrial oxidative metabolism, mitochondrial respiration, ATP production, mitochondrial membrane potential, mitophagy (autophagy of defective mitochondria) and mitochondrial biogenesis, and reduced levels of reactive oxygen species (ROS). For example, higher NAD$^+$ levels increase the activity of the mitochondrial NAD-dependent deacetylases sirtuin-1 (SIRT1) and sirtuin-3 (SIRT3). SIRT1 promotes autophagy of defective mitochondria, stimulates mitochondrial biogenesis, inhibits the pro-inflammatory transcription factor NF-κB, increases insulin sensitivity, and mimics the effects of calorie restriction. Stimulation of SIRT3 activity increases mitochondrial biogenesis, increases cellular respiration and energy production, reduces ROS levels (e.g., by stimulating mitochondrial superoxide dismutase 2 [SOD2]), promotes cell survival during genotoxic stress, functions as a mitochondrial tumor suppressor, increases insulin sensitivity and sensitizes cells to glucose uptake, and mimics calorie restriction and exercise. Improved DNA repair reduces cell damage and enhances cell function, health and lifespan. In addition, prevention of NAD$^+$ depletion protects neurons in excitotoxic or ischemic conditions.

Therefore, the compounds of structural Formula (I) are useful for treating pellagra, mitochondrial diseases, mitochondria-related diseases and conditions, diseases and conditions associated with acute NAD$^+$ depletion resulting from DNA damage, aging-related disorders and conditions, skin disorders and conditions, and other types of disorders and conditions. In some embodiments, a single compound of structural Formula (I) is used to treat a disease/disorder or condition disclosed herein or to bring about a biological effect disclosed herein (e.g., increase NAD$^+$ level, enhance mitochondrial or cellular function, improve metabolic health or cell viability, or provide cytoprotection). In other embodiments, multiple compounds of structural Formula (I) are used to treat a disease/disorder or condition disclosed herein or to bring about a biological effect disclosed herein. The use of multiple compounds of structural Formula (I) may have an additive effect or potentially a synergistic effect.

The compounds of structural Formula (I) have other beneficial effects. For example, they can enhance immune function in peripheral blood mononuclear cells (e.g., T-cells, B-cells, macrophages and natural killer [NK] cells) based on improved antigen recognition and proliferation as a function of immune surveillance. For such an application, one or more compounds of structural Formula (I) can be employed alone, as a component of a vaccine, as a component of an ex vivo therapy (e.g., a CAR-T cell therapy), or as a component of some other therapy.

Mitochondrial diseases include without limitation mitochondrial myopathies; limb-girdle distribution weakness; Kearns-Sayre syndrome (KSS); Pearson syndrome; Leigh syndrome; Barth syndrome; Friedreich's ataxia; neuropathy, ataxia, retinitis pigmentosa and ptosis (NARP); mitochondrial DNA depletion syndrome (Alper's disease); mitochondrial neurogastrointestinal encephalopathy (MNGIE) syndrome; mitochondrial encephalopathy, lactic acidosis and stroke-like episodes (MELAS) syndrome; myoclonic epilepsy with ragged red fibers (MERRF or Fukuhara syndrome); chronic progressive external ophthalmoplegia (CPEO); Leber's hereditary optic neuropathy (LHON); inherited forms of blindness and deafness (e.g., diabetes mellitus and deafness); and acquired forms of reversible or permanent hearing loss {e.g., type 2 diabetes-associated hearing loss and hearing loss induced by ototoxic chemicals (e.g., heavy metals [e.g., lead], solvents [e.g., styrene and toluene] and asphyxiants [e.g., carbon monoxide]) and medications (e.g., loop diuretics [e.g., bumetanide and furosemide], NSAIDs [e.g., aspirin, celecoxib, diclofenac, ibuprofen and naproxen], PDE5 inhibitors, macrolide antibiotics, aminoglycosides [e.g., gentamicin], platinum-based chemotherapeutics [e.g., carboplatin and cisplatin], paracetamol and quinine)}.

Mitochondria-related diseases and conditions include, but are not limited to, neurodegenerative disorders, neuronal activation disorders, muscle disorders (including eye muscle disorders), fatty acid/beta oxidation disorders, metabolic disorders, inflammatory disorders, vascular disorders (including ocular vascular disorders), renal disorders, liver disorders, tumors, cancers, male and female infertility, and aging-related disorders.

Neurodegenerative disorders include without limitation dementias (e.g., Alzheimer's disease [AD], vascular dementia, dementia with Lewy bodies and frontotemporal dementia [Pick's disease]), motor neuron disorders (e.g., Parkinson's disease, amyotrophic lateral sclerosis [ALS or Lou Gehrig's disease], primary lateral sclerosis [PLS] and spinal muscular atrophy [SMA]), ataxia (e.g., spinocerebellar ataxia/degeneration, Friedreich's ataxia, ataxia-telangiectasia [Louis-Bar syndrome] and fragile X-associated tremor/ataxia syndrome [FXTAS]), dyskinesias (e.g., cerebral palsy, chorea, dystonia and essential tremor), cognitive-motor disorders (e.g., corticobasal degeneration, Huntington's disease [HD] and Parkinson-plus syndromes), chorea-acanthocytosis, retinal neuronal degeneration, Batten disease, DNA-repair syndromes (e.g., Cockayne syndrome), and prion diseases (e.g., Creutzfeldt-Jakob disease).

Neuronal activation disorders include without limitation neurodegenerative disorders (e.g., ALS), neuronal injuries (including traumatic and mechanical injuries to the brain, the spinal cord and the peripheral nervous system [PNS], and excitotoxic neuronal injuries such as those associated with seizures and ischemia), nerve lesions, neuropathies (e.g., peripheral neuropathies [e.g., Charcot-Marie-Tooth disease], mononeuropathies [e.g., those caused by compression, traumatic injury, cumulative trauma, ischemia, inflammation, connective tissue disorders and neoplasms], polyneuropathies [e.g., chronic inflammatory demyelinating polyneuropathy], brachial plexus neuropathies, diabetic neuropathies [e.g. third nerve palsy, mononeuropathy, mononeuropathy multiplex, autonomic neuropathy, thoracoabdominal neuropathy and diabetic amyotrophy], and chemotherapy-induced neuropathies), autoimmune nerve disorders (e.g., multiple sclerosis, Guillain-Barré syndrome, Lambert-Eaton myasthenic syndrome and myasthenia gravis), neuroinflammation, tardy ulnar nerve palsy, and toxic myoneural disorder.

Muscle disorders include, but are not limited to, muscle structure disorders, muscle mass disorders and muscle fatigue disorders. Muscle structure disorders include without limitation myopathies (e.g., cardiomyopathy), neuromuscular degeneration, muscular dystrophy (MD), congenital MD, distal MD, Duchenne MD, Becker MD, Emery-Dreifuss MD, limb-girdle MD, myotonic MD, facioscapulohumeral MD, oculopharyngeal MD, Bethlem myopathy, central core disease, congenital fiber type disproportion, hyaline body myopathy, muscle sodium channel disorders, myotonic dystrophy, myotonic chondrodystrophy, myotubular myopathy, nemaline body disease, myositis, sarcopenia, rhabdomyolysis, and stress urinary incontinence. Muscle mass disorders include without limitation muscle atrophy, cachexia, cartilage degeneration, cerebral palsy, compartment syndrome, critical illness myopathy, inclusion body myositis, sarcopenia, steroid myopathy, and systemic lupus erythematosus (SLE). Muscle fatigue disorders include without limitation chronic fatigue syndrome, fibromyalgia, thyrotoxic myopathy, lipid-storage myopathy, Friedreich's ataxia, glycogen storage diseases (e.g., Pompe disease), intermittent claudication, adult-onset mitochondrial myopathy, MELAS, and mucopolysaccharidosis.

Eye muscle disorders include, but are not limited to, disorders of refraction, disorders of accommodation, disorders of refraction and accommodation, strabismus, progressive external ophthalmoplegia, internal ophthalmoplegia, esotropia, exotropia, hypermetropia, myopia, astigmatism, anisometropia, and presbyopia.

Fatty acid/beta oxidation disorders include without limitation systemic carnitine transporter deficiency, carnitine palmitoyl transferase (CPT) II deficiency, very long-chain acyl-CoA dehydrogenase (LCHAD or VLCAD) deficiency, medium-chain acyl-CoA dehydrogenase (MCAD) deficiency, short-chain acyl-CoA dehydrogenase (SCAD) deficiency, trifunctional enzyme deficiency, and riboflavin-responsive disorders of β-oxidation (RR-MADD).

Metabolic disorders include without limitation lipodystrophy (genetic and acquired), metabolic syndrome, hyperglycemia, impaired glucose tolerance (including prediabetes and diabetes), insulin resistance, hyperinsulinism, diabetes mellitus (including types 1 and 2), diabetic complications (e.g., diabetic neuropathy and diabetic retinopathy), obesity, dyslipidemia, familial hyperlipidemia, hyperchlolesterolemia, non-high-density lipoprotein (HDL) hypercholesterolemia, low-density lipoprotein (LDL) hypercholesterolemia, HDL hypocholesterolemia, hypertriglyceridemia, dyslipoproteinemia, very low-density lipoprotein (VLDL) hyperproteinemia, apolipoprotein A-I hypoproteinemia, hypertension, cardiovascular diseases (e.g., cardiomyopathy [e.g., metabolic cardiomyopathy], cardiac insufficiency, myocardial infarction, atherosclerosis, thrombotic disorders and peripheral vascular diseases), inflammatory disorders (e.g., arthritis, asthma and pancreatitis), liver disorders (e.g., non-alcoholic fatty liver disease [NAFLD] and non-alcoholic steatohepatitis [NASH]), kidney disorders (e.g., chronic kidney disease), gastrointestinal (GI) disorders (e.g., Crohn's disease, hypersensitive intestine syndrome, ulcerative colitis and dyspepsia), neurodegenerative disorders (e.g., Alzheimer disease, Parkinson's disease), demyelinating disorders (e.g., multiple sclerosis), skin disorders (e.g., acne, dermatitis, psoriasis and skin aging), trichosis, adrenal leukodystrophy, edema, ketoacidosis, sexual (e.g., erectile) dysfunction, tumors and cancers.

In some embodiments, the compounds of structural Formula (I) are used to treat hyperglycemia, impaired glucose tolerance and insulin resistance and disorders and conditions related thereto, including prediabetes, types 1 and 2 diabetes, and obesity-related disorders and conditions. The compounds of structural Formula (I) may stimulate SIRT1 and SIRT3 activity, either of which increases insulin sensitivity, sensitizes cells to glucose uptake and mimics calorie restriction. Increased insulin sensitivity can reduce insulin production. Hyperinsulinemia promotes differentiation of preadipocytes into adipocytes. Therefore, reduction of blood insulin level can inhibit fat cell differentiation and adipogenesis and thus can have therapeutic effects on obesity-related disorders and conditions, including but not limited to dyslipogenesis, hyperlipidemia, hypercholesterolemia, atherosclerosis, metabolic syndrome, lipodystrophy and hypertension.

ROS incite inflammation, in part by activating transcriptions factors such as NF-κB that increase the expression of pro-inflammatory cytokines. The compounds of structural Formula (I) disclosed herein can reduce ROS levels by, e.g., stimulating SIRT3 activity. Moreover, the compound of structural Formula (I) can increase the activity of NAD-dependent deacetylase sirtuin-1 (SIRT1), which inhibits NF-κB. NF-κB is the main promoter of the transcription of genes encoding pro-inflammatory cytokines. Thus, compounds of structural Formula (I) are useful for treating inflammatory disorders. Inflammatory disorders include without limitation neuroinflammation (e.g., neuritis [e.g., ocular neuritis and peripheral neuritis], Alzheimer's disease and multiple sclerosis), GI disorders (e.g., gastritis, necrotizing enterocolitis, mucous colitis, ulcerative colitis, inflammatory bowel disease, irritable bowel syndrome, Crohn's disease and celiac disease), peritonitis, pancreatitis (acute and chronic), glomerulonephritis, liver disorders (e.g., hepatitis, non-alcoholic and alcoholic steatohepatitis, cirrhosis and chronic liver disease), multiple organ dysfunction syndrome (e.g., secondary to septicemia or trauma), metabolic disorders (e.g., diabetes [e.g., types 1 and 2 diabetes and juvenile-onset diabetes] and metabolic syndrome), cardiac disorders (e.g., myocarditis and myocardial infarction, congestive heart failure with preserved or reduced ejection fraction), vascular disorders (e.g., vasculitis, atherosclerosis, stroke, peripheral artery disease and shock), reperfusion injury (e.g., due to myocardial ischemia, cerebral ischemia, cardiopulmonary bypass or kidney dialysis), airway disorders (e.g., rhinitis [e.g., allergic rhinitis], esophagitis, asthma, acute respiratory distress syndrome, bronchitis [e.g., chronic bronchitis], pneumonitis and chronic obstructive pulmonary disease [COPD]), arthritis (e.g., osteoarthritis [degenerative joint disease], rheumatoid arthritis, psoriatic arthritis, gouty arthritis, axial spondyloarthritis, ankylosing spondylitis and juvenile arthritis), skin disorders (e.g., dermatitis/eczema, psoriasis, urticaria, dermatosis with acute inflammatory components, and sunburn), Sjögren syndrome, eye disorders (e.g., conjunctivitis, retinitis and AMD), SLE, hypertension and dysmenorrhea (menstrual cramps).

Inflammation is a major stimulant of fibrosis. In part by reducing inflammation, compounds of structural Formula (I) disclosed herein are useful for treating fibrotic disorders. Fibrotic disorders include without limitation cardiomyopathy (e.g., diabetic cardiomyopathy and uremic cardiomyopathy), cardiac fibrosis, myocardial fibrosis, collagen-vascular diseases (e.g., arterial stiffness and vascular fibrosis), atherosclerosis, chronic heart failure, diabetic nephropathy, renal fibrosis, chronic kidney disease (e.g., chronic renal failure), liver fibrosis, cirrhosis, NASH, chronic liver disease, liver failure (e.g., chronic liver failure), pulmonary fibrosis (e.g., idiopathic pulmonary fibrosis and radiation-induced pulmonary fibrosis), cystic fibrosis, and scleroderma (e.g., localized scleroderma and systemic scleroderma/systemic sclerosis).

Vascular disorders include, but are not limited to, cardiovascular diseases (e.g., myocardial ischemia, ischemia-reperfusion injury [IRI], arteriosclerosis and atherosclerosis), cerebrovascular diseases (e.g., cerebral ischemia and IRI), peripheral vascular diseases (e.g., peripheral vascular insufficiency, peripheral artery disease, intermittent/vascular claudication, critical limb ischemia, peripheral artery occlusive disease, and peripheral obliterative arteriopathy), thrombotic/blood clotting/hemostatic disorders (e.g., disseminated intravascular coagulation, deep vein thrombosis, thrombophilia [e.g., due to anti-thrombin III deficiency, protein S deficiency, protein C deficiency or resistance to activated protein C], thrombotic thrombocytopenic purpura, heparin-induced thrombocytopenia, dysfibrinogenemia, atherosclerosis, arteriosclerosis, myocardial ischemia/infarction, angina [e.g., unstable angina], ischemic stroke, sickle cell disease, myeloproliferative neoplasms, cancer metastasis, homocystinuria, and miscarriage), and embolism (e.g., thromboembolism, fat embolism, arterial embolism [e.g., myocardial ischemia, ischemic stroke and acute limb ischemia], and venous embolism [e.g., pulmonary embolism]). As an illustrative example, one or more compounds of structural Formula (I) can be used to treat or prevent thrombosis or a thrombotic disorder, including to reduce or prevent thrombotic events or re-occlusion during or/and after a clot-clearing intervention (e.g., a surgery such as angioplasty).

Ocular vascular disorders include without limitation retinopathy (e.g., hypertensive retinopathy and diabetic retinopathy), macular degeneration (e.g., age-related macular degeneration [AMD]), Stargardt disease, retinal hemorrhage and glaucoma.

Renal disorders include without limitation acute nephritis, chronic nephritis, rapidly progressive nephritis, glomerulonephritis, glomerulosclerosis, hypertensive nephrosclerosis, renal ischemia, IRI, Bartter syndrome, diabetic nephropathy, acute renal failure (acute kidney injury), chronic renal failure, nephrotic syndrome, recurrent hematuria and persistent hematuria.

Liver disorders include without limitation NAFLD, NASH, alcoholic liver disease, hepatitis (e.g., autoimmune hepatitis, hepatitis B and hepatitis C), cholestatic disorders (e.g., cholestasis, primary biliary cholangitis/cirrhosis and primary sclerosing cholangitis), liver injury, chronic liver disease, liver failure (acute and chronic), cirrhosis, and liver cancer.

Tumors (benign and malignant) and cancers include without limitation brain tumors, spinal cord tumors, germ cell tumors, neuroendocrine tumors, carcinoid tumors, tumors and cancers associated with viral infections (e.g., HIV and HTLV-1), carcinomas, sarcomas, and cancers of the digestive/gastrointestinal system, gynecological organs (e.g., the breast), genitourinary system, musculoskeletal system, respiratory system, head and neck, eye, skin (e.g., melanomas), blood (e.g., leukemias, multiple myeloma, Hodgkin's lymphomas and non-Hodgkin's lymphomas), endocrine system (e.g., hormone-dependent cancers such as breast, ovarian, prostate and testicular cancers), neuroendocrine system, neurological system, and germ cells. In some embodiments, one or more compounds of structural Formula (I) are used to treat a cancer of the breast, ovary, colon/large intestine, rectum, pancreas, liver, kidney, lung, prostate, brain or skin. In further embodiments, one or more compound of structural Formula (I) are used to treat a hematological malignancy, such as acute lymphoblastic leukemia (ALL), acute myeloid leukemia (AML), chronic lymphocytic leukemia (CLL), chronic myelogenous leukemia (CML), non-Hodgkin lymphoma or multiple myeloma.

Disorders relating to female infertility include without limitation polycystic ovarian syndrome (PCOS), diminished ovarian reserve, endometriosis, and infertility caused by radiation or chemotherapy. Disorders relating to male infertility include without limitation oligospermia and spermatogenesis caused by medications.

Somatic mutations in mitochondrial DNA increase significantly with age, which can result in defective mitochondria. Moreover, respiratory chain activity diminishes with age. Non-limiting examples of aging-related disorders are described below.

In some embodiments, one or more compounds of structural Formula (I) are used to treat a mitochondria-related disease or condition selected from genetic lipodystrophy, metabolic syndrome, obesity, types 1 and 2 diabetes, NAFLD, NASH, alcoholic liver disease, autoimmune hepatitis, cholestatic liver disease, hemochromatosis, alpha-1 antitrypsin deficiency, other hereditary inborn errors of metabolism, and renal ischemia and IRI.

Diseases and conditions characterized by acute $NAD^+$ depletion due to DNA damage include without limitation exposure to radiation (e.g., UV and ionizing radiation such as X-ray), radiation or chemotherapy-induced disorders (e.g., dermatitis, myositis, myocarditis, colitis, prostatitis, hepatitis, pneumonitis, neuropathies and bone marrow failure), burn injuries (including first-degree burns, second-degree burns and third-degree burns), chemical exposure with manifestation of exfoliative dermatitis, exposure to chemical warfare agents, Stevens-Johnson syndrome, acute respiratory distress syndrome, inhalational lung injury due to smoke or chemical toxins, trauma-related crush injuries (including those with bone fractures), peripheral nerve injuries, spinal cord injuries, and contusion to internal organs (such as the heart, lung, liver and kidney). Such diseases and conditions can generate a large amount of ROS such as superoxide, peroxides and hydroxyl radical, which cause DNA damage and hence cell damage or cell death. In other words, DNA damage induced by, e.g., radiation, chemotherapy or oxidative stress can cause acute $NAD^+$ depletion that results in systemic toxicity and systemic disorders (e.g., dermatitis, pneumonitis, bone marrow failure and neuropathies), as well as local toxicity and local disorders. Exemplary chemical warfare agents include blister agents (e.g., vesicants, nitrogen mustards, sulfur mustards, arsenicals and urticants [e.g., phosgene]), blood agents (e.g., cyanide), pulmonary agents (e.g., phosgene), and nerve agents (e.g., G-series agents [e.g., sarin and soman], GV-series agents and V-series agents).

Reduced $NAD^+$ levels are associated with aging, which leads to aging-related metabolic dysfunction and disorders (e.g., inflammatory disorders). For example, the expression and activity of CD38, which rapidly degrades $NAD^+$ and its precursor NMN, increase during the aging process. Therefore, the compounds of structural Formula (I) described herein are useful for treating aging-related disorders and conditions. Furthermore, the compounds of structural Formula (I) described herein can extend the lifespan of cells by, e.g., slowing or delaying the aging/senescence of cells, promoting the survival of cells, preventing apoptosis of cells, extending the proliferative capacity of cells, increasing cellular resistance to stress (e.g., oxidative stress), mimicking the effects of calorie restriction or promoting wound healing, or any combination thereof. In addition, $NAD^+$ repletion improves stem cell function. Aging-related disorders and conditions include, but are not limited to, aging/senescence, hypertension, eye disorders (e.g., AMD, cataracts and keratoconjunctivitis sicca [dry eye syndrome]), hearing loss, osteoporosis, sarcopenia, dementias (e.g., Alzheimer's disease), metabolic disorders (e.g., metabolic decline, diabetes [including T1D and T2D] and obesity), cardiovascular disorders (e.g., arteriosclerosis), inflammatory disorders (e.g., arthritis and COPD), DNA-repair syndromes (e.g., Cockayne syndrome), and tumors and cancers. Because of their cytoprotective and antioxidant properties, for example, the compounds of structural Formula (I) can be used to prevent or mitigate hearing loss, including noise-induced hearing loss, trauma-induced hearing loss and progressive hearing loss syndromes.

By enhancing cell viability, providing cytoprotection or/and increasing cell lifespan, the compounds of structural Formula (I) can be used to treat disorders characterized by cell degeneration or death. For example, retinal disorders characterized by cell degeneration or death include, but are not limited to, AMD, retinitis pigmentosa, cone-rod dystrophy/degeneration, diabetic retinopathy, Leber's congenital amaurosis, and vision loss.

The cytoprotective compounds of structural Formula (I) can be used to treat other disorders and conditions characterized by cell degeneration or/and cell death, including without limitation neuronal disorders (e.g., Alzheimer's disease, Creutzfeld-Jakob disease, Parkinson's disease, ALS and multiple sclerosis), degeneration of the brain (e.g., cerebellar degeneration and traumatic brain injury), muscle disorders (e.g., muscular dystrophies such as Duchenne MD, facioscapulohumeral MD and myotonic dystrophy), ischemic disorders (e.g., myocardial ischemia/infarction and cerebral ischemia [stroke]/infarction), atherosclerosis, myelodysplastic syndromes (e.g., aplastic anemia), hepatitis (e.g., alcoholic hepatitis, fulminant hepatitis, hepatitis A, hepatitis B, hepatitis C, hepatitis D and hepatitis E), joint disorders (e.g., osteoarthritis), skin atrophy, lichen planus, skin damage caused by UV light, graft rejections, alopecia, AIDS, and cell damage or/and cell death caused by trauma (e.g., to the brain or the spinal cord), surgery, medications, chemicals, biological and chemical toxins, and radiation (e.g., ionizing radiation such as X-ray). To prevent cell damage or/and cell death that may result from, e.g., a medical intervention such as surgery or radiation therapy, one or more compound of structural Formula (I) can be administered to the subject prior to or/and shortly after the intervention.

In part because of their ability to protect cells from the effects of DNA damage and to enhance cell viability and lifespan, the compounds of structural Formula (I) described herein are useful for treating skin disorders and conditions. The skin disorders and conditions can be associated with or caused by, e.g., natural aging, inflammation, oxidative stress or sun damage. Such skin disorders and conditions include without limitation skin wrinkles, dermatitis/eczema (e.g., atopic dermatitis, contact dermatitis [allergic and irritant], exfoliative dermatitis and seborrheic dermatitis), psoriasis (e.g., plaque psoriasis), skin damage caused by sunlight or other light sources (e.g., sunburn, actinic keratosis and xeroderma pigmentosum), keratinization disorders, erythemas (e.g., erythema multiforme and erythema nodosum), dermatomyositis, discoid lupus erythematosus, pemphigoid (e.g., bullous pemphigoid), pemphigus (e.g., pemphigus vulgaris), epidermolysis bullosa, burns (e.g., first-degree burns, second-degree burns and third-degree burns, and thermal burns, radiation burns, chemical burns and electrical burns), wounds, and skin cancers.

Partly because of their cytoprotective properties, the compounds of structural Formula (I) disclosed herein can promote donor graft preservation in organ transplantation. Therefore, the compounds of structural Formula (I) can be applied to cells, tissue or organ employed in transplantation and cell therapies, such as solid-tissue grafts, organ transplants, cell suspensions, stem cells and bone marrow cells. The cells, tissue or organ may be an autograft, an allograft, a syngraft or a xenograft. The cells, tissue or organ can be treated with one or more compounds of structural Formula (I) prior to, concurrently with or/and post administration/implantation of the cells, tissue or organ into a recipient. The cells, tissue or organ can be treated with one or more compounds of structural Formula (I) prior to removal of the cells, tissue or organ from the donor, ex vivo after removal of the cells, tissue or organ from the donor, or post administration/implantation into the recipient. For example, the donor or/and the recipient can be treated systemically with one or more compounds of structural Formula (I) or can have a subset of cells, tissue or organ treated locally with one or more compounds of structural Formula (I). In certain embodiments, the cells, tissue or organ (or the donor or/and the recipient) are treated with an additional therapeutic agent that prolongs graft survival, such as an immunosuppressant, a cytokine or an angiogenic factor, or any combination thereof.

As an example, since enhancement of $NAD^+$ levels promote differentiation of transplanted cells, the use of one or more compounds of structural Formula (I) can improve engraftment of a bone marrow transplant, which can minimize cytopenia (including neutropenia, lymphopenia, anemia and thrombocytopenia), the need for growth factors and complications of infection. As another example, the use of one or more compounds of structural Formula (I) can prevent graft versus host disease (GVHD) in an allogeneic transplant.

In some embodiments, one or more compounds of structural Formula (I) are used in culture medium as a component of an ex vivo therapy, such as a chimeric antigen receptor (CAR) T-cell therapy. A CAR-T cell therapy can be autologous or allogeneic. In certain embodiments, the ex vivo therapy utilizes hematopoietic stem cells (HSC), embryonic stem cells (ESC) or pluripotent stem cells (PSC). One or more compounds of structural Formula (I) can be used to improve the yield of pancreatic endocrine cells during the final stages of in vitro ESC and PSC differentiation into pancreatic islet-like, insulin-secreting cells.

In further embodiments, the compounds of structural Formula (I) are used to enhance mitochondrial or cellular function or/and cellular energy production in oocytes, postnatal female germline stem cells or/and pre-implantation embryos prior to or/and following in vitro fertilization, or following exposure of ovaries, oocytes, postnatal female germline cells or/and preimplantation embryos in vivo. In some embodiments, one or more compounds of structural Formula (I) are used with a solution selected from cell culture medium, oocyte retrieval solution, oocyte washing solution, oocyte in vitro maturation medium, ovarian follicle in vitro maturation medium, oocyte in vitro fertilization medium, vitrification solution and cryopreservation solution in assisted reproduction techniques such as in vitro fertilization. The disclosure encompasses compositions comprising an isolated oocyte, oogonial stem cell (OSC) or OSC progeny, and one or more compounds of structural Formula (I).

In some embodiments the compounds of Formula (I) may be used as lipid lowering agents. The compounds of Formula (I) may be more effective as lipid lowering agent than NA. The lipid lowering effects of the compounds of Formula (I) may be mediated through effects on the liver (DGAT1 inhibition, VLDL and HDL metabolism) and adipocytes/fat tissue (inhibition of lipolysis). The prolonged pharmacology may provide superior effects in reducing liver fat, for the treatment of NAFLD.

In some embodiments the compounds of Formula (I) may be used to improve muscle function. The compounds of Formula (I) may have profound benefits on muscle function superior to NA. This may be mediated by enhancing NAD$^+$ levels and improvement in oxidative phosphorylation associated with improved mitochondrial function. In particular, the compounds of Formula (I) may improve the treatment of myosteatosis associated sarcopenia associated with immobilization, cancer cachexia, chronic malnutrition, liver cirrhosis, and age-related chronic disease.

The therapeutically effective dose of a compound of structural Formula (I) can be administered one, two or more times a day, once every two days, once every three days, twice a week or once a week, or as deemed appropriate by the treating physician. In certain embodiments, the therapeutically effective dose of a compound of structural Formula (I) is administered once or twice daily. As an illustrative example, if the therapeutically effective dose of a compound of structural Formula (I) is about 300 mg per day, 300 mg of the compound can be taken once daily, or 150 mg of the compound can be taken twice daily.

Where a more rapid establishment of a therapeutic level of a compound of structural Formula (I) is desired, such as in the treatment of an ischemia-reperfusion injury, the compound can be administered under a dosing schedule in which a loading dose is administered, followed by (i) one or more additional loading doses and then one or more therapeutically effective maintenance doses, or (ii) one or more therapeutically effective maintenance doses without an additional loading dose, as deemed appropriate by the treating physician. In such a case, a loading dose of a drug is larger (e.g., about 1.5, 2, 3, 4 or 5 times larger) than a subsequent maintenance dose and is designed to establish a therapeutic level of the drug more quickly. The one or more therapeutically effective maintenance doses can be any therapeutically effective amount/dose described herein. In certain embodiments, the loading dose is about three times larger than the maintenance dose. In some embodiments, a loading dose of a compound of structural Formula (I) is administered on day 1 and a maintenance dose is administered on day 2 and thereafter for the duration of therapy. In other embodiments, a first loading dose of a compound of structural Formula (I) is administered on day 1, a second loading dose is administered on day 2, and a maintenance dose is administered on day 3 and thereafter for the duration of therapy. In certain embodiments, the first loading dose is about three times larger than the maintenance dose, and the second loading dose is about two times larger than the maintenance dose.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with the disease and/or disorders disclosed herein. Other therapeutic agents include, without limitation those known for treatment, prevention, or amelioration of one or more symptoms of any the disease and/or disorders disclosed herein.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to, concurrently or subsequently to the one or more additional active ingredients. In other embodiments, the compounds and compositions provided herein are administered in the same or different pharmaceutical compositions of the one or more additional active ingredients.

Other types of therapeutic agents that can be used in combination with the compounds of structural Formula (I) include without limitation sirtuin-activating agents, AMPK-activating agents, CD38 inhibitors, PARP inhibitors, SARM1 inhibitors, ACMSD inhibitors, stimulators of cellular oxygen consumption, NMDA receptor antagonists, acetylcholinesterase inhibitors, antidiabetics, anti-obesity agents, antiplatelet agents, anticoagulants, antihypertensive agents, antioxidants, anti-inflammatory agents, analgesics, anesthetics, anticancer agents, antivirals, antibiotics, antifungals, natural compounds, vitamins and vaccines. The additional therapeutic agents can also include, e.g., farnesoid X receptor agonists, liver X receptor inverse agonists and sunblocks.

Sirtuin-activating agents include agents that increase the activity, level (e.g., expression) or signaling of a sirtuin such as SIRT1 or SIRT3. SIRT1 and SIRT3's beneficial properties are described above. Sirtuin-activating agents mimic calorie restriction, enhance mitochondrial and cellular function, enhance cell viability, increase cell lifespan, increase mitochondrial biogenesis, protect against fatty liver and muscle wasting, and have anti-inflammatory, antidiabetic, cardioprotective and anti-aging effects, among other therapeutic effects. SIRT1-activating agents include without limitation lamin A, methylene blue, resveratrol, SRT-1460, SRT-1720, SRT-2104, SRT-2183, and analogs, derivatives, fragments and salts thereof. In addition to resveratrol, other polyphenols that activate sirtuins such as SIRT1 include, but are not limited to, butein, fisetin, isoliquiritigenin, piceatannol, quercetin, and analogs, derivatives and salts thereof. Metformin increases the activity of sirtuins such as SIRT1 by increasing NAD$^+$ levels via activation of the NAD$^+$ salvage pathway enzyme nicotinamide phosphoribosyltransferase (NAMPT) and by increasing the NAD$^+$/NADH ratio. Other sirtuin-activating agents include amino acids with a branched side chain and metabolites thereof, including without limitation leucine and its metabolites such as hydroxymethylbutyrate and keto-isocaproic acid/isocaproate. Such amino acids increase the levels and stimulate the signaling of sirtuins such as SIRT1 and SIRT3.

AMPK-activating agents include agents that increase the activity, level (e.g., expression) or signaling of 5'-AMP-activated protein kinase (AMPK). AMPK plays an important role in cellular energy homeostasis, largely through stimulation of glucose and fatty acid uptake and oxidation when cellular energy is low. Activation of AMPK stimulates lipolysis, hepatic and skeletal muscle fatty acid oxidation, ketogenesis and glucose uptake, inhibits cholesterol and triglyceride synthesis and lipogenesis (including adipocyte lipogenesis), and modulates insulin secretion by pancreatic β-cells. Activation of AMPK can also increase NAD$^+$ levels. AMPK-activating agents include without limitation sirtuin-activating agents (e.g., resveratrol, quercetin, metformin, and amino acids with a branched side chain and metabolites thereof), thiazolidinedione PPAR-γ agonists (infra, such as pioglitazone and rosiglitazone), cannabinoids, 5-aminoimidazole-4-carboxamide-1-β-D-riboside, berberine, curcumin, dinitrophenol (DNP), epigallocatechin-3-gallate, α-lipoic acid, A-769662, PT-1, adiponectin, ghrelin, leptin, interleukin-6 (IL-6), and analogs, derivatives, fragments and salts thereof.

CD38 expression and activity increase during the aging process, which reduces $NAD^+$ levels and leads to aging-related metabolic dysfunction and disorders (e.g., inflammatory disorders). Inhibition of CD38 increases $NAD^+$ levels and thereby improves mitochondrial and cellular function and increases the activity of sirtuins such as SIRT1 and SIRT3. CD38 inhibitors include, but are not limited to, flavonoids (e.g., apigenin and quercetin), thiazoloquin(az)olin(on)es disclosed in C. Haffner et al., *J. Med. Chem.*, 58:3548-3571 (2015) (e.g., compounds 76a, 76c, 77a, 77c, 77d, 78a, 78c, 78d, 78e, 79a, 79c and 79d), and analogs, derivatives and salts thereof.

Cellular oxygen consumption is a reliable indicator of mitochondrial activity since mitochondrial activity is responsible for nearly all oxygen use by cells. Mitochondria play critical roles in various cellular processes including energy production and biosynthesis. Agents that increase mitochondrial activity can be used, e.g., to treat mitochondrial diseases (e.g., Leigh syndrome and LHON), mitochondria-related diseases and conditions (e.g., metabolic disorders and neurodegenerative disorders [e.g., Alzheimer's disease, Parkinson's disease, ALS, Friedreich's ataxia and FXTAS]), to aid recovery from injury (e.g., traumatic brain injury) or illness, and to delay aging. Stimulators of cellular oxygen consumption increase mitochondrial activity through increased mitochondrial function or/and number. Stimulators of cellular oxygen consumption include without limitation acarbose, chlormadinone (e.g., chlormadinone acetate), desoxymetasone, dichlorophene, enilconazole, flumazenil, quinidine (e.g., quinidine gluconate), succinylsulfathiazole, toltrazuril, and analogs, derivatives and salts thereof.

In some embodiments, one or more compounds of structural Formula (I) are used in combination with an N-methyl-D-aspartate receptor (NMDAR) antagonist to treat a disorder characterized by neurodegeneration or neurotoxicity, such as a dementia (e.g., Alzheimer's disease) or a motor neuron disorder (e.g., Parkinson's disease). In certain embodiments, the NMDAR antagonist is an uncompetitive antagonist (or channel blocker) that has a moderate affinity (e.g., a $K_i$ or $IC_{50}$ from about 200 nM to about 10 μM) for the dizocilpine (MK-801)/phencyclidine-binding site at or near the $Mg^{2+}$-binding site in the opened ion channel of activated NMDAR, which allows the antagonist to inhibit NMDAR-mediated excitotoxicity while preserving physiological NMDAR activity. Such NMDAR uncompetitive antagonists include without limitation alaproclate, amantadine, atornoxetine, budipine, delucemine, dextrallorphan, dextromethorphan, dextrorphan, dexanabinol, eliprodil, ketamine, lanicemine, minocycline, memantine, nitromemantine, NEFA (a tricyclic small molecule), neramexane, orphenadrine, procyclidine, ARL/FPL 12495/12495AA (desglycine metabolite of remacemide), and analogs, derivatives and salts thereof. In some embodiments, the NMDAR antagonist is memantine, nitromemantine, amantadine, lanicemine, neramexane, dextrallorphan, dextromethorphan, dextrorphan (metabolite of dextromethorphan) or procyclidine. In certain embodiments, the NMDAR antagonist is memantine, nitromemantine, dextrallorphan, dextromethorphan or dextrorphan.

In further embodiments, one or more compounds of structural Formula (I) are used in combination with an acetylcholinesterase inhibitor (AChEI) to treat a cognitive disorder (e.g., a dementia such as Alzheimer's disease, Lewy body dementia or Parkinson-associated dementia) or a neuromuscular disorder (e.g., myasthenia gravis). Reversible AChEIs include, but are not limited to, neostigmine, physostigmine, pyridostigmine, rivastigmine, ambenonium, demecarium, donepezil, edrophonium, ladostigil, and analogs, derivatives and salts thereof.

Other therapeutic agents that can be used in conjunction with one or more compounds of structural Formula (I) to treat Parkinson's disease include without limitation levodopa, dopamine agonists (e.g., apomorphine, bromocriptine, cabergoline, lisuride, pergolide, piribedil, pramipexole, ropinirole and rotigotine), catechol-O-methyltransferase (COMT) inhibitors (e.g., entacapone, opicapone and tolcapone), monoamine oxidase B (MAO-B) inhibitors (e.g., ladostigil, safinamide, selegiline and rasagiline), peripheral aromatic L-amino acid decarboxylase inhibitors (e.g., carbidopa), and analogs, derivatives and salts thereof.

In additional embodiments, one or more compounds of structural Formula (I) are used in combination with one or more antidiabetic agents to treat hyperglycemia, insulin resistance or diabetes (e.g., type 1 or type 2), or a disorder associated therewith (e.g., NAFLD or NASH). In certain embodiments, the one or more antidiabetic agents are or include a biguanide (e.g., metformin), a thiazolidinedione (e.g., pioglitazone or rosiglitazone), a GLP-1 agonist (e.g., dulaglutide or semaglutide) or a SGLT2 inhibitor (e.g., empagliflozin or tofogliflozin), or any combination thereof.

Antidiabetic agents include without limitation: AMP-activated protein kinase (AMPK) agonists, including biguanides (e.g., buformin, metformin and phenformin); peroxisome proliferator-activated receptor gamma (PPAR-γ) agonists, including thiazolidinediones (e.g., balaglitazone, ciglitazone, darglitazone, englitazone, lobeglitazone, netoglitazone, pioglitazone, rivoglitazone, rosiglitazone and troglitazone) and saroglitazar (dual PPAR-α/γ agonist); glucagon-like peptide-1 (GLP-1) receptor agonists, including exendin-4, albiglutide, dulaglutide, exenatide, liraglutide, lixisenatide, semaglutide, taspoglutide, CNTO736, CNTO3649, HMI11260C (LAPS-Exendin), NN9926 (OG9S7GT), TT401 and ZY0G1; dual GLP-1 receptor (GLP-1R)/glucagon receptor (GCGR) agonists, including longer-acting oxyntomodulin analogs {e.g., lipid-conjugated OXM analogs (e.g., DualAG disclosed in A. Pocai et al., *Diabetes*, 58:2258-2266 [2009]), PEGylated OXM analogs, cross-linked OXM analogs disclosed in A. Muppidi et al., *ACS Chem. Biol.*, 11:324-328 (2016) and OX-SR disclosed in R. Scott et al., *Peptides*, 104:70-77 (2018)}, HM12525A, JNJ-54728518, LY2944876 (TT-401), MED10382, MK-8521, MOD-6031, NN9277, SAR425899, SP-1373 and ZP2929; dual GLP-1R/gastric inhibitory peptide receptor (GIPR) agonists, including Cpd86, LY3298176, NN9709 (MAR709), SAR438335, ZP-DI-70 and ZP-I-98; triple GLP-1R/GIPR/GCGR agonists, including HM15211 and MAR423; dipeptidyl peptidase 4 (DPP-4) inhibitors, including alogliptin, anagliptin, dutogliptin, evogliptin, gemigliptin, gosogliptin, linagliptin, omarigliptin, saxagliptin, septagliptin, sitagliptin, des-fluoro-sitagliptin, teneligliptin, trelagliptin and vildagliptin; inhibitors of α-glucosidases, including acarbose, miglitol and voglibose; ketohexokinase (KHK) inhibitors, including PF-06835919;

sodium-glucose transport protein 2 (SGLT2) inhibitors, including canagliflozin (also inhibits SGLT1), dapagliflozin, empagliflozin, ertugliflozin, ipragliflozin, remogliflozin etabonate, sotagliflozin (also inhibits SGLT1) and tofogliflozin; blockers of ATP-dependent K⁺ ($K_{ATP}$) channels on pancreatic beta cells, including meglitinides (e.g., mitiglinide, nateglinide and repaglinide) and sulfonylureas {including first generation (e.g., acetohexamide, carbutamide, chlorpropamide, glycyclamide [tolhexamide], metahexamide, tolazamide and tolbutamide) and second generation (e.g., glibenclamide [glyburide], glibornuride, gliclazide, glimepiride, glipizide, gliquidone, glisoxepide and glyclopyramide)}; insulin and analogs thereof, including fast-acting insulin (e.g., insulin aspart, insulin glulisine and insulin lispro), intermediate-acting insulin (e.g., NPH insulin), and long-acting insulin (e.g., insulin degludec, insulin detemir and insulin glargine); and analogs, derivatives and salts thereof.

In further embodiments, one or more compounds of structural Formula (I) are used in combination with one or more anti-obesity agents to treat obesity or hyperlipidemia or a disorder associated therewith, such as a metabolic disorder (e.g., T2D, metabolic syndrome or NAFLD) or a cardiovascular disorder (e.g., atherosclerosis or coronary artery disease). Obesity also promotes inflammatory processes. In certain embodiments, the one or more anti-obesity agents are or include a lipase inhibitor (e.g., orlistat) or/and an antihyperlipidemic agent (e.g., a statin such as atorvastatin, or/and a fibrate such as fenofibrate).

Anti-obesity agents include, but are not limited to: appetite suppressants (anorectics), including amphetamine, dexamphetamine, amfepramone, clobenzorex, mazindol, phentermine (with or without topiramate) and lorcaserin; pro-satiety agents, including ciliary neurotrophic factor (e.g., axokine) and longer-acting analogs of amylin, calcitonin, cholecystokinin (CCK), glucagon (GCG), GLP-1, gastric inhibitory peptide (GIP, also called glucose-dependent insulinotropic polypeptide), leptin, oxyntomodulin (OXM), pancreatic polypeptide (PP), peptide YY (PYY) and neuropeptide Y (NPY); lipase inhibitors, including caulerpenyne, cetilistat, ebelactone A and B, esterastin, lipstatin, orlistat, percyquinin, panclicin A-E, valilactone and vibralactone; agents that increase energy expenditure or/and fat burning, including longer-acting glucagon analogs, glucagon receptor agonists (e.g., NN9030) and dual GLP-1 receptor/glucagon receptor agonists (supra); triiodothyronine ($T_3$) and thyroid hormone receptor-beta (THR-Q) agonists (e.g., MB07344, MB07811, MGL-3196, MGL-3745, VK0214 and VK2809); and fibroblast growth factor 21 (FGF21) and analogs and derivatives thereof (e.g., BMS-986036 [PEGylated FGF21]); antihyperlipidemic agents; other agents that reduce body weight or/and fat mass, including dual GLP-1R/GIPR agonists (supra) and triple GLP-1R/GIPR/GCGR agonists (supra); and analogs, derivatives and salts thereof.

Antihyperlipidemic agents include without limitation: HMG-CoA reductase inhibitors, including statins {e.g., atorvastatin, cerivastatin, fluvastatin, mevastatin, monacolins (e.g., monacolin K [lovastatin]), pitavastatin, pravastatin, rosuvastatin and simvastatin} and flavanones (e.g., naringenin); squalene synthase inhibitors, including lapaquistat, zaragozic acid and RPR-107393; acetyl-CoA carboxylase (ACC) inhibitors, including anthocyanins, avenaciolides, chloroacetylated biotin, cyclodim, diclofop, haloxyfop, soraphens (e.g., soraphen $A_{1\alpha}$), 5-(tetradecyloxy)-2-furancarboxylic acid (TOFA), CP-640186, GS-0976, NDI-010976; 7-(4-propyloxy-phenylethynyl)-3,3-dimethyl-3,4 dihydro-2H-benzo[b][1,4]dioxepine; N-ethyl-N'-(3-{[4-(3, 3-dimethyl-1-oxo-2-oxa-7-azaspiro[4.5]dec-7-yl)piperidin-1-yl]-carbonyl}-1-benzothien-2-yl)urea; 5-(3-acetamidobut-1-ynyl)-2-(4-propyloxyphenoxy)thiazole; and 1-(3-{[4-(3, 3-dimethyl-1-oxo-2-oxa-7-azaspiro[4.5]dec-7-yl)piperidin-1-yl]-carbonyl}-5-(pyridin-2-yl)-2-thienyl)-3-ethylurea; ATP citrate lyase (ACL) inhibitors, including bempedoic acid (ETC-1002), 2-furoic acid, (−)-hydroxycitric acid, BMS-303141, MEDICA-16 and SB-204990; PPAR-α agonists, including fibrates (e.g., bezafibrate, ciprofibrate, clinofibrate, clofibric acid, clofibrate, aluminum clofibrate [alfibrate], clofibride, etofibrate, fenofibric acid, fenofibrate, gemfibrozil, ronifibrate and simfibrate), isoflavones (e.g., daidzein and genistein), and perfluoroalkanoic acids (e.g., perfluorooctanoic acid and perfluorononanoic acid); PPAR-δ agonists, including elafibranor (dual PPAR-α/δ agonist), lanifibranor (triple PPAR-α/δ/γ agonist), GFT505 (dual PPAR-α/δ agonist), GW0742, GW501516 (dual PPAR-β/δ agonist), sodelglitazar (GW677954), MBX-8025, and isoflavones (e.g., daidzein and genistein); PPAR-γ agonists, including thiazolidinediones (supra), saroglitazar (dual PPAR-α/γ agonist), 4-oxo-2-thioxothiazolines (e.g., rhodanine), berberine, honokiol, perfluorononanoic acid, cyclopentenone prostaglandins (e.g., cyclopentenone 15-deoxy-Δ-prostaglandin $J_2$ [15d-PGJ$_2$]), and isoflavones (e.g., daidzein and genistein); liver X receptor (LXR) agonists, including endogenous ligands (e.g., oxysterols such as 22(R)-hydroxycholesterol, 24(S)-hydroxycholesterol, 27-hydroxycholesterol and cholestenoic acid) and synthetic agonists (e.g., acetyl-podocarpic dimer, hypocholamide, N,N-dimethyl-30-hydroxy-cholenamide [DMHCA], GW3965 and T0901317); retinoid X receptor (RXR) agonists, including endogenous ligands (e.g., 9-cis-retinoic acid) and synthetic agonists (e.g., bexarotene, AGN 191659, AGN 191701, AGN 192849, BMS649, LG100268, LG100754 and LGD346); triiodothyronine and thyroid hormone receptor-beta agonists (supra); ketohexokinase inhibitors (supra); inhibitors of acyl-CoA cholesterol acyltransferase (ACAT, also called sterol O-acyltransferase [SOAT], including ACAT1 [SOAT1] and ACAT2 [SOAT2]), including avasimibe, pactimibe, pellitorine, terpendole C and flavanones (e.g., naringenin); inhibitors of stearoyl-CoA desaturase-1 (SCD-1, also called stearoyl-CoA delta-9 desaturase) activity or expression, including aramchol, CAY-10566, CVT-11127, SAR-224, SAR-707, XEN-103; 3-(2-hydroxyethoxy)-4-methoxy-N-[5-(3-trifluoromethylbenzyl)thiazol-2-yl]benzamide and 4-ethylamino-3-(2-hydroxyethoxy)-N-[5-(3-trifluoromethylbenzyl)thiazol-2-yl]benzamide; 1'-{6-[5-(pyridin-3-ylmethyl)-1,3,4-oxadiazol-2-yl]pyridazin-3-yl}-5-(trifluoromethyl)-3,4-dihydrospiro[chromene-2,4'-piperidine]; 5-fluoro-1'-{6-[5-(pyridin-3-ylmethyl)-1,3,4-oxadiazol-2-yl]pyridazin-3-yl}-3,4-dihydrospiro[chromene-2,4'-piperidine]; 6-[5-(cyclopropylmethyl)-4,5-dihydro-1'H,3H-spiro[1,5-benzoxazepine-2,4'-piperidin]-1'-yl]-N-(2-hydroxy-2-pyridin-3-ylethyl)pyridazine-3-carboxamide; 6-[4-(2-methylbenzoyl)piperidin-1-yl]pyridazine-3-carboxylic acid (2-hydroxy-2-pyridin-3-ylethyl)amide; 4-(2-chlorophenoxy)-N-[3-(methyl carbamoyl)phenyl]piperidine-1-carboxamide; the cis-9,trans-11 isomer and the trans-10,cis-12 isomer of conjugated linoleic acid, substituted heteroaromatic compounds disclosed in WO 2009/129625 A1, antisense polynucleotides and peptide-nucleic acids (PNAs) that target mRNA for SCD-1, and SCD-1-targeting siRNAs; cholesterylester transfer protein (CETP) inhibitors, including anacetrapib, dalcetrapib, evacetrapib, torcetrapib and AMG 899 (TA-8995); inhibitors of microsomal triglyceride transfer protein (MTTP) activity or expression, including implitapide, lomitapide, dirlotapide, mitratapide, CP-346086, JTT-130, SLx-4090, anti-sense polynucleotides and PNAs that target mRNA for MTTP, MTTP-targeting microRNAs (e.g., miRNA-30c), and MTTP-targeting siRNAs; GLP-1 receptor agonists (supra), glucagon receptor agonists (supra) and dual GLP-1 receptor/glucagon receptor agonists (supra); fibroblast growth factor 21 (FGF21) and analogs and derivatives thereof, including BMS-986036 (pegylated FGF21); inhibitors of pro-protein convertase subtilisin/kexin type 9 (PCSK9) activity or expression, including berberine (reduces PCSK9 level), annexin A2 (inhibits PCSK9 activity), anti-PCSK9 antibodies (e.g., alirocumab, bococizumab, evolocumab, LGT-209, LY3015014 and RG7652), peptides that mimic the epidermal growth factor-A (EGF-A) domain of the LDL receptor which binds to PCSK9, PCSK9-binding adnectins (e.g., BMS-962476), anti-sense polynucleotides and PNAs that target mRNA for PCSK9, and PCSK9-targeting siRNAs (e.g., inclisiran [ALN-PCS] and ALN-PCSO2); FGF21 and analogs and derivatives thereof (supra). They also include anti-ANGPTL3, anti-ANGTPT4, anti-ANGPTL3/8 mAb and siRNA against ANGPTL3 in development for the treatment of dylipidemia.

Apolipoprotein mimetic peptides, including apoA-I mimetics (e.g., 2F, 3F, 3F-1, 3F-2, 3F-14, 4F, 4F-P-4F, 4F-IHS-4F, 4F2, 5F, 6F, 7F, 18F, 5A, 5A-C1, 5A-CH1, 5A-CH2, 5A-H1, 18A, 37 pA [18A-P-18A], ELK [name], ELK-1A, ELK-1F, ELK-1K1A1E, ELK-1L1K, ELK-1W, ELK-2A, ELK-2A2K2E, ELK-2E2K, ELK-2F, ELK-3E3EK, ELK-3E3K3A, ELK-3E3LK, ELK-PA, ELK-P2A, ELKA [name], ELKA-CH2, ATI-5261, CS-6253, ETC-642, FAMP [name], FREL [name] and KRES [name]) and apoE mimetics (e.g., Ac-hE18A-NH$_2$ [AEM-28], Ac-[R]hE18A-NH$_2$, AEM-28-14, EpK, hEp, mR18L, COG-112, COG-133 and COG-1410); omega-3 fatty acids, including docosahexaenoic acid (DHA), docosapentaenoic acid (DPA), eicosapentaenoic acid (EPA), α-linolenic acid (ALA), fish oils (which contain, e.g., DHA and EPA), and esters (e.g., glyceryl and ethyl esters) thereof, and analogs, derivatives and salts thereof.

In other embodiments, one or more of the compounds of structural Formula (I) are used in combination with an antiplatelet agent or/and an anticoagulant to treat a thrombotic or hemostatic disorder, such as a cardiovascular disorder (e.g., myocardial ischemia/infarction) or a cerebrovascular disorder (e.g., ischemic stroke). In certain embodiments, the antiplatelet agent is or includes a COX-1 inhibitor (e.g., aspirin) or/and a P2Y$_{12}$ inhibitor (e.g., clopidogrel), and the anticoagulant is or includes a direct factor Xa inhibitor (e.g., apixaban or rivaroxaban) or/and a direct thrombin inhibitor (e.g., dabigatran).

Antiplatelet agents include without limitation: cyclooxygenase (e.g., COX-1) inhibitors, including baspirin, naproxen, triflusal and 2-hydroxy-4-trifluoromethylbenzoic acid (the main metabolite of triflusal); thromboxane (e.g., A$_2$) synthase inhibitors, including isogrel, ozagrel, picotamide, ridogrel, samixogrel, terbogrel and EV-077; thromboxane (e.g., A$_2$) receptor antagonists, including dipyridamole, ifetroban, isbogrel, picotamide, ramatroban, ridogrel, samixogrel, terbogrel, terutroban, EV-077 and TRA-418; adenosine diphosphate (ADP) receptor/P2Y$_{12}$ inhibitors, including cangrelor, clopidogrel, prasugrel, ticagrelor and ticlopidine; adenosine reuptake inhibitors, including cilostazol and dipyridamole; glycoprotein IIb/IIIa inhibitors, including abciximab, eptifibatide, tirofiban, TRA-418, and prostacyclin and analogs thereof; phosphodiesterase (e.g., PDE3 or/and PDE5) inhibitors, including cilostazol and dipyridamole; protease-activated receptor 1 (PAR1) antagonists, including vorapaxar; prostacyclin and analogs thereof, including ataprost, beraprost (e.g., esuberaprost), 5,6,7-trinor-4,8-inter-m-phenylene-9-fluoro-PGI$_2$, carbacyclin, isocarbacyclin, clinprost (isocarbacyclin methyl ester), ciprostene, eptaloprost, cicaprost (metabolite of eptaloprost), iloprost, pimilprost, SM-10906 (des-methyl pimilprost), naxaprostene, taprostene, treprostinil, CS-570, OP-2507 and TY-11223; and analogs, derivatives and salts thereof.

Anticoagulants include, but are not limited to: vitamin K antagonists, including 4-hydroxycoumarins (e.g., acenocoumarol, brodifacoum, coumatetralyl, dicoumarol, phenprocoumon, tioclomarol and warfarin) and 1,3-indandiones (e.g., clorindione, diphenadione, fluindione and phenindione); indirect factor Xa inhibitors, including heparin (unfractionated), low molecular weight (MW) heparin (e.g., Fraxiparine®), low MW heparin derivatives (e.g., bemiparin, certoparin, dalteparin, enoxaparin, nadroparin, parnaparin, reviparin and tinzaparin), heparin analogs (e.g., fondaparinux and idraparinux), and heparinoids (e.g., danaparoid, sulodexide and dermatan sulfate); direct factor Xa inhibitors, including apixaban, betrixaban, darexaban, edoxaban, eribaxaban, letaxaban, otamixaban, razaxaban, rivaroxaban, LY-517717 and YM-466; direct thrombin (factor IIa) inhibitors (DTIs), including univalent DTIs (e.g., argatroban, dabigatran, inogatran, melagatran and ximelagatran) and bivalent DTIs (e.g., hirudin and hirudin analogs [e.g., bivalirudin, desirudin and lepirudin]); and analogs, derivatives and salts thereof.

In additional embodiments, one or more compounds of structural Formula (I) are used in combination with one or more antihypertensive agents. Hypertension is a clinical feature of or is a major risk factor for a wide range of disorders. Hypertension-associated disorders include without limitation cardiovascular disorders (e.g., cardiomyopathy, heart failure, atherosclerosis, arteriosclerosis, coronary artery diseases [e.g., myocardial ischemia/infarction], and peripheral vascular diseases [e.g., peripheral artery disease]), cerebrovascular disorders (e.g., stroke and cerebral infarction), metabolic disorders (e.g., metabolic syndrome and T2D), kidney disorders (e.g., diabetic nephropathy, glomerulonephritis, renal ischemia, nephrotic syndrome, and kidney failure [e.g., acute kidney injury and chronic kidney disease]), liver failure (e.g., cirrhosis), and eye disorders (e.g., retinopathy, damage to blood vessels in the eye, and vision loss).

Antihypertensive agents include without limitation: antagonists of the renin-angiotensin-aldosterone system (RAAS), including renin inhibitors (e.g., aliskiren), angiotensin-converting enzyme (ACE) inhibitors (e.g., benazepril, captopril, enalapril, fosinopril, lisinopril, moexipril, perindopril, quinapril, ramipril and trandolapril), angiotensin II receptor type 1 (AT$_1$) antagonists (e.g., azilsartan, candesartan, eprosartan, fimasartan, irbesartan, losartan, olmesartan medoxomil, olmesartan, telmisartan and valsartan), and aldosterone receptor antagonists (e.g., eplerenone and spironolactone); diuretics, including loop diuretics (e.g., bumetanide, ethacrynic acid, furosemide and torsemide), thiazide diuretics (e.g., bendroflumethiazide, chlorothiazide, hydrochlorothiazide, epitizide, methyclothiazide and polythiazide), thiazide-like diuretics (e.g., chlorthalidone, indapamide and metolazone), cicletanine (an early distal tubular diuretic), potassium-sparing diuretics (e.g., amiloride, eplerenone, spironolactone and triamterene), and theobromine; calcium channel blockers, including dihydropyridines (e.g., amlodipine, levamlodipine, cilnidipine, clevidipine, felodipine, isradipine, lercanidipine, nicardipine, nifedipine, nimodipine, nisoldipine and nitrendipine) and non-dihydropyridines (e.g., diltiazem and verapamil); $\alpha_2$-adrenoreceptor agonists, including clonidine, guanabenz, guanfacine, methyldopa and moxonidine; $\alpha_1$-adrenoreceptor antagonists (alpha blockers), including doxazosin, indoramin, nicergoline, phenoxybenzamine, phentolamine, prazosin, terazosin and tolazoline; β-adrenoreceptor ($\beta_1$ or/and $\beta_2$) antagonists (beta blockers), including atenolol, betaxolol, bisoprolol, carteolol, carvedilol, labetalol, metoprolol, nadolol, nebivolol, oxprenolol, penbutolol, pindolol, propranolol and timolol; mixed alpha/beta blockers, including bucindolol, carvedilol and labetalol; endothelin receptor antagonists, including selective $ET_A$ receptor antagonists (e.g., ambrisentan, atrasentan, edonentan, sitaxentan, zibotentan and BQ-123) and dual $ET_A/ET_B$ antagonists (e.g., bosentan, macitentan and tezosentan); other vasodilators, including hydralazine, minoxidil, theobromine, sodium nitroprusside, organic nitrates (e.g., isosorbide mononitrate, isosorbide dinitrate and nitroglycerin, which are converted to nitric oxide in the body), endothelial nitric oxide synthase (eNOS) stimulators (e.g., cicletanine), activators of soluble guanylate cyclase (e.g., cinaciguat and riociguat), phosphodiesterase type 5 (PDE5) inhibitors (e.g., avanafil, benzgamidenafil, dasantafil, dynafil, lodenafil, mirodenafil, sildenafil, tadalafil, udenafii, ardenati, dipyridamole, papaverine, propentofylline, zaprinast and T-1032), prostaglandin $E_1$ (alprostadil) and analogs thereof (e.g., limaprost and misoprostol), prostacyclin and analogs thereof (supra), non-prostanoid prostacyclin receptor agonists (e.g., 1-phthalazinol, ralinepag, selexipag, ACT-333679 [MRE-269, active metabolite of selexipag], and TRA-418), phospholipase C (PLC) inhibitors, and protein kinase C (PKC) inhibitors (e.g., BIM-1, BM-2, BIM-3, BIM-8, chelerythrine, cicletanine, gossypol, miyabenol C, myricitrin, ruboxistaurin and verbascoside); minerals, including magnesium and magnesium sulfate; and analogs, derivatives and salts thereof.

In certain embodiments, the one or more antihypertensive agents are or include a thiazide or thiazide-like diuretic (e.g., hydrochlorothiazide or chlorthalidone), a calcium channel blocker (e.g., amlodipine or nifedipine), an ACE inhibitor (e.g., benazepril, captopril or perindopril) or an angiotensin II receptor antagonist (e.g., olmesartan rnedoxormil, olmesartan, telmisartan or valsartan), or any combination thereof.

In further embodiments, one or more compounds of structural Formula (I) are used in combination with one or more antioxidants to treat a disorder whose pathogenesis or pathophysiology involves oxidative stress or/and oxidative damage/injury. Such oxidative disorders include without limitation neurodegenerative disorders (e.g., Alzheimer's, Huntington's and Parkinson's diseases, ALS and multiple sclerosis), metabolic disorders (e.g., types 1 and 2 diabetes and metabolic syndrome), cardiovascular disorders (e.g., atherosclerosis, heart failure, myocardial ischemia/infarction and IRI), cerebrovascular disorders (e.g., stroke and IRI), kidney disorders (e.g., diabetic nephropathy), liver disorders (e.g., cirrhosis), and eye disorders (e.g., AMD). Furthermore, oxidants (e.g., ROS) and oxidized molecules (e.g., oxidized lipids) can be highly inflammatory.

Antioxidants include without limitation: vitamins and analogs thereof, including vitamin A, vitamin $B_3$ (e.g., niacin [nicotinic acid] and nicotinamide), vitamin C (ascorbic acid), vitamin E (including tocopherols [e.g. α-tocopherol] and tocotrienols), and vitamin E analogs (e.g., trolox [water-soluble]); carotenoids, including carotenes (e.g., p-carotene), xanthophylls (e.g., lutein, zeaxanthin and meso-zeaxanthin), and carotenoids in saffron (e.g., crocin and crocetin); sulfur-containing antioxidants, including glutathione (GSH), N-acetyl-L-cysteine (NAC), bucillamine, S-nitroso-N-acetyl-L-cysteine (SNAC), S-allyl-L-cysteine (SAC), S-adenosyl-L-methionine (SAM), α-lipoic acid and taurine; scavengers of ROS and radicals, including carnosine, N-acetylcarnosine, curcuminoids (e.g., curcumin, demethoxycurcumin and tetrahydrocurcumin), cysteamine, ebselen, glutathione, hydroxycinnamic acids and derivatives (e.g., esters and amides) thereof (e.g., caffeic acid, rosmarinic acid and tranilast), melatonin and metabolites thereof, nitrones (e.g., disufenton sodium [NXY-059]), nitroxides (e.g., XJB-5-131), polyphenols (e.g., flavonoids [e.g., apigenin, genistein, luteolin, naringenin and quercetin]), superoxide dismutase mimetics (infra), tirilazad, vitamin C, vitamin E and analogs thereof (e.g., α-tocopherol and trolox), and xanthine derivatives (e.g., pentoxifylline); inhibitors of enzymes that produce ROS, including NADPH oxidase (NOX) inhibitors (e.g., apocynin, decursin and decursinol angelate [both inhibit NOX-1, -2 and -4 activity and expression], diphenylene iodonium, and GKT-831 [formerly GKT-137831, a dual NOX1/4 inhibitor]), NADH: ubiquinone oxidoreductase (complex I) inhibitors (e.g., metformin and rotenone), and myeloperoxidase inhibitors (e.g., azide and 4-aminobenzoic acid hydrazide, and apoE mimetics such as AEM-28 and AEM-28-14); substances that mimic or increase the activity or production of antioxidant enzymes, including superoxide dismutase (SOD) {e.g., SOD mimetics such as manganese (III)- and zinc (III)-porphyrin complexes (e.g., MnTBAP, MnTMPyP and ZnTBAP), manganese (II) penta-azamacrocyclic complexes (e.g., M40401 and M40403), manganese (III)-salen complexes (e.g., those disclosed in U.S. Pat. No. 7,122,537) and OT-551 (a cyclopropyl ester prodrug of tempol hydroxylamine), and resveratrol and apoA-I mimetics such as 4F (both increase expression)}, catalase (e.g., catalase mimetics such as manganese (III)-salen complexes [e.g., those disclosed in U.S. Pat. No. 7,122,537], and zinc [increases activity]), glutathione peroxidase (GPx) (e.g., apomorphine and zinc [both increase activity], and beta-catenin, etoposide and resveratrol [all three increase expression]), glutathione reductase (e.g., 4-tert-butylcatechol and redox cofactors such as flavin adenine dinucleotide [FAD] and NADPH [all three enhance activity]), glutathione S-transferase (GST) (e.g., phenylalkyl isothiocyanate-cysteine conjugates {e.g., S—[N-benzyl (thiocarbamoyl)]-L-cysteine}, phenobarbital, rosemary extract and carnosol [all enhance activity]), thioredoxin (Trx) (e.g., geranylgeranylacetone, prostaglandin $E_1$ and sulforaphane [all increase expression]), NADPH-quinone oxidoreductase 1 (NQO1) {e.g., flavones [e.g., β-naphthoflavone (5,6-benzoflavone)] and triterpenoids [e.g., oleanolic acid analogs such as TP-151 (CDDO), TP-155 (CDDO methyl ester), TP-190, TP-218, TP-222, TP-223 (CDDO carboxamide), TP-224 (CDDO monomethylamide), TP-225, TP-226 (CDDO dimethylamide), TP-230, TP-235 (CDDO imidazolide), TP-241, CDDO monoethylamide, CDDO mono(trifluoroethyl)amide, and (+)-TBE-B], all of which increase expression by activating Nrf2}, heme oxygenase 1 (HO-1) {e.g., curcuminoids (e.g., curcumin), triterpenoids (e.g., oleanolic acid analogs [supra, such as TP-225]), and apoA-I mimetics (supra, such as 4F), all of which increase expression}, and paraoxonase 1 (PON-1) (e.g., apoE mimetics [supra, such as AEM-28 and AEM-28-14] and apoA-I mimetics [supra, such as 4F], both types increasing activity); activators of transcription factors that upregulate expression of antioxidant enzymes, including activators of nuclear factor (erythroid-derived 2)-like 2 (NFE2L2 or Nrf2) {e.g., bardoxolone methyl, OT-551, fumarates (e.g., dimethyl and monomethyl fumarate), dithiolethiones (e.g., oltipraz), flavones (e.g., p-naphthoflavone), isoflavones (e.g., genistein), sulforaphane, trichostatin A, triterpenoids (e.g., oleanolic acid analogs [supra, such as TP-225]), and melatonin (increases Nrf2 expression)}; mitochondria-targeted antioxidants, including MitoE and MitoQ; other kinds of antioxidants, including anthocyanins, benzenediol abietane diterpenes (e.g., carnosic acid), cyclopentenone prostaglandins (e.g., 15d-PGJ$_2$), flavonoids {e.g., flavonoids in *Ginkgo biloba* (e.g., myricetin and quercetin [increases levels of GSH, SOD, catalase, GPx and GST]), prenylflavonoids (e.g., isoxanthohumol), flavones (e.g., apigenin), isoflavones (e.g., genistein), flavanones (e.g., naringenin) and flavanols (e.g., catechin and epigallocatechin-3-gallate)}, omega-3 fatty acids and esters thereof (supra), phenylethanoids (e.g., tyrosol and hydroxytyrosol), retinoids (e.g., all-trans retinol [vitamin A]), stilbenoids (e.g., resveratrol), uric acid, apoA-I mimetics (e.g., 4F), apoE mimetics (e.g., AEM-28 and AEM-28-14), and minerals (e.g., selenium and zinc [e.g., zinc monocysteine]); and analogs, derivatives and salts thereof.

In certain embodiments, the one or more antioxidants are or include a vitamin or an analog thereof (e.g., vitamin E or an analog thereof such as α-tocopherol or trolox) or/and an ROS or radical scavenger (e.g., melatonin or/and glutathione). In other embodiments, the antioxidant or/and the natural compound are selected from resveratrol, pterostilbene, ellagic acid, urolithin A, quercetin, coenzyme Q, glutathione, N-acetyl-L-cysteine, α-lipoic acid, melatonin, creatine, S-adenosyl methionine, leucine, pyruvic acid/pyruvate and combinations thereof.

In some embodiments, one or more compounds of structural Formula (I) are used in conjunction with one or more B vitamins selected from thiamine ($B_1$), riboflavin ($B_2$), niacin ($B_3$), pantothenic acid ($B_5$), pyridoxine ($B_6$), biotin ($B_7$), folic acid ($B_9$) and cobalamin ($B_{12}$). In certain embodiments, one or more compound of structural Formula (I) are used in conjunction with vitamin $B_1$, $B_2$, $B_3$ or $B_6$, or any combination thereof.

In additional embodiments, one or more compounds of structural Formula (I) are used in combination with one or more anti-inflammatory agents to treat an inflammatory disorder. Inflammation contributes to the pathogenesis or pathophysiology of a wide range of disorders. Furthermore, inflammation is a major stimulant of fibrosis. In certain embodiments, the one or more anti-inflammatory agents are or include and NSAID or/and an inhibitor of a pro-inflammatory cytokine or a receptor therefor or the production thereof (e.g., TNF-α, IL-4, IL-6 or IL-23, or any combination thereof).

Anti-inflammatory agents include without limitation: non-steroidal anti-inflammatory drugs (NSAIDs), including those listed below; immunomodulators, including imides (e.g., thalidomide, lenalidomide, pomalidomide and apremilast) and xanthine derivatives (e.g., lisofylline, pentoxifylline and propentofylline); immunosuppressants, including interferon-beta (IFN-3 glucocorticoids (infra), antimetabolites (e.g., hydroxyurea [hydroxycarbamide], antifolates [e.g., methotrexate], and purine analogs [e.g., azathioprine, mercaptopurine and thioguanine]), pyrimidine synthesis inhibitors (e.g., leflunomide and teriflunomide), calcineurin inhibitors (e.g., ciclosporin [cyclosporine A], pimecrolimus and tacrolimus), inosine-5'-monophosphate dehydrogenase (IMPDH) inhibitors (e.g., mycophenolic acid and derivatives thereof [e.g., mycophenolate sodium and mycophenolate mofetil]), mechanistic/mammalian target of rapamycin (mTOR) inhibitors (e.g., rapamycin [sirolimus], deforolimus [ridaforolimus], everolimus, temsirolimus, umirolimus [biolimus A9], zotarolimus and RTP-801), modulators of sphingosine-1-phosphate receptors (e.g., S1PR1) (e.g., fingolimod), and serine C-palmitoyltransferase inhibitors (e.g., myriocin); anti-inflammatory cytokines and compounds that increase their production, including IL-10 and compounds that increase IL-10 production {e.g., S-adenosyl-L-methionine, melatonin, metformin, rotenone, curcuminoids (e.g., curcumin), prostacyclin and analogs thereof (supra), triterpenoids (e.g., oleanolic acid analogs [supra, such as TP-225]), and apoA-I mimetics (supra, such as 4F); inhibitors of pro-inflammatory cytokines or receptors therefor, including inhibitors of (e.g., antibodies or fragments thereof targeting) tumor necrosis factor-alpha (TNF-α) (e.g., adalimumab, certolizumab pegol, golimumab, infliximab, etanercept, bupropion, curcumin catechins and ART-621) or the receptor therefor (TNFR1), inhibitors of thymic stromal lymphopoietin (e.g., anti-TSLP antibodies and fragments thereof [e.g., tezepelumab and M702] and immunoconjugates comprising the extracellular domain of TSLPR) or the receptor therefor (TSLPR), inhibitors of (e.g., antibodies or fragments thereof targeting) pro-inflammatory interferons (e.g., interferon-alpha [IFN-α]) or receptors therefor, inhibitors of (e.g., antibodies or fragments thereof targeting) pro-inflammatory interleukins or receptors therefor {e.g., IL-1 (e.g., IL-1α and IL-1β [e.g., canakinumab and rilonacept]) or IL-1R (e.g., anakinra and isunakinra [EBI-005]), IL-2 or IL-2R (e.g., basiliximab and daclizumab), IL-4 or IL-4R (e.g., dupilumab), IL-5 (e.g., mepolizumab and reslizumab) or IL-5R, IL-6 (e.g., clazakizumab, elsilimomab, olokizumab, siltuximab and sirukumab) or IL-6R (e.g., sarilumab and tocilizumab), IL-8 or IL-8R, IL-12 (e.g., briakinumab and ustekinumab) or IL-12R, IL-13 or IL-13R, IL-15 or IL-15R, IL-17 (e.g., ixekizumab and secukinumab) or IL-17R (e.g., brodalumab), IL-18 (e.g., GSK1070806) or IL-18R, IL-20 (e.g., the antibody 7E) or IL-20R, IL-22 (e.g., fezakinumab) or IL-22R, IL-23 (e.g., briakinumab, guselkumab, risankizumab, tildrakizumab [SCH-900222], ustekinumab and BI-655066) or IL-23R, IL-31 (e.g., anti-IL-31 antibodies disclosed in U.S. Pat. No. 9,822,177) or IL-31R (e.g., anti-IL-31 receptor A antibodies such as nemolizumab), IL-33 or IL-33R, and IL-36 or IL-36R}, and inhibitors of monocyte chemoattractant protein 1 (MCP-1) {e.g., bindarit, anti-MCP1 antibodies (e.g., 5D3-F7 and 10F7), MCP1-binding peptides (e.g., HSWRHFHTLGGG (SEQ ID NO: 2)), and MCP1-binding RNA aptamers (e.g., ADR22 and mNOX-E36 [a spiegelmer])} or receptors therefor (e.g., CCR2 antagonists such as spiropiperidines [e.g., RS-29634, RS-102895 and RS-504393]); inhibitors of the production of pro-inflammatory cytokines or receptors therefor, including inhibitors of the production of TNF-α {e.g., N-acetyl-L-cysteine, S-adenosyl-L-methionine, L-carnitine, hydroxychloroquine, melatonin, parthenolide, pirfenidone, sulfasalazine, mesalazine (5-aminosalicylic acid), taurine, flavonoids (e.g., epigallocatechin-3-gallate [EGCG], naringenin and quercetin), omega-3 fatty acids and esters thereof, glucocorticoids, immunomodulatory imides and xanthine derivatives, PDE4 inhibitors, serine protease inhibitors (e.g., gabexate and nafamostat), prostacyclin and analogs thereof, SOCS1 mimnetics (infi), myxoma virus M013 protein, *Yersinia* YopM protein, apoA-I mimetics (e.g., 4F), and apoE mimetics (e.g., AEM-28 and hEp)}, IFN-α (e.g., alefacept), IL-1 (e.g., IL-1α and IL-1β) (e.g., chloroquine, hydroxychloroquine, nafamostat, pirfenidone, sulfasalazine, mesalazine, prostacyclin and analogs thereof, glucocorticoids, TNF-α inhibitors, PAR1 antagonists [e.g., vorapaxar], M013 protein, YopM protein and apoA-I mimetics [e.g., 4F]), IL-1β (e.g. melatonin metformin, rotenone, flavonoids [e.g., EGCG and naringenin], annexin A1 mimetics, and caspase-1 inhibitors [e.g., belnacasan, pralnacasan and parthenolide]), IL-2 (e.g., glucocorticoids, calcineurin inhibitors and PDE4 inhibitors), IL-4 (e.g., glucocorticoids and serine protease inhibitors [e.g., gabexate and nafamostat]), IL-5 (e.g., glucocorticoids), IL-6 (e.g., nafamostat, parthenolide, prostacyclin and analogs thereof, tranilast, L-carnitine, taurine, flavonoids [e.g., EGCG, naringenin and quercetin], omega-3 fatty acids and esters thereof, glucocorticoids, immunomodulatory imides, TNF-α inhibitors, M013 protein and apoE mimetics [e.g., AEM-28 and hEp]), IL-8 (e.g., alefacept and glucocorticoids), IL-12 (e.g., apilimod, PDE4 inhibitors and YopM protein), IL-15 (e.g., YopM protein), IL-17 (e.g., protein kinase C inhibitors such as sotrastaurin), IL-18 (e.g., M013 protein, YopM protein and caspase-1 inhibitors), and IL-23 (e.g., apilimod, alefacept and PDE4 inhibitors), and MCP-1 (e.g., EGCG, melatonin and tranilast); inhibitors of pro-inflammatory transcription factors or their activation or expression, including inhibitors of NF-fB or its activation or expression {e.g., aliskiren, melatonin, minocycline and parthenolide (both inhibit NF-κB nuclear translocation), nafamostat, niclosamide, (−)-DTIMEQ, IT-603, IT-901, PBS-1086, flavonoids (e.g., EGCG and quercetin), hydroxycinnamic acids and esters thereof (e.g., ethyl caffeate), lipoxins (e.g., 15-epi-LXA4 and LXB4), omega-3 fatty acids and esters thereof, stilbenoids (e.g., resveratrol), statins (e.g., rosuvastatin), triterpenoids (e.g., oleanolic acid analogs such as TP-225), TNF-α inhibitors, apoE mimetics (e.g., AEM-28), M013 protein, penetratin, and activators of sirtuin 1 (SIRT1, which inhibits NF-κB) (e.g., flavones [e.g., luteolin], phenylethanoids [e.g., tyrosol, which induces SIRT1 expression], stilbenoids [e.g., resveratrol, which increases SIRT1 activity and expression] and lamin A)}, and inhibitors of STAT (signal transducer and activator of transcription) proteins or their activation or expression {e.g., Janus kinase 1 (JAK1) inhibitors (e.g., itacitinib, upadacitinib, GLPG0634 and GSK2586184), JAK2 inhibitors (e.g., lestaurtinib, pacritinib, CYT387, TG101348, SOCS1 mimetics and SOCS3 mimeics), JAK3 inhibitors (e.g., ASP-015K, R348 and VX-509), dual JAK1/JAK2 inhibitors (e.g., baricitinib and ruxolitinib), dual JAK1/JAK3 inhibitors (e.g., tofacitinib), suppressor of cytokine signaling (SOCS) mimetic peptides (e g., SOCS1 mimetics [e.g., SOCS1-KIR, NewSOCS1-KIR, PS-5 and Tkip] and SOCS3 mimetics), niclosamide, hydroxycinnamic acids and esters thereof (e.g., rosmarinic acid), and lipoxins (e.g., 15-epi-LXA4 and LXB4)}; inhibitors of pro-inflammatory prostaglandins (e.g., prostaglandin $E_2$ [$PGE_2$]) or receptors therefor (e.g., $EP_3$) or the production thereof, including cyclooxygenase inhibitors (e.g., NSAIDs [including non-selective COX-1/COX-2 inhibitors such as aspirin and selective COX-2 inhibitors such as coxibs], glucocorticoids [which inhibit COX activity and expression], omega-3 fatty acids and esters thereof, curcuminoids [e.g., curcumin], stilbenoids [e.g., resveratrol, which inhibits COX-1 and -2 activity and expression], and vitamin E and analogs thereof [e.g., α-tocopherol and trolox]), cyclopentenone prostaglandins (e.g., prostaglandin $J_2$ [$PGJ_2$], A12-$PGJ_2$ and 15-deoxy-A12,14-$PGJ_2$), hydroxycinnamic acids and esters thereof (e.g., ethyl caffeate, which suppresses COX-2 expression), and triterpenoids (e.g., oleanolic acid analogs such as TP-225, which suppress COX-2 expression); inhibitors of leukotrienes or receptors therefor or the production thereof, including cysteinyl leukotriene receptor 1 (cysLTR1) antagonists (e.g., cinalukast, gemilukast [dual cysLTR1/cysLTR2 antagonist], iralukast, montelukast, pranlukast, tomelukast, verlukast, zafirlukast, CP-195494, CP-199330, ICI-198615, MK-571 and lipoxins [e.g., LXA4 and 15-epi-LXA4]), cysLTR2 antagonists (e.g., HAMI-3379), 5-iipoxygenase (5-LOX) inhibitors (e.g., baicalein, caffeic acid curcunin, hyperforin, γ-linolenic acid [CLA], meclofenarnic acid, meclofenaniate sodium, minocycline, zileuton, MK-886, and omega-3 fatty acids and esters thereof), and immunomodulatory xanthine derivatives; inhibitors of phospholipase A2 (e.g., secreted and cytosolic PLA2), including glucocorticoids, arachidonyl trifluoromethyl ketone, bromoenol lactone, chloroquine, cytidine 5-diphosphoamines, darapladib, quinacrine, vitamin E, RO-061606, ZPL-521, lipocortins (annexins, such as annexin A1), and annexin mimetic peptides (e.g., annexin A1 mimetics [e.g., Ac2-26 and CGEN-855A]); suppressors of C-reactive protein (CRP) activity or level, including statins (e.g., rosuvastatin), thiazolidinediones (supra), DPP-4 inhibitors (supra), stilbenoids (e.g., resveratrol), epigallocatechin-3-gallate and CRP-i2; mast cell stabilizers, including cromoglicic acid (cromolyn), ketotifen, methylxanthines, nedocromil, nicotinamide, olopatadine, omalizumab, pemirolast, quercetin and zinc sulfate; phosphodiesterase inhibitors, including PDE4 inhibitors (e.g., apremilast, cilomilast, ibudilast, piclamilast, roflumilast, crisaborole, diazepam, luteolin, mesembrenone, rolipram, AN2728 and E6005); specialized pro-resolving mediators (SPMs), including metabolites of polyunsaturated fatty acids (PUFAs) such as lipoxins (e.g., LXA4, 15-epi-LXA4, LXB4 and 15-epi-LXB4), resolvins (e.g., resolvins derived from 5Z,8Z,11Z,14Z,17Z-eicosapentaenoic acid [EPA], resolvins derived from 4Z,7Z,10Z,13Z,16Z,19Z-docosahexaenoic acid [DHA], and resolvins derived from 7Z,10Z,13Z,16Z, 19Z-docosahexaenoic acid [n-3 DPA]), protectins/neuroprotectins (e.g., DHA-derived protectins/neuroprotectins and n-3 DPA-derived protectins/neuroprotectins), maresins (e.g., DHA-derived maresins and n-3 DPA-derived maresins), n-3 DPA metabolites, n-6 DPA (4Z,7Z,10Z,13Z,16Z-docosapentaenoic acid) metabolites, oxo-DHA metabolites, oxo-DPA metabolites, docosahexaenoyl ethanolamide metabolites, cyclopentenone prostaglandins (e.g., $\Delta12$-$PGJ_2$ and 15-deoxy-$\Delta12,14$-$PGJ_2$), and cyclopentenone isoprostanes (e.g., 5,6-epoxyisoprostane $A_2$ and 5,6-epoxyisoprostane $E_2$); other kinds of anti-inflammatory agents, including pirfenidone, nintedanib, vitamin A, omega-3 fatty acids and esters thereof, apoA-I mimetics (e.g., 4F), apoE mimetics (e.g., AEM-28 and AEM-28-14), and antioxidants (e.g., sulfur-containing antioxidants); and analogs, derivatives, fragments and salts thereof.

Non-steroidal anti-inflammatory drugs (NSAIDs) include without limitation: acetic acid derivatives, such as aceclofenac, bromfenac, diclofenac, etodolac, indomethacin, ketorolac, nabumetone, sulindac, sulindac sulfide, sulindac sulfone and tolmetin; anthranilic acid derivatives (fenamates), such as flufenamic acid, meclofenamic acid, mefenamic acid and tolfenamic acid; enolic acid derivatives (oxicams), such as droxicam, isoxicam, lornoxicam, meloxicam, piroxicam and tenoxicam; propionic acid derivatives, such as fenoprofen, flurbiprofen, ibuprofen, dexibuprofen, ketoprofen, dexketoprofen, loxoprofen, naproxen and oxaprozin; salicylates, such as diflunisal, salicylic acid, acetylsalicylic acid (aspirin), choline magnesium trisalicylate, salsalate and mesalazine; COX-2-selective inhibitors, such as apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, niflumic acid, DuP-697, CG100649, GW406381, NS-398, SC-236, SC-58125, benzothieno[3,2-d]pyrimidin-4-one sulfonamide thio-derivatives, and COX-2 inhibitors derived from *Tribulus terrestris*; other kinds of NSAIDs, such as monoterpenoids (e.g., eucalyptol and phenols [e.g., carvacrol]), anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) {e.g., chebulagic acid, licofelone, 2-(3,4,5-trimethoxyphenyl)-4-(N-methylindol-3-yl)thiophene, and di-tert-butylphenol-based compounds (e.g., DTPBHZ, DTPINH, DTPNHZ and DTPSAL)}; and analogs, derivatives and salts thereof.

The glucocorticoid class of corticosteroids has anti-inflammatory and immunosuppressive properties. Glucocorticoids include without limitation hydrocortisone types (e.g., cortisone and derivatives thereof [e.g., cortisone acetate], hydrocortisone and derivatives thereof [e.g., hydrocortisone acetate, hydrocortisone-17-aceponate, hydrocortisone-17-buteprate, hydrocortisone-17-butyrate and hydrocortisone-17-valerate], prednisolone, methylprednisolone and derivatives thereof [e.g., methylprednisolone aceponate], prednisone, and tixocortol and derivatives thereof [e.g., tixocortol pivalate]), betamethasone types (e.g., betamethasone and derivatives thereof [e.g., betamethasone dipropionate, betamethasone sodium phosphate and betamethasone valerate], dexamethasone and derivatives thereof [e.g., dexamethasone sodium phosphate], and fluocortolone and derivatives thereof [e.g., fluocortolone caproate and fluocortolone pivalate]), halogenated steroids (e.g., alclometasone and derivatives thereof [e.g., alclometasone dipropionate], beclometasone and derivatives thereof [e.g., beclometasone dipropionate], clobetasol and derivatives thereof [e.g., clobetasol-17-propionate], clobetasone and derivatives thereof [e.g., clobetasone-17-butyrate], desoximetasone and derivatives thereof [e.g., desoximetasone acetate], diflorasone and derivatives thereof [e.g., diflorasone diacetate], diflucortolone and derivatives thereof [e.g., diflucortolone valerate], fluprednidene and derivatives thereof [e.g., fluprednidene acetate], fluticasone and derivatives thereof [e.g., fluticasone propionate], halobetasol [ulobetasol] and derivatives thereof [e.g., halobetasol proprionate], halometasone and derivatives thereof [e.g., halometasone acetate], and mometasone and derivatives thereof [e.g., mometasone furoate]), acetonides and related substances (e.g., amcinonide, budesonide, ciclesonide, desonide, fluocinonide, fluocinolone acetonide, flurandrenolide [flurandrenolone or fludroxycortide], halcinonide, triamcinolone acetonide and triamcinolone alcohol), carbonates (e.g., prednicarbate), and analogs, derivatives and salts thereof.

In additional embodiments, one or more compounds of structural Formula (I) are used in conjunction with one or more antifibrotic agents to treat a fibrotic disorder. In some embodiments, the one or more antifibrotic agents are or include an anti-inflammatory agent or/and an antioxidant (e.g., vitamin E or an analog thereof [e.g., α-tocopherol or trolox], a sulfur-containing antioxidant or an ROS or radical scavenger [e.g., melatonin], or any combination thereof). In certain embodiments, the one or more antifibrotic agents are or include pirfenidone (which among its various antifibrotic and anti-inflammatory properties described herein also reduces fibroblast proliferation) or/and nintedanib (which blocks signaling of fibroblast growth factor receptors [FGFRs], platelet-derived growth factor receptors [PDGFRs] and vascular endothelial growth factor receptors [VEGFRs] involved in fibroblast proliferation, migration and transformation).

In further embodiments, the one or more antifibrotic agents are or include one or more agents that have anti-hyperglycemic or/and insulin-sensitizing activity for treatment of a fibrotic disorder in which hyperglycemia, diabetes or insulin resistance contributes to development of fibrosis. Examples of such a disorder include diabetic nephropathy, which is characterized by renal fibrosis, and NASH and cirrhosis, both of which are characterized by hepatic fibrosis. Use of anti-hyperglycemic or/and insulin-sensitizing agent (s) can curtail or prevent, e.g., renal inflammation and fibrosis or hepatic inflammation and fibrosis. In certain embodiments, the one or more antifibrotic agents are or include a PPAR-γ agonist (e.g., a thiazolidinedione [supra], such as pioglitazone or rosiglitazone). PPARγ-activating thiazolidinediones have both anti-hyperglycemic and insulin-sensitizing properties.

Antifibrotic agents include without limitation: inhibitors of collagen accumulation, including protein kinase C (PKC) inhibitors (supra, inhibit collagen production), colchicine and its metabolite colchiceine (both inhibit collagen synthesis and deposition), dilinoleoyl-phosphatidylcholine (inhibits collagen production induced by transforming growth factor-beta1 [TGF-β1]), luteolin (reduces fibrosis in part by increasing expression of matrix metalloproteinase 9 [MMP-9] and metallothionein, which degrade the extracellular matrix [ECM]), malotilate (reduces procollagen I α2 [Col1a2] expression), melatonin (inhibits expression of procollagens I and III), S-nitroso-N-acetyl-L-cysteine (reduces collagen I amount in part by activating MMP-13 and suppressing tissue inhibitor of metalloproteinases 2 [TIMP-2]), oxymatrine {reduces procollagen I α1 (Col1a1) (and α-smooth muscle actin [α-SMA]) expression}, pioglitazone (reduces collagen I [and α-SMA] production), pirfenidone (reduces production of procollagens I and II and inhibits TGF-β-stimulated collagen production), quercetin (reduces Col1a1 and procollagen III α1 [Col3a1] expression), resveratrol (reduces collagen I [and α-SMA] production), RGD mimetics and analogs (infra, reduce collagen I accumulation in part by increasing secretion of collagenases), safironil (reduces collagen I [and α-SMA] production), statins (e.g., atorvastatin, lovastatin and simvastatin [all three reduce collagen production]), tranilast (inhibits procollagen expression and fibroblast proliferation), valproic acid (reduces collagen deposition), inhibitors of collagen cross-linking {e.g., D-penicillamine and lysyl oxidase-like 2 (LOXL2, which promotes collagen cross-linking) inhibitors (e.g., β-aminopropionitrile and anti-LOXL2 antibodies [e.g., simtuzumab and AB-0023])}, procollagen-proline dioxygenase (or prolyl 4-hydroxylase, which forms more stable hydroxylated collagen) inhibitors (e.g., malotilate, HOE-077, 5-0885 and S-4682), and procollagen glucosyltransferase (or galactosylhydroxylysine glucosyltransferase, which is important for collagen fibril formation) inhibitors (e.g., malotilate); inhibitors of pro-fibrotic growth factors (e.g., transforming growth factor-beta [including TGF-β1], connective tissue growth factor [CTGF] and platelet-derived growth factor [including PDGF-B, PDGF-C and PDGF-D]) or their production, activation or signaling, including TGF-β inhibitors {e.g., anti-TGF-β antibodies (e.g., fresolimumab [GC1008] and CAT-192) and soluble TGF-β receptors (e.g., sTGFPR1, sTGFPR2 and sTGFPR3)}, TGFPR antagonists {e.g., TGFPR1 (ALK5) antagonists (e.g., galunisertib [LY-2157299], EW-7197, GW-788388, LY-2109761, SB-431542, SB-525334, SKI-2162, SM-16, and inhibitory Smads [e.g., Smad6 and Smad7])}, anti-CTGF antibodies (e.g., FG-3019), PDGF inhibitors (e.g., squalamine, PP1, anti-PDGF aptamers [e.g., E10030], anti-PDGF antibodies [e.g., those targeting PDGF-B, PDGF-C and PDGF-D], and soluble PDGF receptors [e.g., sPDGFRα and sPDGFRβ]), PDGFR (e.g., PDGFRα or/and PDGFRβ) antagonists (e.g., anti-PDGFR antibodies [e.g., REGN2176-3]), bone morphogenic protein-7 (BMP-7) (directly antagonizes TGF-β1 signaling and Smad3 activation, and promotes mesenchymal-to-epithelial transition), N-acetyl-L-cysteine (inhibits TGF-β expression and activation by monomerization of the biologically active TGF-β dimer), S-nitroso-N-acetyl-L-cysteine (suppresses TGF-β1), L-carnitine (reduces PDGF-B expression), epigallocatechin-3-gallate (suppresses activation of Smad2 and Smad3 [and Akt]), galectin-7 (binds to and inhibits phosphorylated Smad2 and Smad3), Leu-Ser-Lys-Leu (SEQ ID NO: 3) (inhibits TGF-β1 activation), α-lipoic acid (inhibits TGF-β signaling via inhibition of Smad3 and AP-1), luteolin (inhibits TGF-β and PDGF signaling), melatonin (inhibits TGF-β and CTGF expression and Smad3 activation), naringenin (suppresses Smad3 expression and activation), niacin (reduces TGF-β expression), pirfenidone (reduces TGF-β production), quercetin (reduces expression of TGF-β1, CTGF, PDGF-B and Smad3), resveratrol (suppresses TGF-β expression), simvastatin (reduces TGF-β1 [and α-SMA] expression), taurine (reduces TGF-β1 [and α-SMA] expression), tranilast (inhibits TGF-β1 expression), vitamin E and analogs thereof (e.g., α-tocopherol and trolox, both of which suppress TGF-β expression), and $α_vβ_6$ integrin (which activates TGF-β1) inhibitors (e.g., anti-$α_vβ_6$ antibodies such as STX-100); receptor tyrosine kinase (TK) inhibitors, including epidermal growth factor receptor (EGFR) TK inhibitors (e.g., afatinib, brigatinib, erlotinib, gefitinib, icotinib, lapatinib, osimertinib and isoflavones [e.g., genistein]), PDGFR TK inhibitors (e.g., crenolanib, imatinib and AG-1295), dual FGFR/VEGFR TK inhibitors (e.g., brivanib and brivanib alaninate), dual PDGFR/VEGFR TK inhibitors (e.g., axitinib, sorafenib, sunitinib, vatalanib and X-82), and triple FGFR/PDGFR/VEGFR TK inhibitors (e.g., nintedanib and pazopanib); anti-EGFR antibodies, such as cetuximab, matuzumab, nimotuzumab, panitumumab and zalutumumab; anti-inflammatory agents, including those listed above, such as anti-inflammatory cytokines (e.g., IL-10), inhibitors of pro-inflammatory cytokines or their receptors or their production (e.g., TNF-α [e.g., an anti-TNF-α antibody such as infliximab or an immunomodulator such as pentoxifylline], IL-10, IL-6 and MCP-1), colchicine, curcuminoids (e.g., curcumin), malotilate, nintedanib, pirfenidone and tranilast; antioxidants, including those listed above, such as vitamins and analogs thereof (e.g., vitamin E and analogs thereof such as α-tocopherol and trolox), sulfur-containing antioxidants (e.g., glutathione, NAC, SNAC, SAC [also suppresses α-SMA expression] and SAM), ROS and radical scavengers (e.g., melatonin and glutathione), Nrf2 activators {e.g., fumarates (e.g., dimethyl and monomethyl fumarate), trichostatin A, and triterpenoids (e.g., oleanolic acid analogs [supra, such as TP-225])}, and omega-3 fatty acids and esters thereof (e.g., Lovaza fish oil); antagonists of the renin-angiotensin-aldosterone system (RAAS), including those listed above, such as renin inhibitors (e.g., aliskiren [reduces hepatic steatosis, oxidative stress, inflammation and fibrosis]), ACE inhibitors (e.g., captopril [inhibits fibroblast proliferation and reduces fibrotic lung response] and perindopril [inhibits liver fibrosis]), and angiotensin II receptor type 1 ($AT_1$) antagonists (e.g., candesartan [inhibits liver fibrosis], irbesartan and losartan) (activation of $AT_1$ by angiotensin II activates PLC, leading to increased cytosolic $Ca^{2+}$ concentration and hence PKC stimulation, also activates tyrosine kinases and promotes ECM formation); inhibitors of the accumulation or effects of advanced glycation end-products (AGEs, which inter alia increase arterial stiffness and stimulate mesangial matrix expansion), including inhibitors of AGE formation (e.g., aminoguanidine, aspirin, benfotiamine, carnosine, α-lipoic acid, metformin, pentoxifylline, pimagedine, pioglitazone, pyridoxamine, taurine and vitamin C), cleavers of AGE crosslinks (e.g., aminoguanidine, N-phenacylthiazolium bromide, rosmarinic acid, alagebrium [ALT-711], ALT-462, ALT-486 and ALT-946), and inhibitors of AGE effects (e.g., natural phenols such as curcumin and resveratrol); other kinds of antifibrotic agents, including RGD mimetics and analogs (inhibit adhesion of fibroblasts and immune cells to ECM glycoproteins) (e.g., NS-11, SF-6,5 and GRGDS), galectin-3 (which is critical for liver fibrosis) inhibitors (e.g., GM-CT-01 and GR-MD-02), marinobufagenin inhibitors (e.g., resibufogenin, spironolactone and canrenone), trichostatin A (inhibits TGFβ1-induced epithelial-to-mesenchymal transition), and PPAR-7 agonists (e.g., thiazolidinediones [supra]); and analogs, derivatives, fragments and salts thereof.

Non-alcoholic fatty liver disease (NAFLD), the most common liver disorder in developed countries, is characterized by fatty liver that occurs when fat, in particular free fatty acids and triglycerides, accumulates in the liver cells (hepatic steatosis) due to causes other than excessive alcohol consumption, such as nutrient overload, high caloric intake and metabolic dysfunction (e.g., hyperlipidemia and impaired glucose control). A liver can remain fatty without disturbing liver function, but a fatty liver can progress to become non-alcoholic steatohepatitis (NASH), a condition in which steatosis is accompanied by inflammation, hepatocyte ballooning and cell injury with or without fibrosis of the liver. Fibrosis is the strongest predictor of mortality from NASH. NASH is the most extreme form of NAFLD. NASH is a progressive disease, with about 20% of patients developing cirrhosis of the liver and about 10% dying from a liver disease, such as cirrhosis or a liver cancer (e.g., hepatocellular carcinoma).

NAFLD, including NASH, is associated with obesity, metabolic syndrome and insulin resistance. For instance, insulin resistance contributes to progression of fatty liver to hepatic inflammation and fibrosis and thus NASH. Furthermore, obesity drives and exacerbates NASH, and weight loss can alleviate NASH.

In some embodiments, one or more compounds of structural Formula (I) are used in combination with one or more additional therapeutic agents to treat NAFLD, such as NASH. In some embodiments, the one or more additional therapeutic agents are selected from antidiabetic agents, anti-obesity agents, anti-inflammatory agents, antifibrotic agents, antioxidants, and combinations thereof.

Therapeutic agents that can be used to treat NAFLD (e.g., NASH) include without limitation: PPAR agonists, including PPAR-6 agonists (e.g., MBX-8025, elafibranor [dual PPAR-α/δ agonist], lanifibranor [triple PPAR-α/δ/γ agonist] and GW501516 [dual PPAR-β/δ agonist]) and PPAR-γ agonists (e.g., thiazolidinediones such as pioglitazone and rosiglitazone, and saroglitazar [dual PPAR-α/γ agonist])— PPAR-δ and -γ agonism increases insulin sensitivity, PPAR-α agonism reduces liver steatosis and PPAR-δ agonism inhibits activation of macrophages and Kupffer cells; GLP-1R agonists (e.g., exenatide, liraglutide and semaglutide), dual GLP-1R/GCGR agonists (e.g., MEDI0382 and SP-1373) and dual GLP-1R/GIPR agonists—such agonists reduce liver steatosis, inflammation and fibrosis; farnesoid X receptor (FXR) agonists, such as obeticholic acid, EDP-305, GS-9674, LJN452 and TERN-101—FXR agonists reduce liver gluconeogenesis, lipogenesis, steatosis and fibrosis; thyroid hormone receptor-beta agonists, such as MGL-3196 and VK2809—THR-β agonists reduce liver steatosis; fibroblast growth factor 19 (FGF19) and analogs and derivatives thereof, such as NGM-282—FGF19 analogs reduce liver gluconeogenesis and steatosis; fibroblast growth factor 21 (FGF21) and analogs and derivatives thereof, such as BMS-986036 and PF-05231023—FGF21 analogs reduce liver steatosis, cell injury and fibrosis; HMG-CoA reductase inhibitors, including statins (e.g., atorvastatin, pitavastatin and rosuvastatin)—statins reduce steatohepatitis and fibrosis; ACC inhibitors, such as NDI-010976 (liver-targeted) and GS-0976—ACC inhibitors reduce de novo lipogenesis and liver steatosis; SCD-1 inhibitors, such as aramchol—SCD-1 inhibitors reduce liver steatosis and increase insulin sensitivity; ATP citrate lyase inhibitors, such as bempedoic acid—ACL inhibitors reduce liver steatosis; ketohexokinase inhibitors, such as PF-06835919—KHK inhibitors reduce liver lipogenesis and inflammation; SGLT2 inhibitors, such as canagliflozin, dapagliflozin, empagliflozin, ipragliflozin and luseogliflozin—SGLT2 inhibitors reduce body weight, liver ALT level and fibrosis; vascular adhesion protein-1 (VAP-1) inhibitors, such as N-[4-(2-{4-[(2-amino-1H-imidazol-4-yl)methyl]phenyl}ethyl)thiazol-2-yl]acetamide hydrochloride, 2-bromoethylamine, semicarbazide, ASP8232, BI-1467335 (PXS-4728A), PXS-4681A, PRX-167700 and TERN-201—VAP-1 inhibitors increase insulin sensitivity and reduce liver inflammation and fibrosis; antagonists of CCR2 or/and CCR5, such as cenicriviroc—antagonists of CCR2 (binds to CCL2 [MCP1]) and CCR5 (binds to CCL5 [RANTES]) inhibit activation and migration of inflammatory cells (e.g., macrophages) to the liver and reduce liver fibrosis; apoptosis inhibitors, including apoptosis signal-regulating kinase 1 (ASK1) inhibitors (e.g., selonsertib) and caspase inhibitors (e.g., emricasan [pan-caspase inhibitor])—apoptosis inhibitors reduce liver steatosis and fibrosis; TGF-β inhibitors (e.g., fresolimumab) and TGF-βR antagonists (e.g., galunisertib)—they reduce liver fibrosis; lysyl oxidase-like 2 (LOXL2) inhibitors, such as simtuzumab—LOXL2 is a key matrix enzyme in collagen formation and is highly expressed in the liver; galectin-3 inhibitors, such as GR-MD-02 and TD139—galectin-3 is critical for development of liver fibrosis; inhibitors of lysophosphatidic acid (LPA) or receptors therefor (e.g., LPAR1) or the production thereof, such as autotaxin inhibitors (e.g., GLPG1690, HA-130, ONO-8430506, PF-8380, S-32826) and anti-autotaxin DNA aptamers (e.g., RB011 and RB014)—such inhibitors inhibit myofibroblast proliferation and hence liver fibrosis; antioxidants, including vitamin E (e.g., α-tocopherol) and scavengers of ROS and free radicals (e.g., cysteamine, glutathione, melatonin and pentoxifylline [also anti-inflammatory via inhibition of TNF-α and phosphodiesterases])—vitamin E reduces liver steatosis, hepatocyte ballooning and lobular inflammation; and analogs, derivatives and salts thereof. Other NASH compounds include LXR inverse agonists, ACMSD inhibitors, VAP1 inhibitors, BAT inhibitors, DGAT inhibitors, ACC2 inhibitors, HSD17b13 inhibitors (roal and siRNA), PNPLA3 siRNA, THRb agonists (remetirom, TERN, Viking), FGF21 (Efruxfermin, Pegozafermin), TLC-3595 (ACC2 inhibitor), mitochondrial protonophores (TLC-6740, Rivus HU6, TLC-1235, siRNA for NASH—(e.g., PNPLA3, HSD17B13, GPAM, mARCI and CIDEB) and mitochondrial uncouplers. Liver failure agents include Terlipressin, Octreotide and Tolvaptan.

In some embodiments, the one or more additional therapeutic agents for treatment of NAFLD (e.g., NASH) are or include a PPAR agonist (e.g., a PPAR-S agonist such as elafibranor or/and a PPAR-7 agonist such as pioglitazone), a HMG-CoA reductase inhibitor (e.g., a statin such as rosuvastatin), an FXR agonist (e.g., obeticholic acid) or an antioxidant (e.g., vitamin E), or any combination thereof. In certain embodiments, the one or more additional therapeutic agents for treatment of NAFLD (e.g., NASH) are or include vitamin E or/and pioglitazone.

In other embodiments, one or more compound of structural Formula (I) are used in combination with one or more anticancer agents to treat a tumor (benign or malignant) or a cancer. For brevity, the term "anticancer agents" as used herein encompasses antitumor agents. In some embodiments, the one or more anticancer agents are or include radiation therapy, chemotherapy or cancer immunotherapy, or any combination or all thereof.

In some embodiments, the chemotherapeutic agent is or includes a PARP inhibitor, a TGF-β inhibitor or a cytotoxic agent, or any combination or all thereof. Examples of PARP inhibitors are described above. In certain embodiments, the PARP inhibitor is olaparib.

Transforming growth factor-beta (TGF-β) is a cytokine that promotes the growth of pre-cancer and cancer cells, angiogenesis and invasion of cancer cells. TGF-β also converts effector T-cells, which normally attack cancer cells with an inflammatory (immune) reaction, into regulatory T-cells that suppress the immune reaction. An increase in TGF-β expression often correlates with the malignancy of many cancers. Therefore, inhibitors of TGF-β or the production, activation or signaling thereof can be used to treat tumors and cancers. Since TGF-β (including TGF-β1) is also a major driver of collagen production and fibrosis, inhibitors of TGF-β or the production, activation or signaling thereof are listed among antifibrotic agents above.

Anticancer cytotoxic agents include without limitation: alkylating agents, including aziridines (e.g., diaziquone, mytomycin and thiotepa), nitrogen mustards (e.g., mannomustine, mustine [mechlorethamine or chlormethine], aniline mustard, bendamustine, benzoic acid mustard, chlorambucil, C6-galactose mustard, melphalan, ossichlorin [nitromin], prednimustine, uramustine, nitrogen mustard carbamates [e.g., estramustine], and oxazaphosphorines [e.g., cyclophosphamide, ifosfamide, mafosfamide, and trofosfamide]), nitrosoureas (e.g., carmustine, fotemustine, lomustine, nimustine, N-nitroso-N-methylurea, ranimustine, semustine and streptozotocin), platinum-containing compounds (e.g., cisplatin, carboplatin and oxaliplatin), alkylsulfonates (e.g., busulfan, mannosulfan and treosulfan), hydrazines (e.g., dacarbazine and procarbazine), imidazotetrazines (e.g., mitozolomide and temozolomide), and triazines (e.g., hexamethylmelamine [altretamine]); cytotoxic antibiotics, including anthracyclines (e.g., aclarubicin, daunorubicin, doxorubicin, epirubicin, idarubicin, mitoxantrone, pirarubicin and valrubicin), actinomycins (e.g., actinomycin D), bleomycins (e.g., bleomycins $A_2$ and $B_2$), mitomycins (e.g., mitomycin C), and plicamycins; antimetabolites, including antifolates (e.g., aminopterin, methotrexate, pemetrexed and pralatrexate), deoxynucleoside analogs (e.g., 5-azacytidine [azacitidine], 5-aza-2'-deoxycytidine [decitabine], cladribine, clofarabine, cytarabine, decitabine, fludarabine, gemcitabine, nelarabine and pentostatin), fluoropyrimidines (e.g., 5-fluorouracil, capecitabine, 5-fluoro-5'-deoxyuridine [doxifluridine] and trifluridine), and thiopurines (e.g., thioguanine, azathioprine and mercaptopurine); antimicrotubule agents, including dolastatins (e.g., dolastatin 15), epothilones (e.g., epothilones A-F), halichondrins (e.g., halichondrin B) and analogs thereof (e.g., eribulin), maytansine, maytansinoids (e.g., ansamitocin, emtansine, mertansine, ravtansine and soravtansine), taxanes (e.g., paclitaxel, docetaxel and cabazitaxel), *vinca* alkaloids (e.g., vinblastine, vincristine, vindesine, vinflunine and vinorelbine), colchicine, nocodazole, podophyllotoxin and rhizoxin; histone deacetylase inhibitors, including trichostatins (e.g., trichostatin A), romidepsin, panobinostat and vorinostat; kinase inhibitors, including bortezomib, erlotinib, gefitinib, imatinib, vemurafenib, vismodegib, curcumin, cyclocreatine, deguelin, fostriecin, hispidin, staurosporine and derivatives thereof (e.g., midostaurin), and tyrphostins (e.g., tyrphostins AG 34 and AG 879); topoisomerase I inhibitors, including camptothecin, irinotecan and topotecan; topoisomerase II-targeting agents, including topoisomerase II poisons (e.g., etoposide, tafluposide, teniposide, doxorubicin and mitoxantrone) and topoisomerase II inhibitors (e.g., novobiocin, merbarone and aclarubicin); DNA or RNA synthesis inhibitors, including 3-amino-1,2,4-benzotriazine 1,4-dioxide, cytosine β-D-arabinofuranoside, 5,6-dichlorobenzimidazole 1-β-D-ribofuranoside, ganciclovir and hydroxyurea; protein synthesis inhibitors, including homoharringtonine; cell growth and differentiation regulators, including retinoids (e.g., all-trans retinol [vitamin A], 11-cis retinol, all-trans retinal [vitamin A aldehyde], 11-cis retinal, all-trans retinoic acid [tretinoin], 9-cis-retinoic acid [alitretinoin], 11-cis retinoic acid, 13-cis-retinoic acid [isotretinoin], all-trans retinyl esters, etretinate, acitretin, adapalene, bexarotene and tazarotene); cell proliferation inhibitors, including mTOR inhibitors (e.g., everolimus, novolimus, ridaforolimus, sirolimus [rapamycin], temsirolimus, umirolimus [biolimus A9] and zotarolimus), apigenin, cholecalciferol (vitamin $D_3$) and sex hormone-binding globulin; apoptosis inducers, including 17-allylamino-17-demethoxygeldanamycin, melatonin, mevinolin, psoralen, thapsigargin, troglitazone, inhibitors of histone deacetylases (e.g., romidepsin), and RXR agonists (supra, such as retinoids [e.g., bexarotene]); and analogs, derivatives and salts thereof.

Cancer immunotherapeutic agents include agents that block immune checkpoints and agents that stimulate the immune system. In certain embodiments, the cancer immunotherapeutic agent is or includes an anti-PD-1 antibody or an anti-PD-L1 antibody, or/and an anti-CTLA-4 antibody.

Anticancer agents that block immune checkpoints include without limitation: inhibitors of programmed cell death 1 (PD-1) receptor or ligands thereof (e.g., PD-L1 and PD-L2), including anti-PD-1 antibodies (e.g., cemiplimab, nivolumab, pembrolizumab, pidilizumab and MEDI-0680 [AMP-514]), anti-PD-1 fusion proteins (e.g., AMP-224 [containing an F, Ab domain and PD-L2]), anti-PD-L1 antibodies (e.g., avelumab, atezolizumab, durvalumab, and BMS-936559 [MDX-1105]), and small-molecule inhibitors of PD-L1 (e.g., BMS-1001 and BMS-1166); inhibitors of cytotoxic T lymphocyte-associated protein 4 (CTLA-4) receptor or ligands thereof, including anti-CTLA-4 antibodies (e.g., ipilimumab and tremelimumab); inhibitors of killer cell immunoglobulin-like receptors (KIRs) or ligands thereof, including anti-KIR antibodies (e.g., lirilumab); inhibitors of lymphocyte activation gene 3 (LAG-3) receptor or ligands thereof, including anti-LAG-3 antibodies (e.g., BMS-986016 and GSK2831781); inhibitors of T-cell immunoglobulin and mucin domain-containing 3 (TIM-3, also called hepatitis A virus cellular receptor 2 [HAVCR2]), including anti-TIM3 antibodies (e.g., LY3321367, MBG453 and TSR-022); inhibitors of indoleamine 2,3-dioxygenase (IDO or IDO1), including indoximod (1-methyl-D-tryptophan), navoximod, α-methyl-tryptophan, 3-carboline (9H-pyrido[3,4-b]indole or norharmane), epacadostat (INCB024360), BMS-986205, NLG-919, and COX-2 inhibitors (e.g., coxibs [supra], which down-regulate the expression of IDO); and analogs, derivatives, fragments and salts thereof.

Anticancer agents that stimulate the immune system include, but are not limited to: agonists of tumor necrosis factor receptor superfamily member 4 (TNFRSF4, OX40 or CD134), including OX40-targeting antibodies (e.g., MEDI-6469 and 9B12) and ligands for OX40 (e.g., OX40L); agonists of TNFRSF member 5 (TNFRSF5 or CD40), including CD40-targeting antibodies (e.g., dacetuzumab and CP-870,893) and ligands for CD40 (e.g., CD40L [CD154]); agonists of TNFRSF member 9 (TNFRSF9, 4-1BB or CD137), including 4-1BB-targeting antibodies (e.g., urelumab and PF-05082566) and ligands for 4-1BB (e.g., 4-1BBL); agonists of TNFRSF member 18 (TNFRSF18, glucocorticoid-induced TNFR-related protein [GITR] or CD357), including GITR-targeting antibodies (e.g., DTA-1 and TRX518) and ligands for GITR (e.g., GITRL); agonists of toll-like receptors (TLRs), including ligands for TLR9 (e.g., unmethylated CpG oligodeoxynucleotides [CpG ODNs], such as agatolimod); cytokines and hormones that stimulate immune cells, including IL-6 and epinephrine (stimulator of, e.g., natural killer cells); and analogs, derivatives, fragments and salts thereof.

Angiogenesis is important for the transition of a benign tumor to a malignant tumor (i.e., a cancer), and for metastasis of a cancer. Thus, anticancer agents include angiogenesis inhibitors. Angiogenesis inhibitors include without limitation inhibitors of vascular endothelial growth factors (VEGFs) {e.g., squalamine, ACU-6151, LHA-510, PAN-90806, decorin, anti-VEGF antibodies and fragments thereof (e.g., bevacizumab, ranibizumab, brolucizumab, ENV1305, ESBA903 and ESBA1008), anti-VEGF immunoconjugates (e.g., KSI-301), anti-VEGF aptamers (e.g., pegaptanib), anti-VEGF designed ankyrin repeat proteins (DARPins) (e.g., abicipar pegol), soluble VEGFRs (e.g., sVEGFR1), and soluble fusion proteins containing one or more extracellular domains of one or more VEGFRs (e.g., VEGFR1, VEGFR2 and VEGFR3) (e.g., aflibercept, conbercept and OPT-302)}, inhibitors of receptors for VEGFs (e.g., VEGFR1 and VEGFR2) (e.g., axitinib, fruquintinib, pazopanib, regorafenib, sorafenib, sunitinib, tivozanib, isoxanthohumol, pristimerin, KPI-285, PF-337210, PP1, TG100572, X-82, D-(LPR), decorin, and anti-VEGFR antibodies and fragments thereof [e.g., ramucirumab]), inhibitors of platelet-derived growth factors (PDGFs) {e.g., squalamine, PP1, decorin, anti-PDGF aptamers (e.g., E10030 and pegpleranib), anti-PDGF antibodies and fragments thereof (e.g., rinucumab), and soluble PDGFRs} or receptors therefor (PDGFRs) (e.g., axitinib, imatinib, nilotinib, pazopanib, sorafenib, sunitinib, X-82, and anti-PDGFR antibodies and fragments thereof [e.g., REGN2176-3]), inhibitors of fibroblast growth factors (FGFs) (e.g., squalamine, decorin, anti-FGF antibodies and fragments thereof, anti-FGF aptamers and soluble FGFRs) or receptors therefor (FGFRs) (e.g., erdafitinib, pazopanib and anti-FGFR antibodies and fragments thereof), inhibitors of angiopoietins (e.g., decorin, anti-angiopoietin antibodies and fragments thereof such as nesvacumab and REGN910-3, and soluble angiopoietin receptors) or receptors therefor (e.g, antibodies and fragments thereof against angiopoietin receptors), bispecific anti-VEGF/anti-angiopoietin antibodies and fragments thereof (e.g., anti-VEGF/anti-angiopoietin-2 antibodies such as ABP-201 and RG7716), inhibitors of integrins (e.g., ALG-1001, JSM-6427, SF0166, and anti-integrin antibodies and fragments thereof), tissue factor (TF) inhibitors (e.g., anti-TF antibodies and fragments thereof and fusion proteins thereof [e.g., ICON-1]), kallikrein inhibitors (e.g., avoralstat, ecallantide, BCX7353, KVD001, and anti-kallikrein antibodies and fragments thereof [e.g., DX-2930]), serine/arginine-protein kinase 1 (SRPK1) inhibitors (e.g., SPHINX31), Src kinase inhibitors (e.g., SKI-606 and TG100572), anecortave (anecortave acetate), angiostatin (e.g., angiostatin K1-3), $av3_3$ inhibitors (e.g., etaracizumab), apoA-I mimetics (e.g., L-4F and L-5F), apoE mimetics (e.g., apoEdp), azurin(50-77) (p28), berberine, bleomycins, borrelidin, carboxyamidotriazole, cartilage-derived angiogenesis inhibitors (e.g., chondromodulin I and troponin I), castanospermine, CM101, corticosteroids (including glucocorticoids), cyclopropene fatty acids (e.g., sterculic acid), α-difluoromethylornithine, endostatin, everolimus, fumagillin, genistein, heparin, interferon-α, interleukin-12, interleukin-18, itraconazole, KV11, linomide, 2-methoxyestradiol, pigment epithelium-derived factor (PEDF), platelet factor-4, PPAR-α agonists (e.g., fibrates), PPAR-7 agonists (e.g., thiazolidinediones), prolactin, rapamycin (sirolimus), sphingosine-1-phosphate inhibitors (e.g., sonepcizumab), squalene, staurosporine, angiostatic steroids (e.g., tetrahydrocortisol) plus heparin, stilbenoids, suramin, SU5416, tasquinimod, tecogalan, tetrathiomolybdate, thalidomide and derivatives thereof (e.g., lenalidomide and pomalidomide), thiabendazole, thrombospondins (e.g., thrombospondin 1), TNP-470, tranilast, triterpenoids (e.g., oleanolic acid analogs [supra] such as TP-225), (+)-TBE-B, tumstatin and fusion proteins thereof (e.g., OCU200), vasostatin, vasostatin 48, Withaferin A, and analogs, derivatives, fragments and salts thereof.

Other kinds of anticancer agents include, but are not limited to: drug-efflux pump inhibitors, including P-glycoprotein inhibitors (e.g., mifepristone and verapamil); cell adhesion inhibitors, such as cimetidine; Golgi apparatus disruptors, such as brefeldins (e.g., brefeldin A); ionizing radiation, such as X-ray; radiopharmaceuticals, such as $^{131}$I-iodide, $^{131}$I-MIBG (m-iodobenzylguanidine), $^{223}$Ra-dichloride, $^{153}$Sm-EDTMP (ethylenediaminotetramethylenephosphoric acid), and $^{89}$Sr-chloride; sensitizers of cancer cells to radiation, including PARP inhibitors (infra), berberine and indomethacin; enhancers of cell survival after treatment with cytotoxic drugs or radiation, such as pifithrin-α; vaccines, including those that stimulate the immune system to recognize proteins produced by tumor/cancer cells and thereby to attack tumor/cancer cells; and analogs, derivatives and salts thereof.

Compounds of structural Formula (I) can enhance the immune response to an acute or chronic viral, bacterial or fungal infection when used in conjunction with an antiviral, antibacterial or antifungal agent. In certain embodiments, the antibiotic is ethionamide and optionally SMARt-420 for treatment of, e.g., tuberculosis. Ethionamide has antibiotic properties against mycobacteria such as M. tuberculosis. SMARt-420 reverses resistance of, e.g., M. tuberculosis to ethionamide and increases the bacteria's sensitivity to ethionamide.

Compounds of structural Formula (I) can also enhance and direct the adaptive immune response to a vaccine antigen, thereby improving the effectiveness of the vaccine. A compound of structural Formula (I) can be utilized as a component of a vaccine adjuvant. In certain embodiments, a compound of structural Formula (I) is administered in combination with a vaccine to a subject in order to enhance the effectiveness of the vaccine.

When activated by DNA damage, poly(ADP-ribose) polymerase (PARP) recruits other proteins that repair single-stranded DNA breaks ("nicks"). PARP activity is necessary for repair of DNA nicks. PARP expression and activity are upregulated under diverse conditions that lead to DNA damage and ultimately cell injury or cell death, including hypoxia. However, PARP is a major consumer of $NAD^+$ in the cell, and markedly increased PARP activity can deplete $NAD^+$ and cause profound mitochondrial and cellular dysfunction. Therefore, PARP inhibition can increase $NAD^+$ level (e.g., in mitochondria, the cytosol or/and the nucleus, such as total cellular $NAD^+$ level) and thereby can enhance mitochondrial function (e.g., oxidative metabolism), mitochondrial biogenesis and cellular function (e.g., increase the activity of sirtuins such as SIRT1 and SIRT3).

PARP inhibitors are currently approved as antitumor/anticancer agents. DNA damage occurs countless times during each cell cycle, and failure to repair damaged DNA leads to the death of tumor/cancer cells. Some PARP inhibitors mainly block PARP enzyme activity and do not trap PARP on DNA, while other PARP inhibitors both block PARP enzyme activity and act as PARP poison. In the latter case, PARP bound to a PARP inhibitor becomes trapped at the site of a DNA nick, and such a trapped PARP-DNA complex (PARP poison) is more toxic to cells than the unrepaired single-strand DNA breaks that accumulate in the absence of PARP activity because it blocks DNA replication. PARP inhibitors include without limitation niraparib, olaparib, pamiparib (BGB290), rucaparib, talazoparib, veliparib, 4-amino-1,8-naphthalimide, CEP9722, E7016, PJ34, and analogs, derivatives and salts thereof.

Combination of compounds of structural Formula (I) plus olaparib at a dose much lower than its chemotherapeutic dose may synergistically increase $NAD^+$ level (e.g., in mitochondria, the cytosol or/and the nucleus, such as total cellular $NAD^+$ level) and provide cytoprotection (reduces cytotoxicity) under DNA damage-inducing conditions. Without intending to be bound by theory, low-level PARP inhibition by a PARP inhibitor (e.g., olaparib) at a low dose can reduce the rate of $NAD^+$ consumption by PARP, increase NAD level and hence enhance mitochondrial and cellular function and provide cytoprotection. Moreover, low-level PARP inhibition can avoid the trapping of PARP at the site of a DNA nick, thereby allowing the cellular DNA-repair machinery to repair damaged DNA.

In some embodiments, one or more compounds of structural Formula (I) in combination with a PARP inhibitor may increase $NAD^+$ level (e.g., total cellular $NAD^+$ level, such as that in target cells) by at least about 20%, 30%, 50%, 100% (2-fold), 150%, 200% (3-fold), 4-fold, 5-fold, 6-fold, 7-fold, 8-fold, 9-fold or 10-fold in vitro, ex vivo or in vivo. In certain embodiments, one or more compounds of structural Formula (I) in combination with a PARP inhibitor increase $NAD^+$ level (e.g., total cellular $NAD^+$ level, such as that in target cells) by at least about 50%, 100% (2-fold), 3-fold or 5-fold in vitro, ex vivo or in vivo.

In further embodiments, one or more compounds of structural Formula (I) in combination with a PARP inhibitor increase the number of viable cells (e.g., target cells) by at least about 10%, 20%, 30%, 50%, 100% (2-fold), 150%, 200% (3-fold), 4-fold or 5-fold in vitro, ex vivo or in vivo. In certain embodiments, compounds of structural Formula (I) in combination with a PARP inhibitor increase the number of viable cells (e.g., target cells) by at least about 20%, 50%, 100% or 200% in vitro, ex vivo or in vivo.

In some embodiments, compounds of structural Formula (I) are used in combination with a PARP inhibitor at a dose significantly lower than its recommended dose as an antitumor/anticancer agent to treat a non-tumor/non-cancer disease/disorder or condition disclosed herein, or to bring about a biological effect disclosed herein (e.g., increase NAD$^+$ level or/and provide cytoprotection). The PARP inhibitor can inhibit one or more members of the PARP family, such as PARP-1 or/and PARP-2. In certain embodiments, the PARP inhibitor is a selective or non-selective inhibitor of PARP-1. The non-tumor/non-cancer disease or condition can be, e.g., any mitochondrial disease, mitochondria-related disease or condition, or disease or condition characterized by acute NAD$^+$ depletion due to DNA damage described herein. In certain embodiments, the disease or condition is a metabolic disorder (e.g., obesity or type 2 diabetes). One or more other therapeutic agents described herein can optionally be used in combination with compounds of structural Formula (I) and a PARP inhibitor. The use of one or more compounds of structural Formula (I) in combination with a PARP inhibitor (e.g., olaparib) at a significantly sub-chemotherapeutic dose can synergistically increase NAD$^+$ level (e.g., in mitochondria, the cytosol or/and the nucleus, such as total cellular NAD$^+$ level) or/and provide cytoprotection (e.g., reduce cell injury, damage or death), or can have a synergistic therapeutic effect.

A PARP inhibitor at a significantly sub-chemotherapeutic dose can be used in combination with one or more compounds of structural Formula (I) to treat any non-tumor/non-cancer disease/disorder or condition associated with DNA damage. The DNA damage can be due to any cause, such as radiation (e.g., UV or an ionizing radiation such as X-ray), a chemical, a chemotherapeutic agent, oxidative stress or hypoxia. The disease/disorder or condition can be acute or chronic and can be associated with NAD$^+$ depletion or/and cell injury, damage, degeneration or death. Such diseases/disorders and conditions include without limitation diseases and conditions characterized by acute NAD$^+$ depletion due to DNA damage and described above. In certain embodiments, the disease/disorder or condition is an acute life-threatening cardiovascular (e.g., myocardial ischemia/infarction/IRI) or cerebrovascular (e.g., cerebral ischemia/infarction/IRI) disorder, or a neurodegenerative disorder.

In some embodiments, the dose of a PARP inhibitor to treat a non-tumor/non-cancer disease/disorder or condition disclosed herein, or to bring about a biological effect disclosed herein, in combination with one or more nicotinyl riboside compounds is no more than about 10%, 5%, 1%, 0.5% or 0.1% of the recommended dose of the PARP inhibitor as an antitumor/anticancer agent. In certain embodiments, the dose of a PARP inhibitor for such a use is no more than about 1% of the recommended dose of the PARP inhibitor as an antitumor/anticancer agent. In some embodiments, the PARP inhibitor is olaparib, and the dose (e.g., per day or per dose) of olaparib to treat a non-tumor/non-cancer disease/disorder or condition disclosed herein, or to bring about a biological effect disclosed herein, in combination with one or more nicotinyl riboside compounds is no more than about 10 mg, 5 mg, 1 mg, 0.5 mg or 0.1 mg; or is from about 0.01 or 0.1 mg to about 10 mg, from about 0.01 or 0.1 mg to about 1 mg, or from about 1 mg to about 10 mg; or is about 0.01-0.1 mg, 0.1-0.5 mg, 0.5-1 mg, 1-5 mg or 5-10 mg; or is about 10 µg, 50 µg, 0.1 mg, 0.5 mg, 1 mg, 5 mg or 10 mg. In certain embodiments, the dose (e.g., per day or per dose) of olaparib for such a use is no more than about 1 mg.

A PARP inhibitor can be administered in any suitable frequency. In certain embodiments, the PARP inhibitor is administered once or twice daily.

The dose or therapeutically effective amount, the frequency of administration and the route of administration of a compound of structural Formula (I) used in conjunction with a low dose of a PARP inhibitor can be, e.g., any dose or therapeutically effective amount, any frequency of administration and any route of administration of the described herein. In some embodiments, the dose of a compound of structural Formula (I) is from about 1, 50 or 100 mg to about 500 or 1000 mg per day, which can be administered (e.g., orally) in a single dose (e.g., N mg once daily) or in divided doses (e.g., N/2 mg twice daily). In certain embodiments, the dose of a compound of structural Formula (I) is about 1-100 mg, 100-500 mg or 500-1000 mg per day, or about 50 mg, 100 mg, 150 mg, 200 mg, 250 mg, 300 mg, 400 mg, 500 mg, 600 mg, 700 mg, 800 mg, 900 mg or 1000 mg per day. In further embodiments, the dose of a compound of structural Formula (I) is about 1-50 mg, 50-100 mg, 100-200 mg, 200-300 mg, 300-400 mg or 400-500 mg per day. In certain embodiments, the dose of a compound of structural Formula (I) is from about 10, 50 or 100 mg to about 200 or 300 mg per day. In some embodiments, a lower dose of a compound of structural Formula (I) is used to treat a less severe non-tumor/non-cancer disease/disorder or condition, while a higher dose of a compound of structural Formula (I) is used to treat a more severe non-tumor/non-cancer disease/disorder or condition.

The synergistic effects of a combination of one or more compound of structural Formula (I) and a low dose of a PARP inhibitor, such as in elevating NAD$^+$ level and enhancing cytoprotection, can be exploited prophylactically to prevent a non-tumor/non-cancer disease/disorder or condition, or potentially to prevent a tumor or cancer. As an example, one or more compounds of structural Formula (I) and a low dose of a PARP inhibitor can be given prior to a surgery to reduce morbidity caused by general anesthesia or hypoxia- or hypotension-induced cytotoxicity. For instance, one or more compound of structural Formula (I) and a low dose of a PARP inhibitor can be given prior to a cardiac procedure (e.g., angioplasty or valvular surgery) to reduce morbidity and mortality due to hypotensive or bleeding episodes. As another example, one or more compound of structural Formula (I) and a low dose of a PARP inhibitor can be applied to the skin to prevent sunlight-induced skin injury.

In some embodiments, the one or more compound of structural Formula (I) or/and the PARP inhibitor are administered as a complex with a dendrimer (e.g., PAMAM) or via a dendrimer-containing composition. The dendrimer can optionally have one or more moieties for targeting to specific organ(s), tissue(s), cell type(s) or organelle(s), such as one or more N-acetylgalactosamine moieties for targeting to the liver for treatment of, e.g., a liver or metabolic disorder.

In other embodiments, one or more compound of structural Formula (I) or/and a PARP inhibitor are utilized in ex vivo therapy, including in any ex vivo therapy described herein. In yet other embodiments, one or more compound of structural Formula (I) and a PARP inhibitor are employed to enhance DNA editing, such as in the use of a CRISPR, transcription activator-like effector nuclease (TALEN) or Arcus nuclease to promote non-homologous end joining (NHEJ) or homology-directed repair (HDR). Low-level PARP inhibition by a low dose of a PARP inhibitor permits repair of single-stranded DNA breaks.

Other synergistic approaches are with ACMSD inhibitors, NR, NMN, NRH, CD38 inhibitors, SARM1 inhibitors, uncouplers and other approaches for lipid/TG lowering.

In other embodiments, one or more compound of structural Formula (I) can be used concomitantly with medications that can cause acute kidney injury (AKI) or prevent worsening of chronic kidney injury. Common medications associated with AKI are antibiotics: aminoglycosides, cephalosporins, amphotericin B, bacitracin, and vancomycin. The entire class of ACE inhibitors, and angiotensin receptor blockers (candesartan and valsartan). Medicines used for cancer chemotherapy: cisplatin, carboplatin, and methotrexate. Dyes (contrast media) used in medical imaging tests—particularly at risk at patients with coronary artery disease or post-CABG where renal function is compromised. The other big class are NSAIDS—ibuprofen, ketoprofen, and naproxen.

In other embodiments, one or more compound of structural Formula (I) can be used concomitantly with medications such as mitochondrial stress response modulators like tetracyclines, including non-microbial compounds like 9 TB to enhance host tolerance—for the prevention and treatment of acute and chronic severe viral infections, bacterial sepsis, and ischemia reperfusion injury states.

In other embodiments, one or more compound of structural Formula (I) can be used concomitantly with medications such SPT1 inhibitors for the treatment of myopathy including inclusion body myositis, sarcopenia, DMD and other genetic etiologies for myopathy.

Finally, it should be noted that there are alternative ways of implementing the present invention. Accordingly, the present embodiments are to be considered as illustrative and not restrictive, and the invention is not to be limited to the details given herein but may be modified within the scope and equivalents of the appended claims.

All publications and patents cited herein are incorporated by reference in their entirety.

The following examples are provided for illustrative purposes only and are not intended to limit the scope of the invention.

EXAMPLES

Abbreviations used in experimental procedures.
Aq. Aqueous
RT Room temperature
MeOH Methanol
THF Tetrahydrofuran
DMF Dimethylformamide
TLC Thin layer chromatography using silica gel plates
EtOAc Ethyl acetate
HCl Hydrochloric acid
TBDMS Tert-Butyldimethylsilyl chloride
TFA Trifluoro acetic acid
Et₃N·3HF Triethylamine trihydrofluoride
DMAP N, N-Dimethyl amino pyridine
Py Pyridine Scheme 1 illustrates the preparation of compounds 100 and 101.

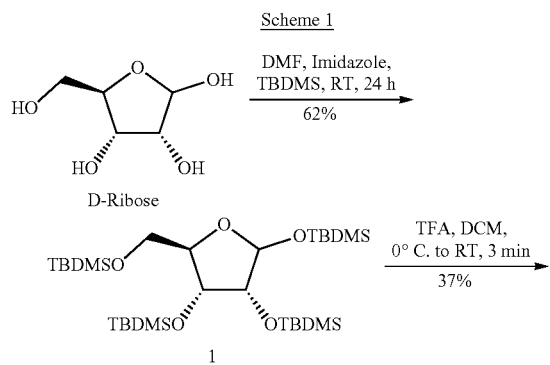

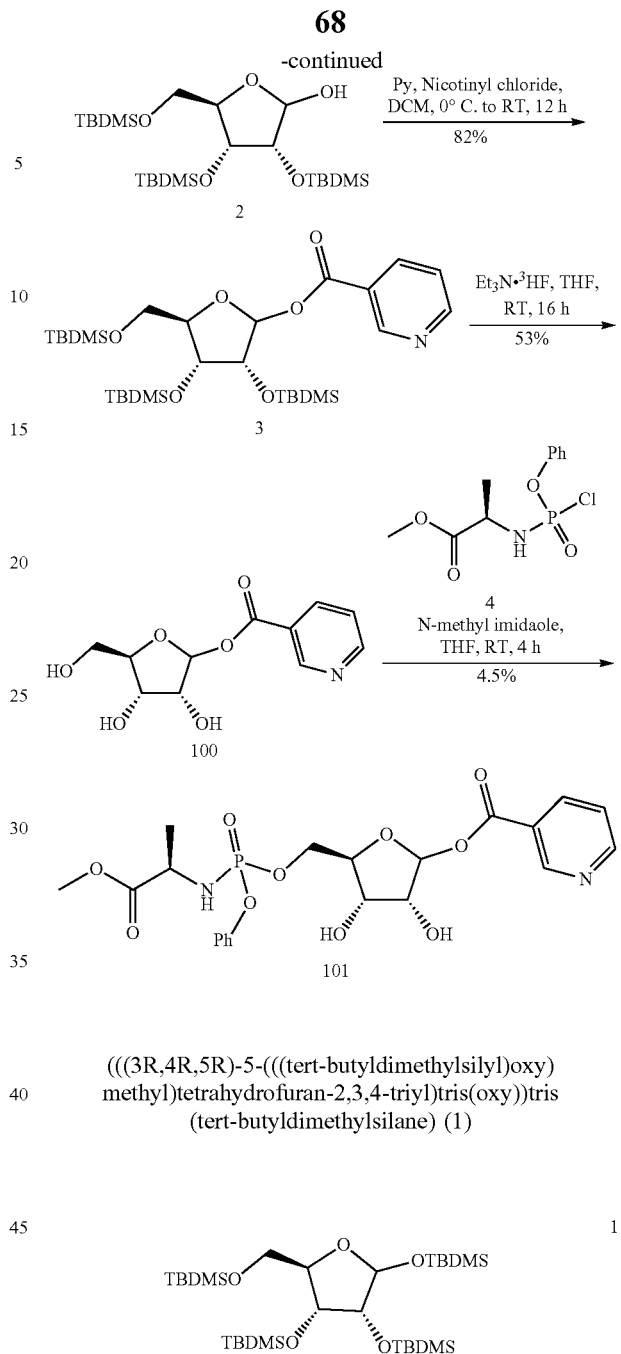

(((3R,4R,5R)-5-(((tert-butyldimethylsilyl)oxy)
methyl)tetrahydrofuran-2,3,4-triyl)tris(oxy))tris
(tert-butyldimethylsilane) (1)

To a stirred solution of ribose (50 g, 0.33 mol) in DMF (120 mL) at 0° C. was added imidazole (90.6 g, 1.33 mol), followed by addition of TBDMSCl (200 g, 1.33 mmol). The resulting mixture was stirred at RT for 24 h. TLC of the reaction mixture showed the complete conversion of starting material and a new non-polar spot was observed. The reaction mixture was quenched with aq. NaHCO₃ solution and extracted with ethyl acetate. The combined organic layers were dried over anhydrous Na₂SO₄, filtered and concentrated under reduced pressure to provide the crude compound. The crude material was purified by column chromatography to afford compound 1 (125 g, 62%) as pale-yellow liquid. ¹H NMR (400 MHz, DMSO): δ 5.09 (d, J=1.6 Hz, 1H), 4.04-4.05 (m, 1H), 3.92-3.91 (m, 1H), 3.73 (d, J=3.2 Hz, 2H), 3.58-3.59 (m, 1H), 0.9 (s, 36H), 0.6 (s, 24H). R$_f$: 0.8. Mobile phase: 5% EA/Hexane.

(3R, 4R, 5R)-3, 4-bis ((tert-butyldimethylsilyl) oxy)-5-(((tert-butyldimethylsilyl) oxy) methyl) tetrahydrofuran-2-ol (2)

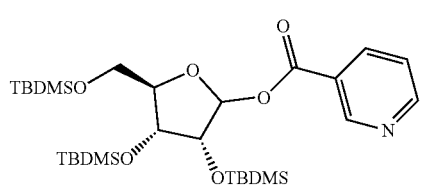

To a stirred solution of compound 1 (150 g, 0.24 mol) in DCM (2.5 L) at 0° C. was added TFA (452 g, 3.4 mol). The resulting mixture was stirred at the same temperature for 2-3 min (Note: Need to quench immediately). After 3 min, the reaction mixture was poured into aq. NaHCO$_3$ solution. The organic layer was separated and dried over anhydrous Na$_2$SO$_4$, filtered and concentrated under reduced pressure to provide crude compound. The crude material was purified by using column chromatography to afford compound 2 (40 g, 33%) as pale-yellow gum. $^1$H NMR (400 MHz, CDCl$_3$): δ 5.011-5.017 (m, 1H), 4.206-4.234 (m, 1H), 4.051-4.062 (m, 3H), 3.65-3.658 (m, 1H), 3.529-3.541 (m, 1H), 0.9 (s, 27H), 0.6 (s, 18H). R$_f$ 0.4 (Mobile phase: 5% EA/hexanes).

(3R, 4R, 5R)-3,4-bis((tert-butyldimethylsilyl)oxy)-5-(((tert-butyldimethylsilyl)oxy)methyl) tetrahydrofuran-2-yl nicotinate (3)

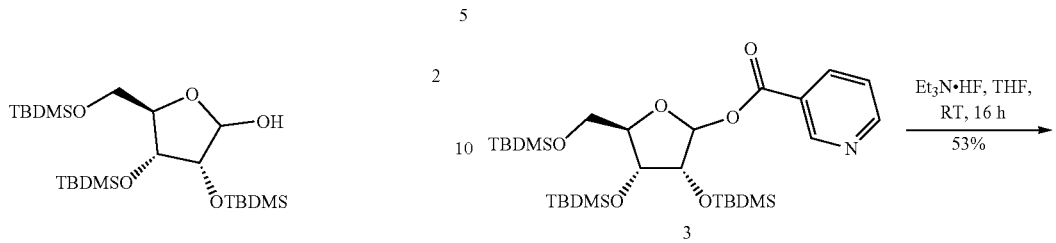

To a stirred solution of compound 2 (80 g, 0.16 mol) in DMF (320 mL) at 0° C. was added a solution of nicotinyl chloride (34 g, 0.19 mol) in pyridine (80 mL) dropwise. The resulting mixture was allowed to stir at RT for 12 h. TLC showed complete conversion of starting material and a new polar spot was observed. The reaction mixture was quenched with aq. NaHCO$_3$ solution and extracted with ethyl acetate. The combined organic layers were washed with 1N HCl (500 mL) and dried over anhydrous Na$_2$SO$_4$, filtered and the filtrate was concentrated under reduced pressure to provide crude compound. The crude material was purified by using column chromatography to afford compound 3 (80 g, 82%) as pale-yellow gummy liquid. $^1$H NMR (400 MHz, CDCl$_3$): δ 9.2 (m, 1H), 8.78 (d, J=1.6 Hz, 1H), 8.27 (t, J=2 Hz, 1H), 7.39 (q, J=4.8 Hz, 1H), 6.14 (d, J=1.2 Hz, 1H), 4.36 (q, J=4.4 Hz, 1H), 4.16 (dd, J=1.2 Hz, 1H), 4.07-4.08 (m, 1H), 3.89 (d, J=2.4 Hz, 1H), 3.69 (d, J=3.2 Hz, 1H), 0.93 (s, 27H), 0.2 (s, 18H). R$_f$ 0.4. Mobile phase: 10% EA/hexanes.

Example 1: (3R, 4S, 5R)-3, 4-dihydroxy-5-(hydroxymethyl) tetrahydrofuran-2-yl nicotinate (100)

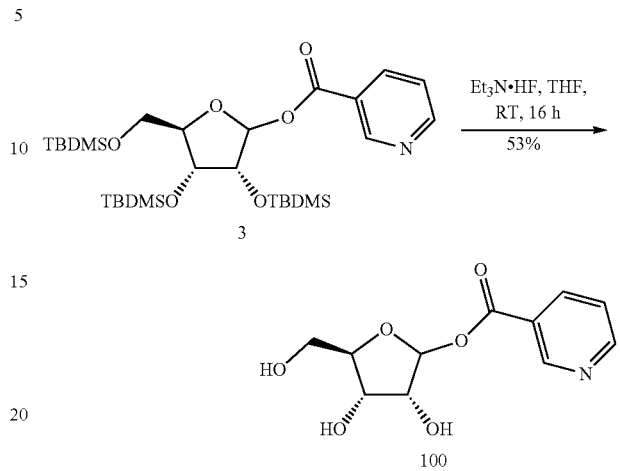

To a stirred solution of compound 3 (40 g, 0.06 mol) in THF (160 mL) at −40° C. was added Et$_3$N·3HF (38 g, 0.2 mol; Spectrochem make; 97% purity). The reaction mixture was allowed to stir at RT for 16 h. The reaction mixture was then cooled to −40° C., the THF layer was removed without any water work up and the gummy compound was washed with diethyl ether (3×100 mL) and purified by column chromatography using 100-200 mesh (neutralized with triethylamine) by eluting with 2-5% methanol in DCM to get off-white sticky solid (9 g, 53%). LCMS showed 80% of desired mass, which was re-purified by RP-C18 to get (4 g, 24%) of compound 100 with 98% purity. $^1$H NMR (400 MHz, CD$_3$OD): δ 9.11 (s, 1H), 8.75 (d, J=1.6 Hz, 1H), 8.40 (m, 1H), 7.58 (d, 1H), 6.24 (s, 1H), 4.35 (q, 1H), 4.18 (d, 1H), 4.04-4.05 (m, 1H), 3.82-3.79 (d, 1H), 3.63 (dd, 1H). LCMS: m/z: 256.11 [M+H]$^+$, 91.49% (0.89 min, 0.76 min). Column: Acquity BEH C18 (2.1×100 mm, 1.7 μm). Mobile Phase: A-0.01% FA in water; B-0.01% FA in ACN, (T/% B: 0.01/10, 0.5/10, 4/90, 8/90). Flow Rate: 0.4 mL/min. R$_f$: 0.4. Mobile phase: 10% MeOH in DCM.

Example 2: (3R, 4S, 5R)-3,4-dihydroxy-5-(((((1-methoxy-1-oxopropan-2-yl)amino)(phenoxy)phosphoryl) oxy)methyl)tetrahydrofuran-2-yl nicotinate (101)

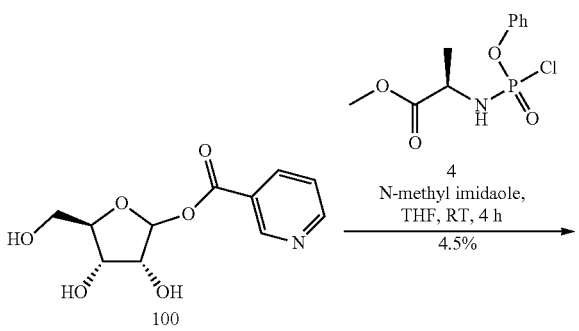

-continued

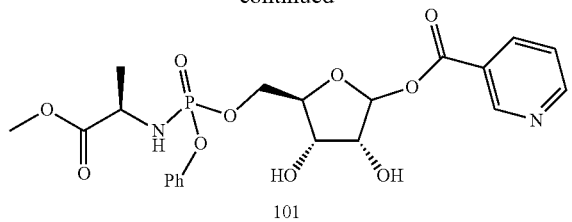

101

To a stirred solution of compound 100 (8 g, 0.03 mol, 80% pure material) in THF (80 mL) at RT was added N-methyl imidazole (12 g, 0.15 mol) dropwise for 5 min. The reaction mixture was stirred for 15 min and then a solution of compound 4 (26 g, 0.09 mol) in THF (20 mL) was added and stirring continued at RT for 12 h. The reaction mixture was directly concentrated under reduced pressure to provide a brown liquid compound, which was washed with diethyl ether (3×100 mL) without any water work up and was purified by column chromatography by eluting with 2-7% methanol in DCM to provide compound 101 (3.2 g) with 55% purity (~1:1 mixture of diastereomers) by LCMS. This material was re-purified by C-18 RP preparative HPLC and the fractions were lyophilized to afford compound 101 (800 mg, ~5%) as off-white gummy solid. $^1$H NMR [400 MHz, CD$_3$OD]: δ 9.11 (dd, 1H), 8.75 (d, J=1.6 Hz, 1H), 8.38 (m, 1H), 7.50 (dd, Hz, 1H), 7.29 (m, 2H), 7.15 (t, 2H), 7.10 (d, 1H) 6.24 (s, 1H), 4.41 (m, 2H), 4.20 (m, 3H), 3.375 (m, 1H), 3.56 (d, 3H), 1.25 (d, 3H). LCMS purity: (44.46% & 48.09% mixture of diastereomers). Column: Acquity Halo C18 (2.1× 100 mm, 2.7 m). Mobile Phase: A-0.1% NH3; B-ACN, (T/% B: 0.01/10, 0.5/10, 5/40, 10/90). FlowRate: 0.4 mL/min. R$_f$: 0.5. Mobile phase: 10% MeOH/DCM.

(2S)-methyl 2-((chloro(phenoxy)phosphoryl)amino) propanoate (4)

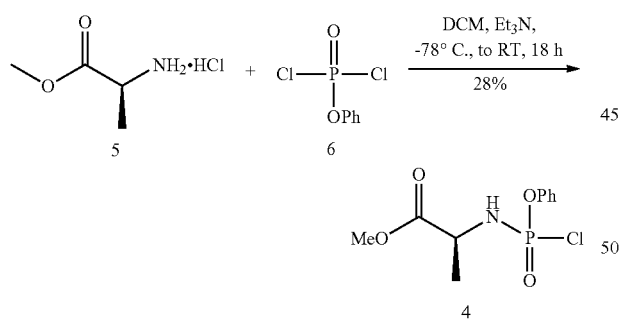

To a stirred solution of compound 5 (60 g, 0.43 mol) and compound 6 (90 g, 0.43 mol) in DCM (200 mL) at −78° C. was added a solution of Et$_3$N (87 g, 0.86 mol) in DCM (100 mL) dropwise. The reaction mixture was allowed to stir at RT for 4 h. TLC showed complete conversion of starting material and a new non-polar spot was observed. The reaction was directly concentrated under reduced pressure to provide a white solid. Diethyl ether was added to the solid compound and the suspension was stirred for 30 min. The solid was removed by filtration and the filtrate was concentrated under reduced pressure to yield the crude compound. The crude material was purified by column chromatography eluting with 10% to 30% ethyl acetate in hexane to afford compound 4 (50 g, 28%) as pale-yellow gum. $^1$H NMR (400 MHz, CDCl$_3$): δ 7.2 (m, 5H), 4.0 (m, 1H), 3.8 (s, 3H), 1.37 (dd, 3H). LCMS: m/z: 260.05 (chloro replaced with hydroxy) [M+H]$^+$, 90% (1.87 min.). Column: Acquity BEH C18 (2.1×100 mm, 1.7 μm). Mobile Phase: A-0.01% FA in water; B-0.01% FA in ACN, (T/% B: 0.01/10, 0.5/10, 4/90, 8/90). Flow Rate: 0.4 mL/min. R$_f$: 0.5. Mobile phase: 40% EA/Hexane.

Scheme 2 illustrates the preparation of compound 102.

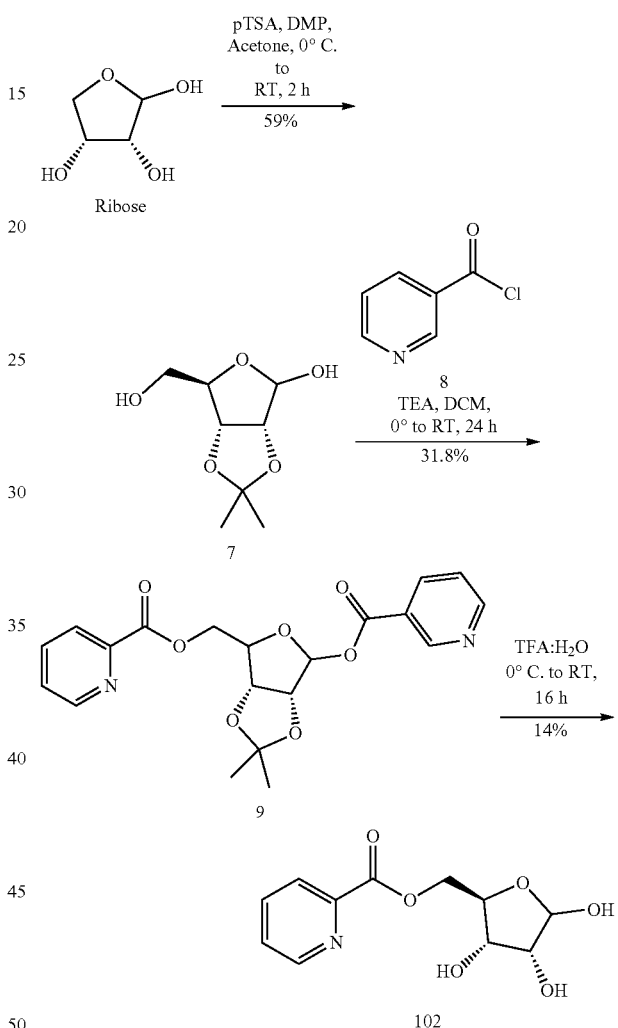

6-(hydroxymethyl)-2,2-dimethyltetrahydrofuro[3,4-d][1,3]dioxol-4-ol (2) (7)

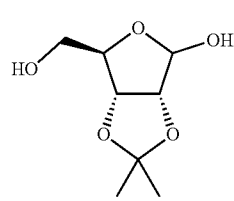

A solution of ribose (10.0 g, 66.6 mmol) in dry acetone (100 mL) was cooled to 0° C. then pTSA was added (80 mg, 2.1 mmol) followed by DMP (9 mL, 73.3 mmol). The resulting mixture was stirred at RT for 2 h. The clear reaction mass was neutralized with anhydrous sodium bicarbonate and filtered through Celite-bed, the filtrate was concentrated under reduced pressure to get crude gummy compound. The crude compound was purified by column chromatography using 100-200 silica gel (eluted in 30% EtOAc: hexanes) to provide compound 2 (7.4 g, 59%) as colorless liquid, product was confirmed by $^1$H NMR. $^1$H NMR (400 MHz, DMSO) δ 6.49 (d, 1H), 5.18 (m, 1H), 4.9 (m, 1H), 4.7 (t, 1H), 4.42 (m, 1H), 4.0 (m, 1H), 3.42 (m, 24=H), 1.38 (m, 3H), 1.28 (s, 3H). $R_f$=0.3 (Mobile phase: 40% EtOAc: Hexane).

(3R, 4R, 5R)-3,4-bis((tert-butyldimethylsilyl)oxy)-5-(((tert-butyldimethylsilyl)oxy)methyl) tetrahydrofuran-2-yl nicotinate (9)

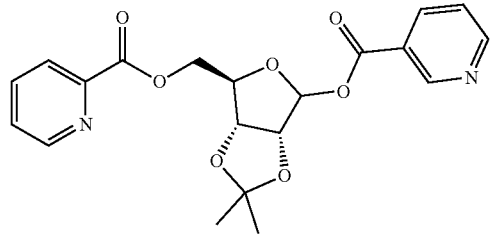

To a stirred solution of compound 7 (80 g, 0.16 mol) in DMF (320 mL) at 0° C. was added a solution of nicotinyl chloride (8) (34 g, 0.19 mol) in pyridine (80 mL) dropwise. The resulting mixture was allowed to stir at RT for 12 h. TLC showed complete conversion of starting material and a new polar spot was observed. The reaction mixture was quenched with aq. NaHCO$_3$ solution and extracted with ethyl acetate. The combined organic layers were washed with 1N HCl (500 mL) and dried over anhydrous Na$_2$SO$_4$, filtered and the filtrate concentrated under reduced pressure to provide crude compound 9. The crude material was purified by using column chromatography to afford compound 9 (80 g, 82%) as pale-yellow gummy liquid. $^1$H NMR [400 MHz, CDCl$_3$]: δ 9.2 (m, 1H), 8.78 (d, J=1.6 Hz, 1H), 8.27 (t, J=2 Hz, 1H), 7.39 (q, J=4.8 Hz, 1H), 6.14 (d, J=1.2 Hz, 1H), 4.36 (q, J=4.4 Hz, 1H), 4.16 (dd, J=1.2 Hz, 1H), 4.07-4.08 (m, 1H), 3.89 (d, J=2.4 Hz, 1H), 3.69 (d, J=3.2 Hz, 1H), 0.93 (s, 27H), 0.2 (s, 18H). $R_f$ 0.4. Mobile phase: 10% EA/hexanes.

Example 3: (3, 4, 5-trihydroxytetrahydrofuran-2-yl) methyl picolinate (102)

Compound 9 (9.0 g, 22.5 mmol) was dissolved in TFA:H$_2$O at 0° C. and then stirred at RT for 16 h. The solvent was evaporated to provide crude product which was purified by column chromatography using 100-200 silica gel (eluted in 5% MeOH: DCM) to provide compound 102 (800 mg, 14%) as a pale-yellow liquid. $^1$H NMR [400 MHz, CDCl$_3$]: δ9.15 (s, 1H), 8.75-8.74 (d, J=1.6 Hz, 1H), 8.49-8.46 (d, 1H), 7.60-7.56 (m, 1H), 5.20 (s, 1H), 4.65 (m, 1H), 4.4 (m, 1H), 4.30 (m, 1H), 4.28 (m, 1H), 4.18-4.15 (m, 1H), 3.85-3.80 (d, 1H). LCMS: m/z: 256.19[M+H]$^+$, 96.65% (8.28 min.). Column: LUNA 5µ C18 (4.6×100 mm). Mobile Phase: A 0.1% TFA in water; B-0.1% TFA in ACN, (T/% B: 0.01/10, 5/10, 20/90, 25/90). Flow Rate: 0.7 mL/min. $R_f$: 0.3 (Mobile phase: 10% MeOH: DCM).

Scheme 3 illustrates the preparation of compounds 103 and 104.

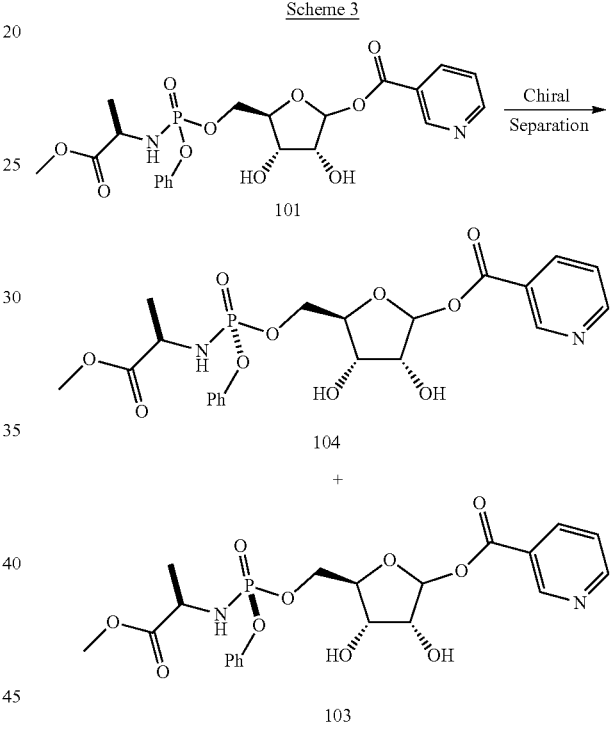

Example 4: (2S,3R,4S,5R)-3,4-dihydroxy-5-(((((S)—(((S)-1-methoxy-1-oxopropan-2-yl)amino)(phenoxy) phosphoryl)oxy)methyl)tetrahydrofuran-2-yl nicotinate (103) and (2S,3R,4S,5R)-3,4-dihydroxy-5-((((R)—(((S)-1-methoxy-1-oxopropan-2-yl)amino) (phenoxy)phosphoryl)oxy)methyl)tetrahydrofuran-2-yl nicotinate (104)

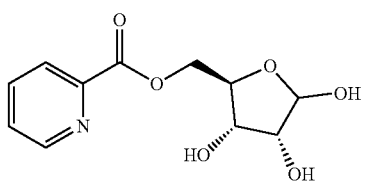 [SMILES: O=C(OC[C@H]1OC(O)[C@H](O)[C@@H]1O)c1ccccn1]

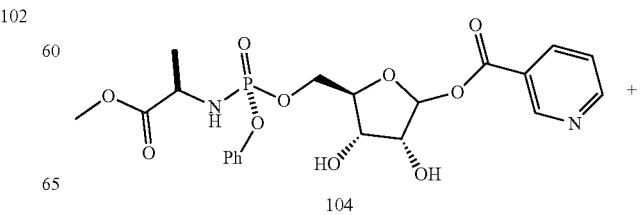

-continued

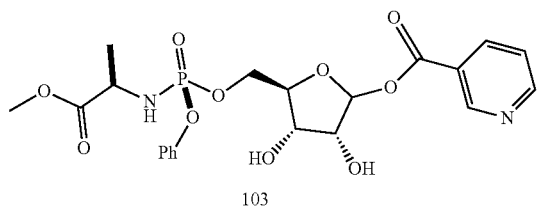

103

Compound 101 (2.5 g, 75% pure by LC-MS) was purified by chiral HPLC (CHIRALPAK IG, 250×4.6 mm, 5 (Mobile phase: n-Hexane:IPA: MeOH (75:05:20)) to provide 450 mg of compound 103 and 450 ng of compound 104.

Compound 103: $^1$H NMR[400 MHz, CD$_3$OD]: δ 9.09-9.08 (m, 1H), 8.69-8.68 (m, 1H), 8.38-8.35 (m, 1H), 7.58-7.48 (m, 1H), 7.28 (m, J=8.0 Hz, 2H), 7.14-7.09 (m, 3H), 6.24 (s, 1H), 4.41-4.33 (m, 2H), 4.24-4.15 (m, 3H), 3.88-3.84 (m, 1H), 3.61 (s, 3H), 1.28-1.24 (m, 3H). LCMS: m/z: 497.18 [M+H]$^+$, 98.51% (2.80 min.); Column: Kinetex EVO C18 (2.1×50 mm, 1.7 μm), Mobile Phase: A-0.1% NH3 in water; B-ACN, (T/% B: 0.01/10, 0.5/10, 5/40, 10/90); Flow Rate: 0.4 mL/min.

Compound 104: $^1$H NMR[400 MHz, CD$_3$OD]: δ 9.107-9.104 (m, 1H), 8.68 (dd, J=1.2, 4.8 Hz, 1H), 8.38-8.35 (m, 1H), 7.47-7.43 (m, 1H), 7.27 (t, J=7.6 Hz, 2H), 7.12 (t, J=7.6 Hz, 1H), 7.03 (d, J=8.4 Hz, 2H), 6.24 (s, 1H), 4.47-4.39 (m, 2H), 4.25-4.19 (m, 3H), 3.83-3.79 (m, 1H), 3.56 (s, 3H), 1.28-1.23 (m, 3H). LCMS: m/z: 497.18 [M+H]$^+$, 98.51% (2.80 min.); Column: Kinetex EVO C18 (2.1×50 mm, 1.7 im), Mobile Phase: A 0.1% NH3 in water; B-ACN, (T/% B: 0.01/10, 0.5/10, 5/40, 10/90); Flow Rate: 0.4 mL/min.

Scheme 4 illustrates the preparation of compound 105.

Example 5: Preparation of ((2S,3R,4S,5R)-3,4-dihydroxy-5-(((((S)—(((S)-1-isopropoxy-1-oxopropan-2-yl)amino)(phenoxy)phosphoryl)oxy)methyl)tetrahydrofuran-2-yl nicotinate (105)

To a stirred solution of (2S,3R,4S,5R)-3,4-dihydroxy-5-(hydroxymethyl)tetrahydrofuran-2-yl nicotinate (100) (100 mg, 1.33 mmol) in THF (1 mL) was added MgCl$_2$ (20 mg, 0.204 mmol) at RT and reaction mixture was stirred at RT for 15 min. Then (S)-isopropyl 2-(((S)-(perfluoro phenoxy)(phenoxy)phosphoryl)amino)propanoate (10) (110 mg, 0.243 mmol) and DIPEA (0.1 mL, 0.608 mmol) was added at RT. The reaction mixture was stirred at RT for 16 h.

The above sequence was run twice simultaneously to provide two batches. Both batches were combined, volatiles were evaporated under reduced pressure to provide crude compound. The crude compound was purified by column chromatography (100-200 mesh silica gel, 10% MeOH-DCM as eluent) to afford 105 (35 mg, 12% LCMS). LCMS: m/z: 525.16[M+H]$^+$, (2.11 min.). Column: EVO C$_{18}$ (2.1×50 mm, 1.7 μM). Mobile Phase: A-0.01% FA in water; B-0.01% FA in ACN, (T/% B: 0.01/10, 0.5/10, 4/90, 7/90). Flow Rate: 0.4 mL/min.

Example 6: Solid State Stability of Compounds 100, 101 and 102

Compounds 100, 101 and 102 were kept in glass vials at three different locations at temperatures of −25° C., 2-8° C. and −20° C. in order to assess solid state stability at room temperature, refrigerated conditions and in a deep freezer. The compounds from these vials were assessed for purity by UPLC at three different timepoints 0 hrs, 24 hrs and 48 hrs. Table 2 depicts the results obtained for solid state stability at 25° C., 2-8° C. and −20° C. respectively. Purity measurements were made at 0 hrs, 24 hours and 48 hours.

Scheme 4

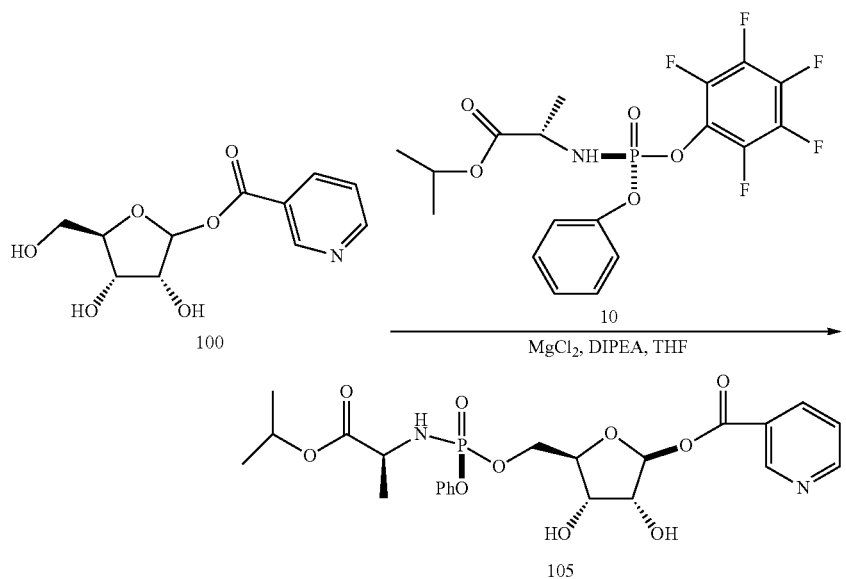

TABLE 2

| | Solid State Stability (% Purity) | | | | | | | | |
|---|---|---|---|---|---|---|---|---|---|
| | 100 | | | 101 | | | 102 | | |
| Temperature | 0 hr | 24 hr | 48 hr | 0 hr | 24 hr | 48 hr | 0 hr | 24 hr | 48 hr |
| 25° C. | 96.02 | 96.23 | 96.22 | 93.20 | 89.68 | 90.66 | 95.60 | 95.55 | 95.23 |
| 2-8° C. | 96.29 | 96.32 | 96.28 | 93.20 | 90.57 | 90.59 | 95.28 | 95.18 | 95.45 |
| −20° C. | 96.33 | 96.32 | 96.49 | 93.20 | 90.72 | 90.63 | 95.26 | 95.27 | 95.28 |

Example 7: Stability in Solutions (Simulated Gastric Fluid, Simulated Intestinal Fluid and pH Stability)

1 mg/ml solutions of compounds 101 and 102 were prepared in each buffer and analyzed as followed, respectively: Column: Acquity Halo C18 (2.1×100 mm, 2.7 μm), Mobile Phase: A-0.1% NH3; B-ACN, (T/% B: 0.01/10, 0.5/10, 5/40, 10/90) Flow Rate: 0.4 mL/min; and Column: Luna C18 (4.6×150 mm, 5 μm), Mobile Phase: A-0.1% TFA in water; B-0.1% TFA in ACN, (T/% B: 0.01/0, 5/0, 20/90, 25/90), Flow Rate: 0.7 mL/min.

1 mg/ml solutions of compound 100 were prepared in each buffer, diluted to 0.1 mg/ml in methanol at each time point and analyzed as follows: Gemini C-18, 250×4.6 mm, 5 im, Mobile Phase: Methanol Isocratic Flow Rate: 0.4 mL/min.

Table 3 illustrates the pH and buffer used.

TABLE 3

| pH conditions | Buffer Details |
|---|---|
| pH 1 | potassium chloride ~0.050 N, hydrochloric acid ~0.13 N |
| pH 2 | potassium chloride ~0.1 N, hydrochloric acid ~0.02 N |
| pH 4 | Sodium Citrate dihydrate ~0.034 M, Citric Acid ~0.2 N |
| pH 6 | Sodium Citrate dihydrate ~0.083 M, Citric Acid ~0.053 N |
| pH 7.4 | 10 mM Phosphate buffer saline |
| pH 9 | Sodium bicarbonate ~0.091 N, Sodium carbonate ~0.018 N |
| SGF | Simulated gastric fluid |
| SIF | Simulated intestinal fluid |

Table depicts stability of compound in solutions across the p range, simulated gastric and intestinal fluid.

TABLE 4

| | 100 (% remaining) | | | | | | | |
|---|---|---|---|---|---|---|---|---|
| Time points (h) | pH 1 | pH 2 | pH 4 | pH 6 | pH 7.4 | pH 9 | SGF | SIF |
| 0 | 100.0 | 100.0 | 100.0 | 100.0 | 100.0 | 100.0 | 100.0 | 100.0 |
| 1 | 100.9 | 91.9 | 95.7 | 92.0 | 57.1 | 17.7 | 99.1 | 76.4 |
| 2 | 104.8 | 93.8 | 99.2 | 86.4 | 41.1 | 7.8 | 89.2 | 64.5 |
| 4 | 80.7 | 93.0 | 97.9 | 70.9 | 37.5 | 7.6 | 79.6 | 41.4 |
| 8 | 49.0 | 54.8 | 49.0 | 50.4 | 46.3 | 7.5 | 65.4 | 40.5 |
| 24 | 53.0 | 28.6 | 42.3 | 55.1 | 46.0 | 6.6 | 71.7 | 36.7 |
| 48 | 45.6 | 36.0 | 42.9 | 47.7 | 36.6 | 8.1 | 55.0 | 38.7 |
| 1 1 week | 46.5 | 31.9 | 45.4 | 48.1 | 34.2 | 9.2 | 43.4 | 30.7 |

Table 5 depicts stability of compound 101 in solutions across the pH range, simulated gastric and intestinal fluid.

TABLE 5

| | 101 (% remaining) | | | | | | | |
|---|---|---|---|---|---|---|---|---|
| Time point (h) | pH 1 | pH 2 | pH 4 | pH 6 | pH 7.4 | pH 9 | SGF | SIF |
| 0 | 88.03 | 88.86 | 82.98 | 88.78 | 88.58 | 90.15 | 90.17 | 91.59 |
| 1 | 85.91 | 88.82 | 83.96 | 88.01 | 88.62 | 80.81 | 88.8 | 91.12 |
| 2 | 85.4 | 87.46 | 82.79 | 87.98 | 88.48 | 70.65 | 87.74 | 91.16 |
| 4 | 81.82 | 85.16 | 81.96 | 87.55 | 87.24 | 48.75 | 83.09 | 90.07 |
| 8 | 74.41 | 81.19 | 79.6 | 86.2 | 86.71 | 26.14 | 77.12 | 90.28 |
| 24 | 50.26 | 63.31 | 70.75 | 86.09 | 86.62 | 4.45 | 41.98 | 85.29 |
| 48 | 16.35 | 35.33 | 69.7 | 73.74 | 79.75 | 0 | 29.17 | 85.54 |
| 1 week | 1.01 | 13.5 | 37.7 | 73.66 | 67.37 | 0 | 3.41 | 76.58 |

Table 6 depicts stability of compound 102 in solutions across the pH range, simulated gastric and intestinal fluid.

TABLE 6

| | 102 (% remaining) | | | | | | | |
|---|---|---|---|---|---|---|---|---|
| Time points (h) | pH 1 | pH 2 | pH 4 | pH 6 | pH 7.4 | pH 9 | SGF | SIF |
| 0 | 95.73 | 95.67 | 95.37 | 96.31 | 95.8 | 94.05 | 95.54 | 96.45 |
| 1 | 95.69 | 95.65 | 95.32 | 96.32 | 95.7 | 74.72 | 94.73 | 96.01 |
| 2 | 95.64 | 95.66 | 95.27 | 96.26 | 94.95 | 56.28 | 93.68 | 96.02 |
| 4 | 95.61 | 95.64 | 95.25 | 96.27 | 94.34 | 49.14 | 93.65 | 95.96 |
| 8 | 95.64 | 95.67 | 95.26 | 96.25 | 93.43 | 23.34 | 93.69 | 95.77 |
| 24 | 95.61 | 95.56 | 95.26 | 95.73 | 90.13 | 14.94 | 93.61 | 94.28 |
| 48 | 95.64 | 95.54 | 95.05 | 95.66 | 83.6 | 0.63 | 93.58 | 93.75 |
| 1 week | 95.56 | 95.39 | 94.76 | 94.47 | 61.5 | 0 | 91.04 | 84.49 |

Preparation of Stock Solutions or ell Based Assays

Compounds 100, 101 and 102 were weighted out to prepare 60 μM stock solutions in RPMI media. 200 ng/mL solution of Rac-tenofovir d6 (Vivan Life-Sciences) was prepared in methanol (MeOH) and placed at −20° C. until use.

Example 8: Effect of Compounds on Cellular NAD+ Levels in Jurkat Cells

Jurkat Cells, sourced from NCCS Pune, were cultured in RPMI media containing FBS & Antibiotics. Cells from different flasks (90% confluent) were pooled into a 15 mL conical tube and centrifuged for 5 mins at 1200 rpm for 5 mins. The supernatant solution was discarded, and the pellet was washed with 5 mL sterile PBS (without $Ca^{2+}$ & $Mg^{2+}$). The tube was then centrifuged at 1200 rpm for 5 mins and the supernatant was discarded. The cell pellet was resuspended in 7 mL of RPMI media, and a cell count was done using 10 uL of the cell solution. 1.5 million cells from the cell solution were seeded into 1.5 mL microcentrifuge tubes. The compounds (100, 101, 102 and nicotinic acid) were added along with RPMI media without PBS to make up the total volume to 1 mL and the final concentration was 30 μM. The tubes were placed in racks and gently swirled to mix the compounds into the media containing the cells. These tubes were then incubated for 4 hours in a 37° C. incubator at 5% $CO_2$. After 4 hours of incubation the cells were spun down at 1000 rpm for 10 mins, the supernatant was discarded carefully, and cells were snap frozen in liquid nitrogen. When the samples were run, the extraction of the cells was on ice, cells were lysed using 20 uL deionized water and then ice cold 80% methanol containing the internal standard—Rac-Tenofovir D was added. The tubes were then vortexed at 2500 rpm for 8 minutes and then centrifuged at 125000 rpm for 10 minutes. 150 uL of the supernatant was carefully transferred to HPLC vials and was analyzed for $NAD^+$ on the Abscised 4000 Q Trap LCMS/MS system. A C18, 3.5 μm, 2.1×100 mm, Bridge Column was used in the LC. The mobile phase consisted of 10 mM ammonium acetate with 0.1% acetic acid and 0.1% hexylamine as Solvent-A and 10 mM Ammonium acetate with 0.1% acetic acid and 0.1% hexylamine in 95/5 $MeOH/H_2O$ as Solvent-B. The gradient used was 0 mins-0.0% B, 0.5 mins-100% B, 1.5 mins-100% B, 3.0 mins-100% B, 3.1 mins-0.0% B, 7.0-STOP. The column flow rate was 0.5 mL/min. The sample injection volume was 3 L.

All four compounds (100, 101, 102 and nicotinic acid) showed statistical significance in terms of $NAD^+$ level increases compared to the untreated cells after four hours of incubation, with the highest increase seen in cells treated with compound 101 as illustrated in FIG. 1.

Example 9: Effect of Compounds on Cellular $NAD^+$ Levels in Huh-7 Cells

Huh-7 Cells, sourced from NCCS Pune, were cultured in RPMI media containing FBS & Antibiotics. Cells from different flasks (80-90% confluent) were pooled into a 15 mL conical tube and centrifuged for 5 mins at 1200 rpm for 5 mins. The supernatant solution was discarded, and the pellet was washed with 5 mL sterile PBS (without $Ca^{2+}$ and $Mg^{2+}$). The tube was then centrifuged at 1200 rpm for 5 mins and the supernatant was discarded. The cell pellet was resuspended in 7 mL of RPMI media, and a cell count was done using 10 uL of the cell solution. 1.5 million cells from the cell solution were seeded into 1.5 mL microcentrifuge tubes. The compounds (100, 101, 102 and nicotinic acid) were added along with RPMI media without PBS to make up the total volume to 1 mL and the final concentration was 30 μM. The tubes were placed in racks and gently swirled to mix the compounds into the media containing the cells. These tubes were then incubated for 4 hours in a 37° C. incubator at 5% $CO_2$. After 4 hours of incubation the cells were spun down at 1000 rpm for 10 mins, the supernatant was discarded carefully, and cells were snap frozen in liquid nitrogen. When the samples were run, the extraction of the cells was on ice, cells were lysed using 20 uL deionized water and then ice cold 80% methanol containing the internal standard—Rac-Tenofovir D was added. The tubes were then vortexed at 2500 rpm for 8 minutes and then centrifuged at 125000 rpm for 10 minutes. 150 uL of the supernatant was carefully transferred to HPLC vials and was analyzed for $NAD^+$ on the Abscised 4000 Q Trap LCMS/MS system. A C18, 3.5 μm, 2.1×100 mm, Bridge Column was used in the LC. The mobile phase consisted of 10 mM ammonium acetate with 0.1% acetic acid & 0.1% hexylamine as Solvent-A and 10 mM Ammonium acetate with 0.1% acetic acid and 0.1% hexylamine in 95/5 $MeOH/H_2O$ as Solvent-B. The gradient used was 0 mins-0.0% B, 0.5 mins-100% B, 1.5 mins-100% B, 3.0 mins-100% B, 3.1 mins-0.0% B, 7.0-STOP. The column flow rate was 0.5 mL/min. The sample injection volume was 3 L.

Figure 2:
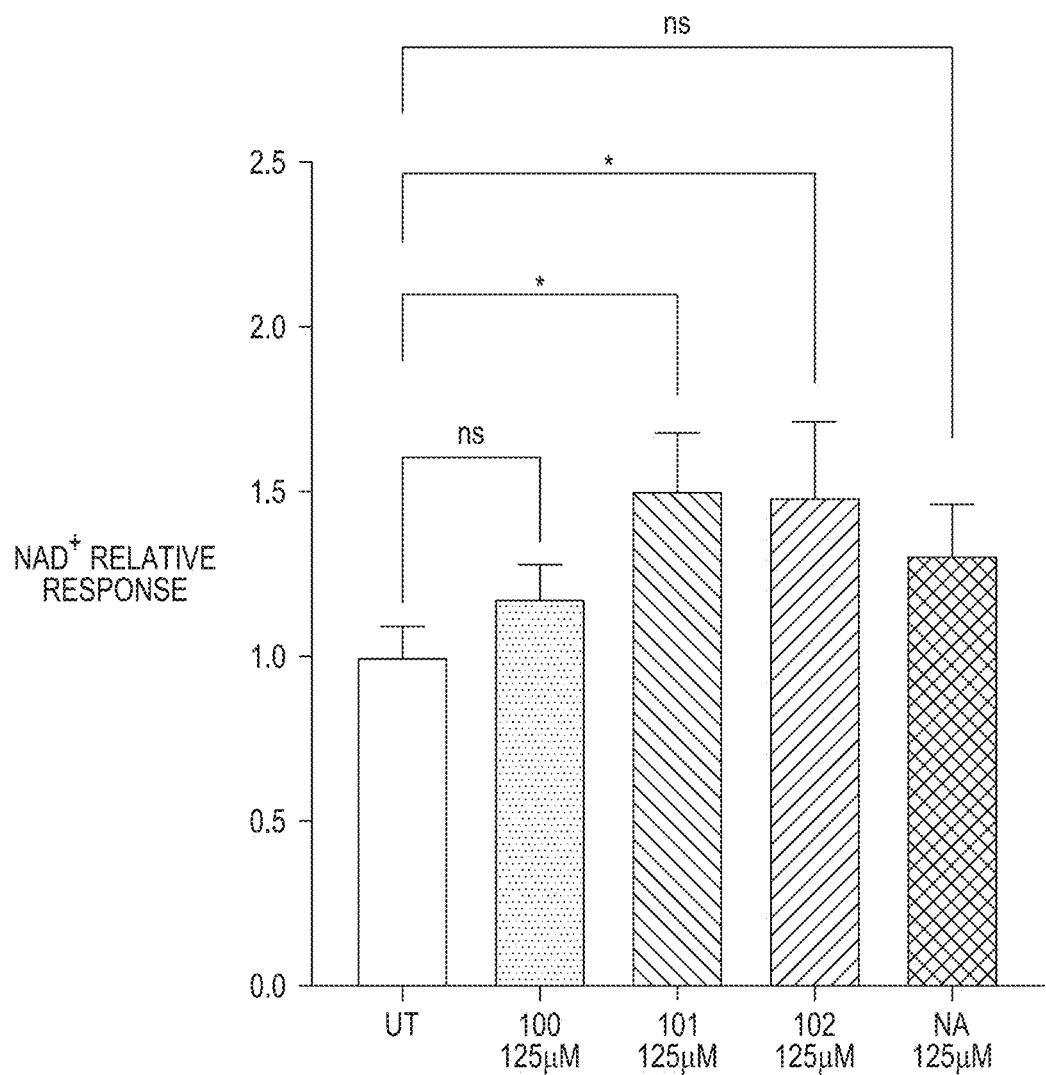
FIG. 2 depicts NAD+ increase in Huh7 cells supplemented with 125 μM of compounds 100, 101, 102 and nicotinic acid.
Figure 3A:
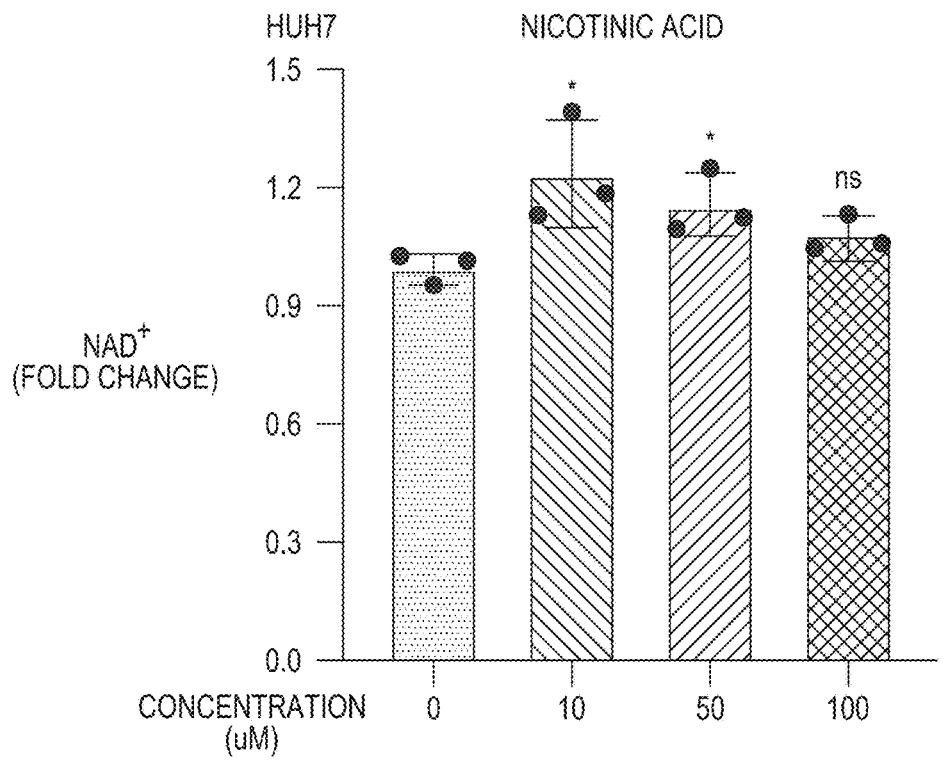
FIG. 3A depicts dose dependent NAD+ increase in Huh7 cells supplemented with varying amounts of nicotinic acid.
Figure 3B:
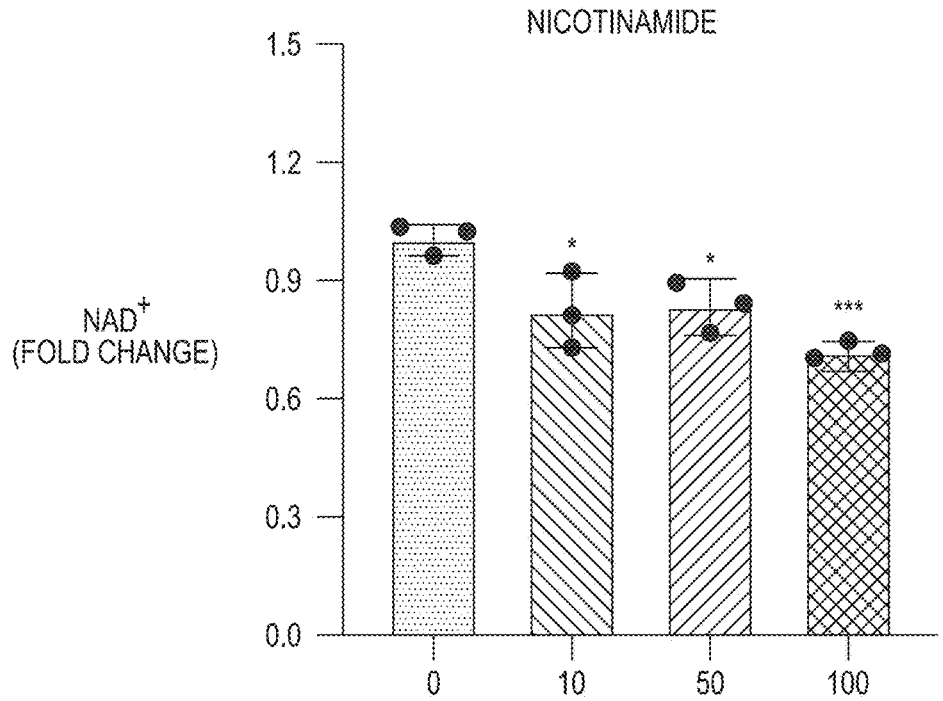
FIG. 3B depicts dose dependent NAD+ increase in Huh7 cells supplemented with varying amounts of nicotinamide.
Figure 3C:
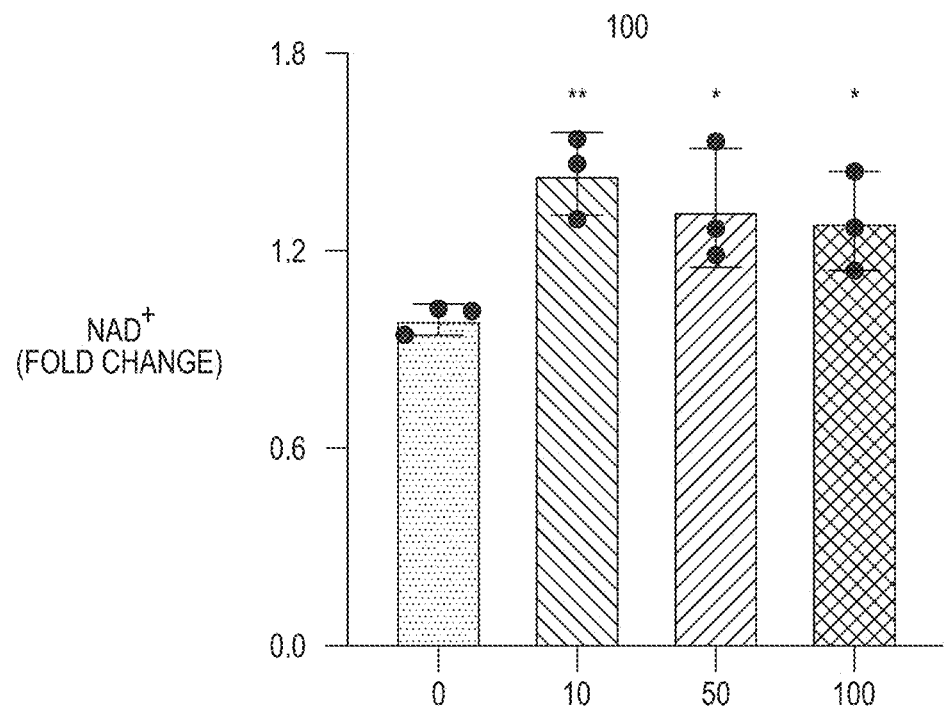
FIG. 3C depicts dose dependent NAD+ increase in Huh7 cells supplemented with varying amounts of compound 100.
Figure 3D:
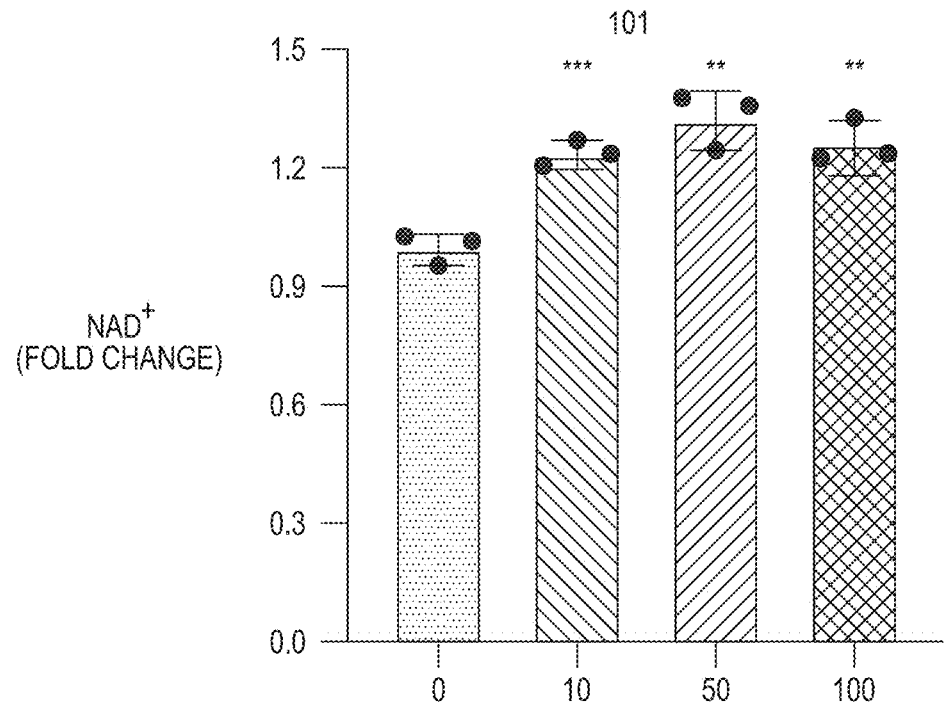
FIG. 3D depicts dose dependent NAD+ increase in Huh7 cells supplemented with varying amounts of compound 101.
Figures 4A, 4B, 4C, 4D:
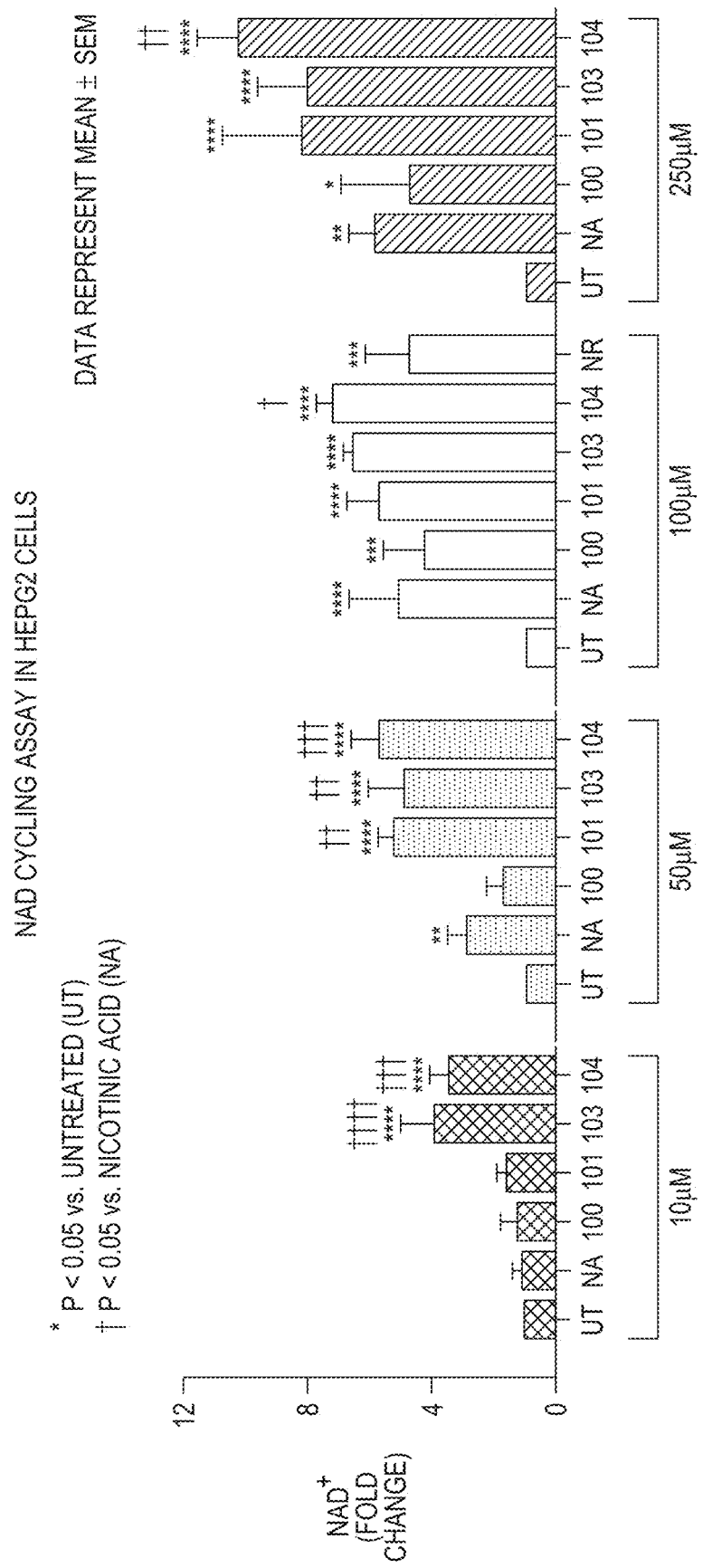
FIG. 4A illustrates the results for NAD cycling assays in HepG2 cells for a 10 μM of compounds 100, 101, 103, 104 and nicotinic acid.
FIG. 4B illustrates the results for NAD cycling assays in HepG2 cells for a 50 μM of compounds 100, 101, 103, 104 and nicotinic acid.
FIG. 4C illustrates the results for NAD cycling assays in HepG2 cells for a 100 μM of compounds 100, 101, 103, 104 and nicotinic acid.
FIG. 4D illustrates the results for NAD cycling assays in HepG2 cells for a 250 μM of compounds 100, 101, 103, 104 and nicotinic acid.

FIG. 2 depicts $NAD^+$ increase in HEPG2 cells. All four compounds (100, 101, 102 and nicotinic acid) at 125 μm, showed an increase in terms of $NAD^+$ level increases compared to the untreated cells after four hours of incubation.

Example 10: Effect of Compounds 103 and 104 in Primary Human Hepatocytes at 250 μM Cryopreserved primary human hepatocytes, sourced from Lonza were cultured and were seeded into 6 well dishes with 0.5 million cells per well. Compounds 103 and 104 were added in duplicate and incubated for four hours at 37° C. in an incubator. The cells were later spun down and extracted. The supernatant was tested via LCMS/MS for $NAD^+$.

The results are illustrated in FIGS. 3A-3D. In primary human hepatocytes compounds 103, 104 and nicotinic acid, at 250 μM showed an increase with statistically significant $NAD^+$ level increases compared to untreated cells after four hours of incubation.

Example 11: Effect of Compounds on Cellular $NAD^+$ Levels in HepG2 Cells-NAD Cycling Assay HepG2 cells were seeded at densities of 1 million cells per well in a 6 well plate. The next day, cells were treated with test compounds for 4 hours and were harvested using the below protocol. Each well was washed once with 2 mL ice cold PBS which was removed and 400 μL 2M $HClO_4$ (perchloric acid) was added to each well, which was scraped and the residue transferred to 1.5 mL tubes and spun down. 100 μL of the supernatant was transferred to a clean 1.5 mL vial and 150 μL KOH/MOPS 2M/0.6M (neutralization buffer) was added to each vial under vortex which was spun down. The pH was measured following the NAD cycling protocol.

NAD standards were prepared from 0 to 0.5 μM in water as per Table 7.

TABLE 7

| NAD Standards Table | | | | |
|---|---|---|---|---|
| Final concentration | NAD 1 μM | NAD 0.5 μM | $H_2O$ | Final Volume |
| 0.5 μM | 500 | 0 | 500 | 1000 |
| 0.4 μM | 0 | 80 | 20 | 100 |
| 0.3 μM | 0 | 60 | 40 | 100 |
| 0.2 μM | 0 | 40 | 60 | 100 |
| 0.1 μM | 0 | 20 | 80 | 100 |
| 0 μM | 0 | 0 | 100 | 100 |

The cycling reaction was prepared as follows. 10 μl samples were added followed by water to bring the volume up to 25 μl. 25 μl of each standard was used in duplicates for the reaction. Then 50 μl of mix A (cycling mix) was added to the sample and standards. Mix A contained the following:

| Mix A 2X (Cycling) | |
|---|---|
| | μl (for 5 ml) |
| 0.2 M TRIS pH 8.0 (1 M) | 1000 |
| 600 mM Ethanol (100% = 20 M) | 150 |

-continued

| Mix A 2X (Cycling) | |
|---|---|
| | μl (for 5 ml) |
| 2 mM EDTA (100 mM) pH 7.4 | 100 |
| 4 mM oxaloacetate (1 M in 0.5M HCl) | 20 |
| 0.04 mg/ml BSA (20 mg/ml) | 10 |
| mK | 3720 |
| Up to | 5000 |

Reaction was initiated using 25 μL enzyme mix (15 U/ml of alcohol dehydrogenase+15 U/mL of malate dehydrogenase). The samples were incubated at 37° C. for 30 minutes in a water bath and the reaction terminated by heating in a water bath for 5 minutes at 80° C. Then 25 μl of the sample was used in the detection step. 100 μl mix B, which contains following components were added to the sample.

| Mix B 2X (Indicator) | μl |
|---|---|
| 100 mM Bis-Tris pH 9.0 (1 M) | 500 |
| 1 mM NAD (5 mM) | 1000 |
| 10 mM L-Glutamate (100 mM) | 500 |
| mQ | 3000 |
| Up to | 5000 |

Reaction was initiated using a start reagent (prepared by mixing 10 μl of malate dehydrogenase and 10 μl of glutamate oxaloacetic transaminase in 1 ml of water. The reading were measured at 340 nm in a envision plate reader. The results are shown in FIGS. 4A-4D.

All five compounds (100-105 and nicotinic acid, at 10 μM, 50 μM, 100 μM and 250 μM showed an increase with MP-statistical significance for 101, 103 and 104 in terms of NAD$^+$ level increases compared to the untreated cells after four hours of incubation. Compounds 103 and 104 showed statistically significant increase even at the lowest concentrations of 10 μM. Compound 104 also showed statistically significant increase when compared to nicotinic acid at all concentrations.

Example 12: Effect of Compounds 103 and 104 in Primary Human Hepatocytes

Cryopreserved primary human hepatocytes, sourced from Lonza were cultured and were seeded into 6 well dishes with 0.5 million cells per well. Compounds 103 and 104 were added in duplicate and incubated for four hours at 37° C. in an incubator. The cells were later spun down and extracted. The supernatant was tested via LCMS/MS for NAD$^+$.

Figure 5:
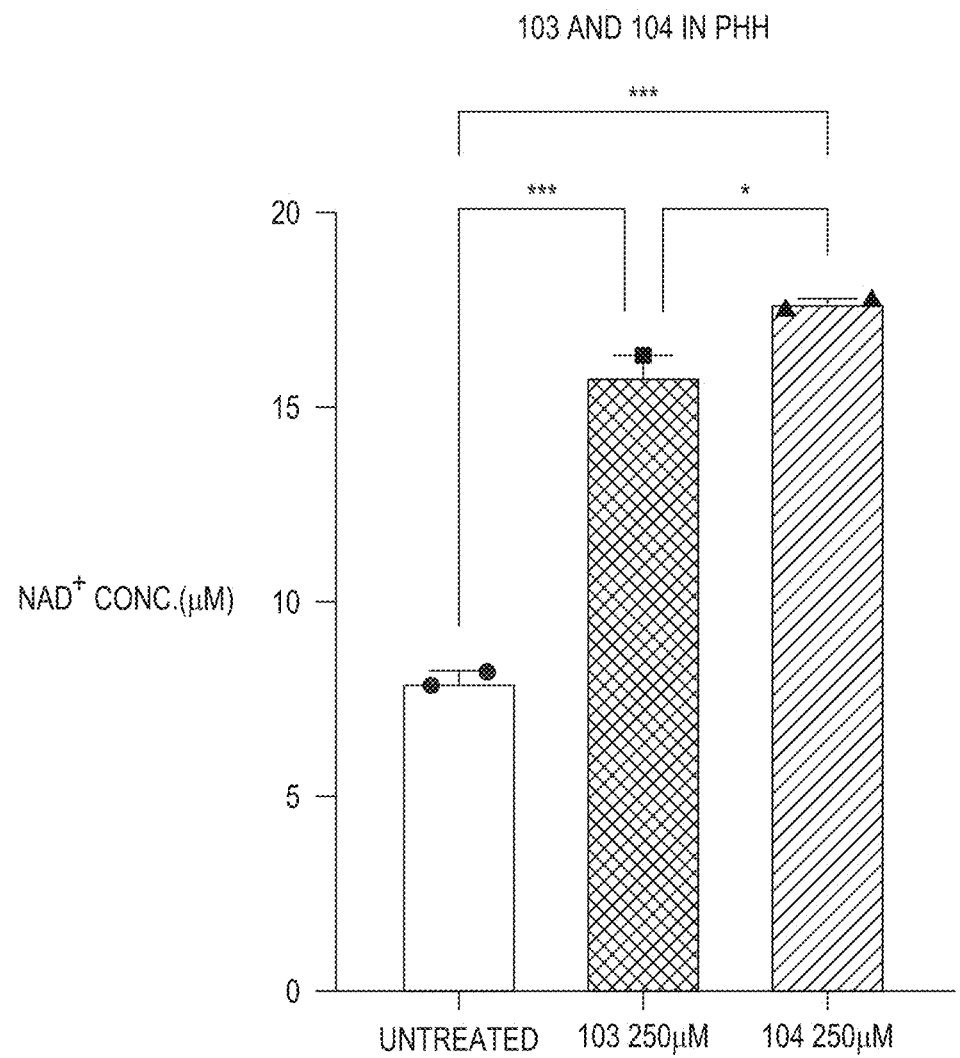
FIG. 5 illustrates the effect of 250 μM of compounds 103 and 104 on NAD+ levels in primary human hepatocytes.
Figures 6A, 6B:
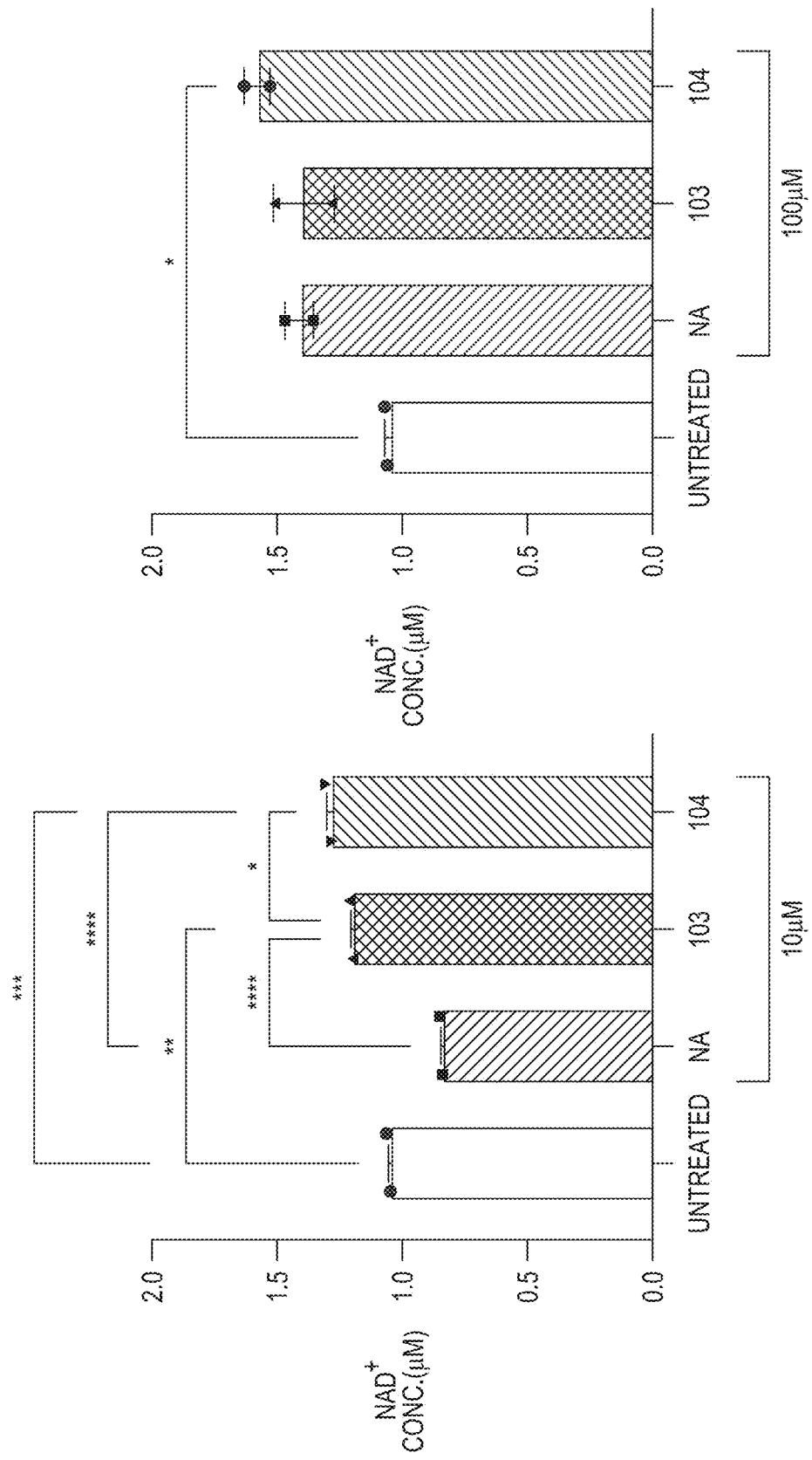
FIG. 6A illustrates in-vitro cytotoxicity of compounds 103 and 104 in HepG2 cells at 10 μM.
FIG. 6B illustrates in-vitro cytotoxicity of compounds 103 and 104 in HepG2 cells at 100 μM.

The results are illustrated in FIGS. 5 and 6. In primary human hepatocytes compounds 103, 104 and nicotinic acid, at 10 μM showed an increase with statistically significant NAD$^+$ level increases compared to untreated cells after four hours of incubation.

Example 13: In-Vitro Cytotoxicity of Compounds 100, 101 and 102 in HepG2

Figure 7:
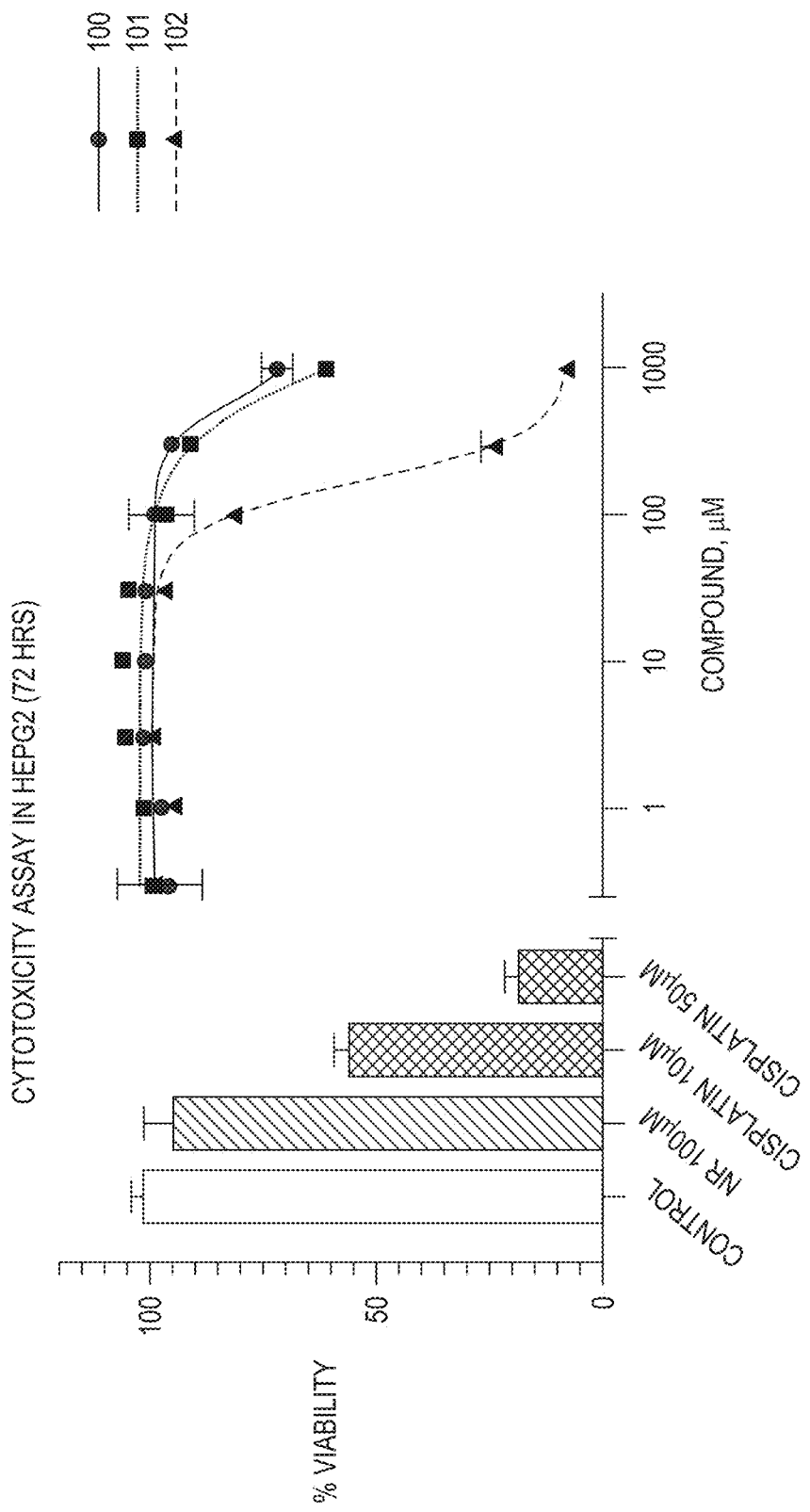
FIG. 7 illustrates cytotoxicity of compounds 100, 101 and 102 to HepG72 cells at various concentrations.
Figure 8A:
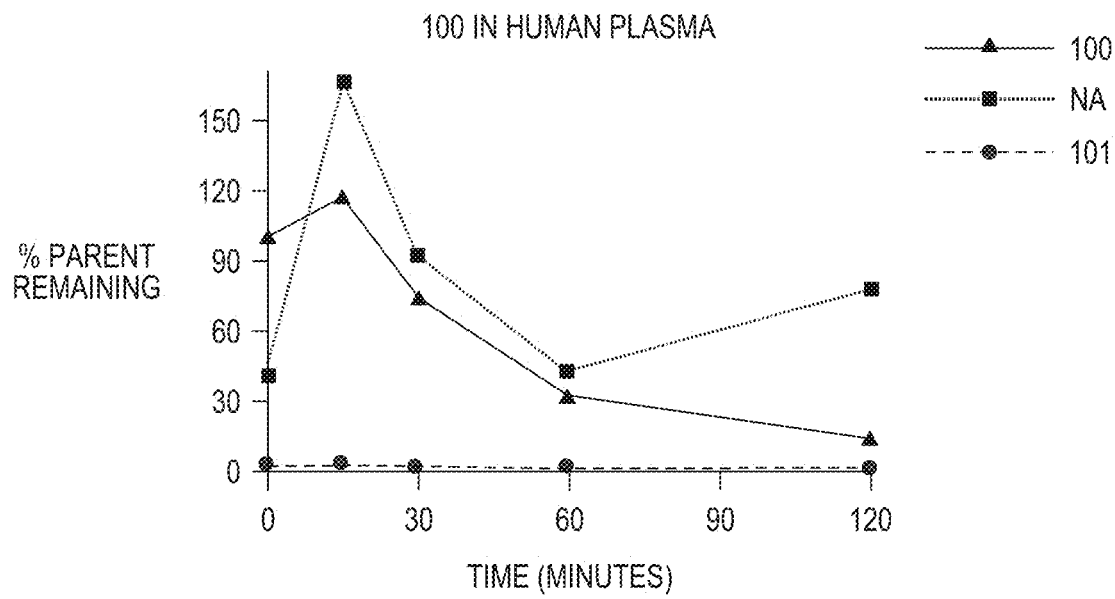
FIG. 8A illustrates human plasma stability of compound 100.
Figure 8B:
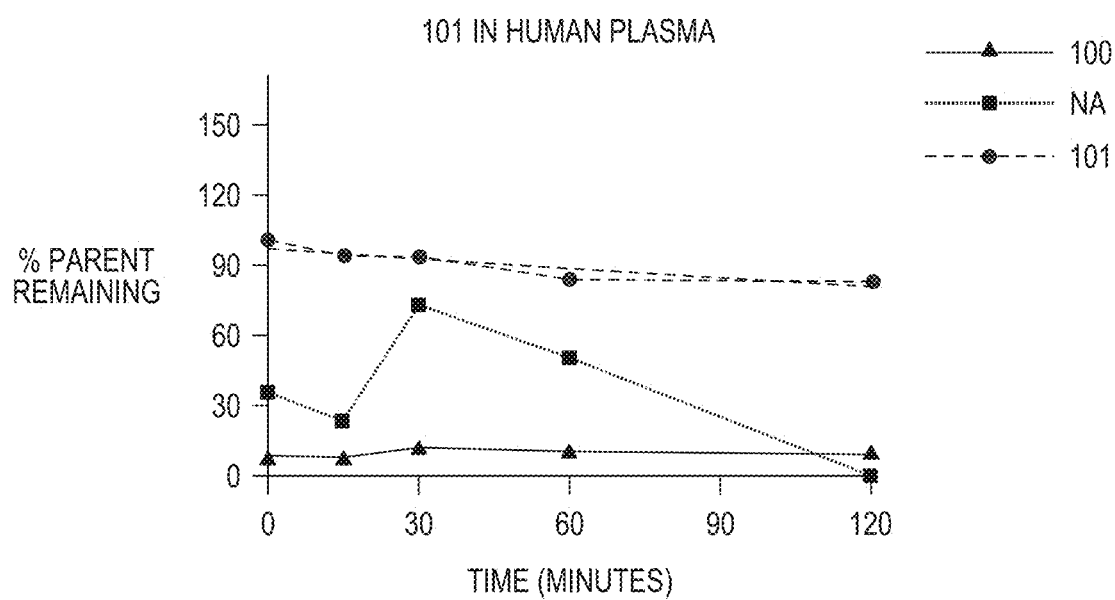
FIG. 8B illustrates human plasma stability of compound 101.
Figure 8C:
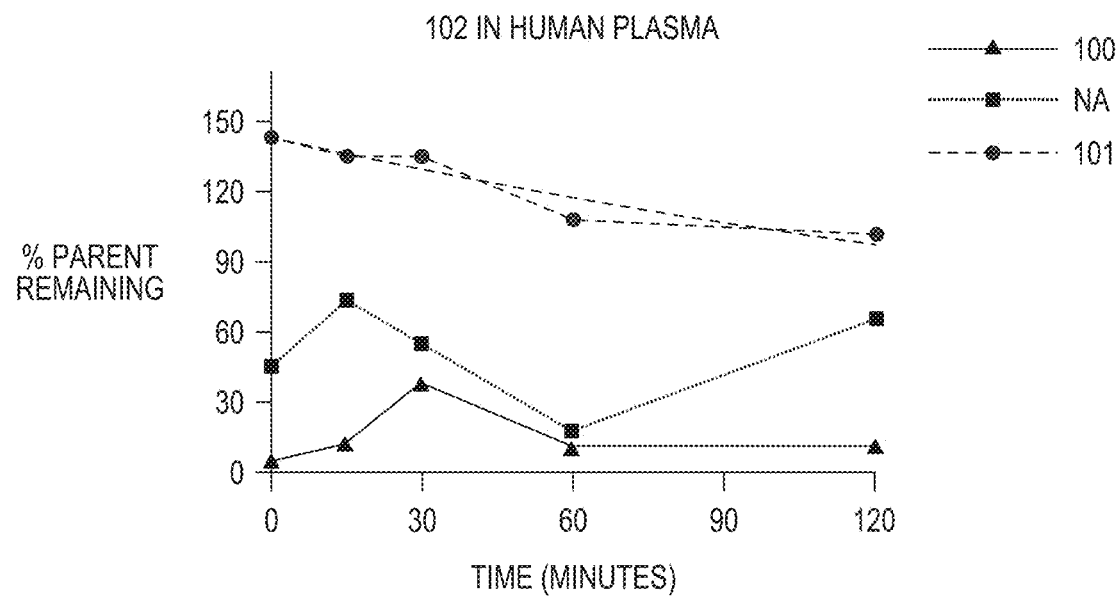
FIG. 8C illustrates human plasma stability of compound 102.
Figure 8D:
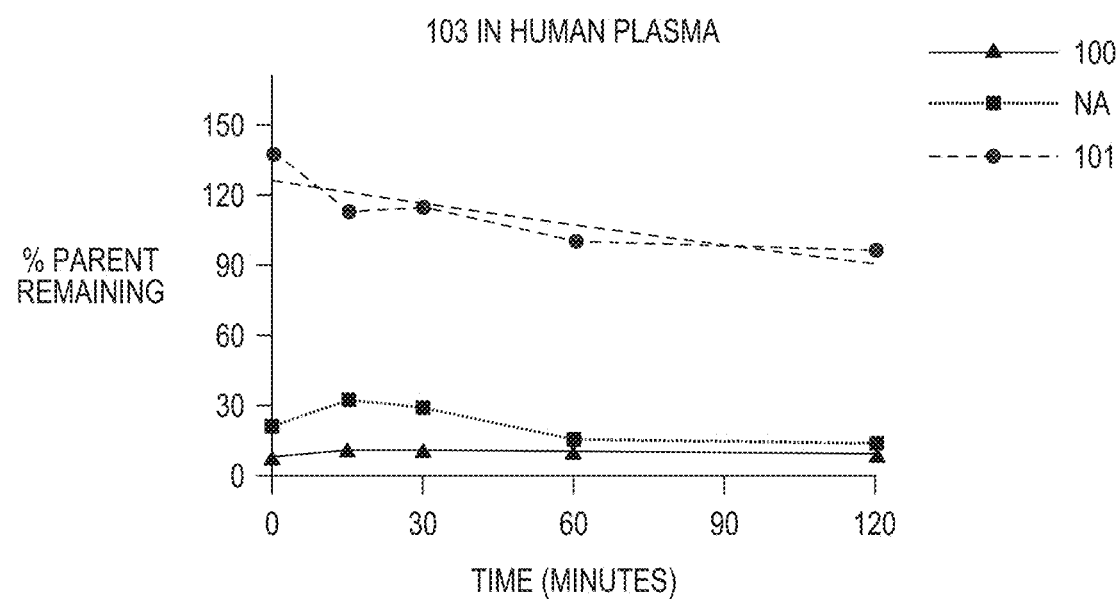
FIG. 8D illustrates human plasma stability of compound 103.
Figure 8E:
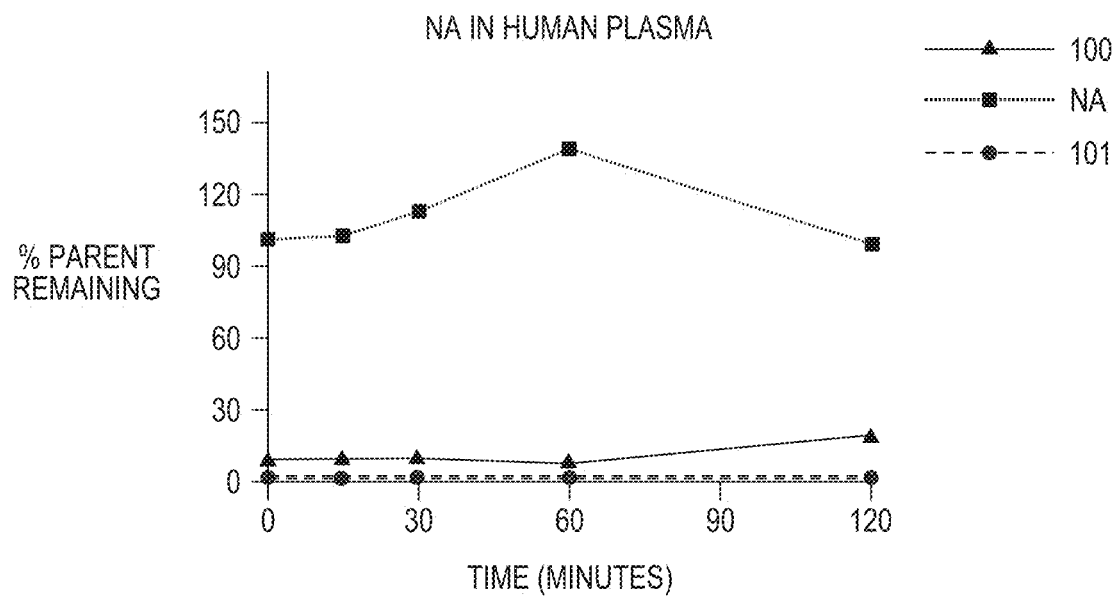
FIG. 8E illustrates human plasma stability of nicotinic acid.
Figure 9A:
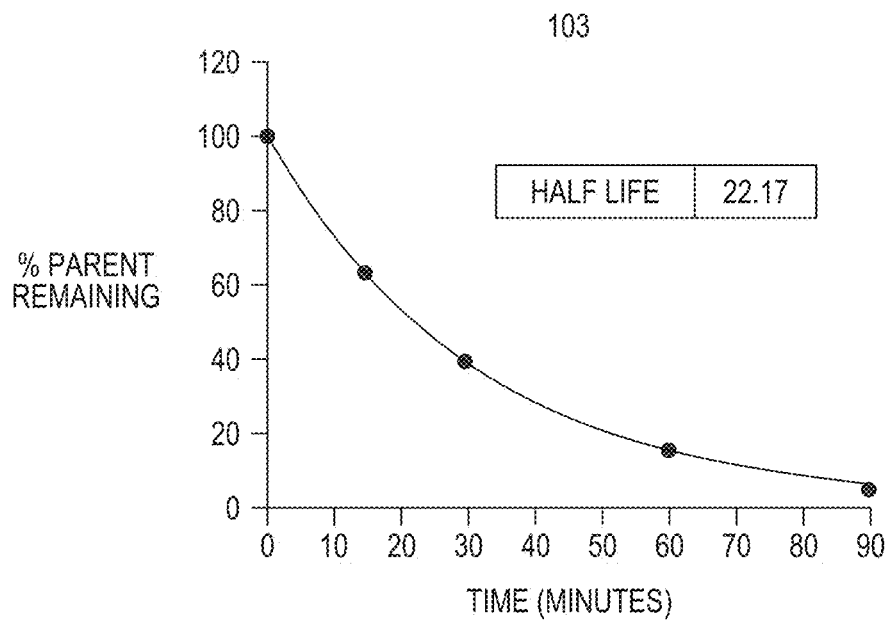
FIG. 9A illustrates human hepatocyte stability of compound 103.
Figure 9B:
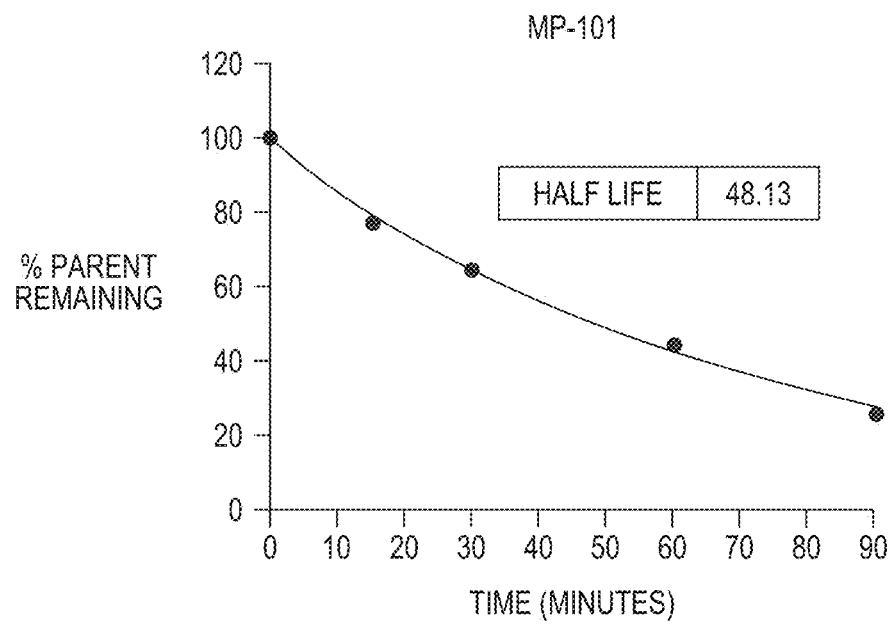
FIG. 9B illustrates human hepatocyte stability of compound 104.
Figure 9C:
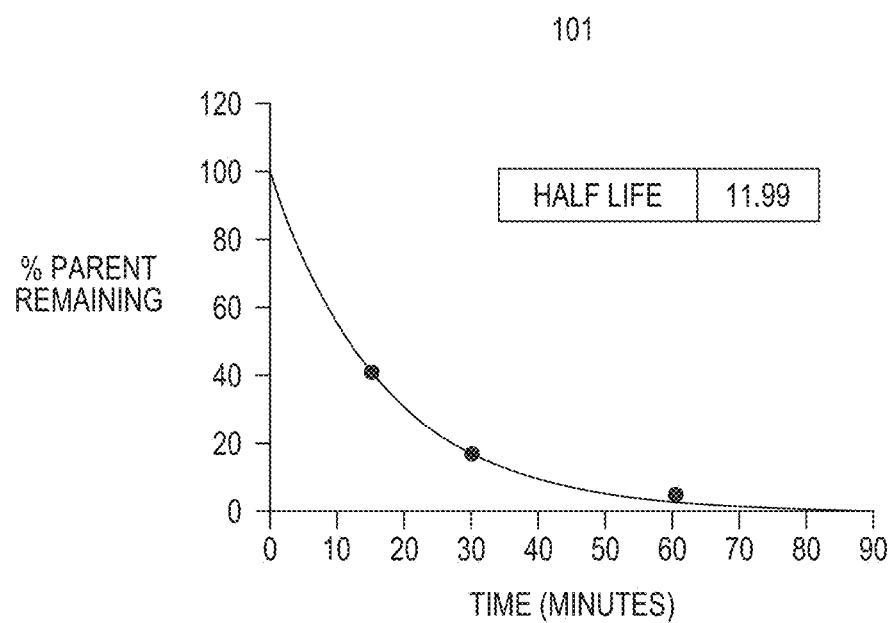
FIG. 9C illustrates human hepatocyte stability of compound 101.
Figure 9D:
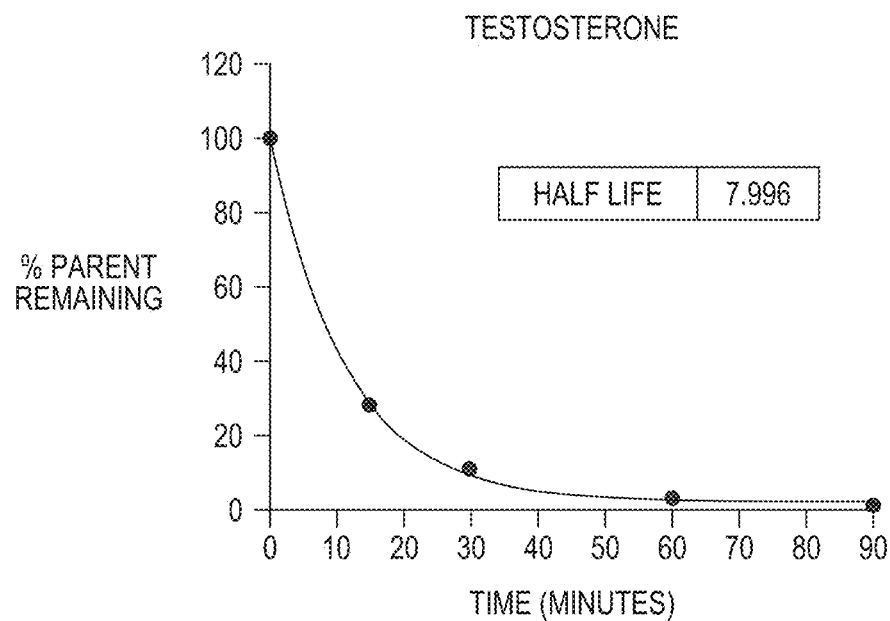
FIG. 9D illustrates human hepatocyte stability of Testosterone.
Figure 9E:
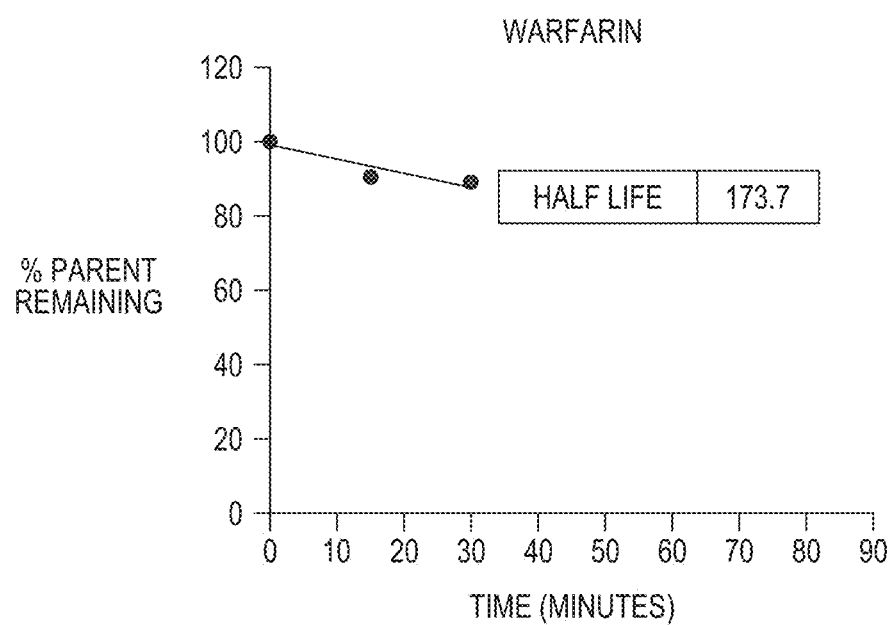
FIG. 9E illustrates human hepatocyte stability of Warfarin.

HepG2 cells were cultured and used for testing the in-vitro cytotoxicity of compounds 100, 101 and 102. The Cell Titer-Glo® Luminescent Cell Viability assay kit, procured from Promega was used to determine the same. Concentrations of 0.3, 1, 3, 10, 30, 100, 300 and 1000 μM were tested for compounds 100, 101 and 102. 1000 cells per well were plated and incubated for 72 hours with each of these concentrations. Cisplatin (6.5 μM) and nicotinamide riboside (NR) (100 μM) were used as controls. Generation of a luminescent signal proportional to the amount of ATP present, was measured as luminescence (RLU) on a plate reader. The amount of ATP is directly proportional to the number of cells present in culture. The results are shown in FIG. 7.

Example 14: CACO2 Permeability of Compounds 100, 101 and 102

The Caco-2 permeability assay was performed to measure the permeability of compounds 100, 101 and 102 through a human intestinal epithelial cell barrier. The endpoint measured is the intestinal permeability expressed as apparent permeability—Papp value. All permeability values are represented as $\times 10^{-6}$ cm/sec. Permeability ranking based on following criteria shown in Table 8.

TABLE 8

| | Avg Papp × $10^{-6}$ | | | % Recovery | |
|---|---|---|---|---|---|
| | | | Efflux | | |
| Compound | A to B | B to A | Ratio | A to B | B to A |
| 100 | 0.5 | 0.6 | 1.2 | 98.5 | 89.0 |
| 101 | 0.2 | 6.1 | 39.0 | 86.5 | 87.9 |
| 102 | 0.9 | 0.8 | 1.0 | 94.9 | 90.7 |
| Furosemide | 0.2 | 11.7 | 73.7 | 72.2 | 73.9 |
| Verapamil | 14.5 | 27.7 | 1.9 | 93.5 | 114.7 |
| Carbamazepine | 22.2 | 23.4 | 1.1 | 89.3 | 91.0 |
| Domperidone | 3.9 | 20.3 | 5.2 | 61.8 | 76.4 |

Low: Papp A-B <2.5 × $10^{-6}$ cm/sec.
High: Papp A-B ≥2.5 × $10^{-6}$ cm/sec.
Compounds 100 and 102 demonstrated low efflux ratio below while compound 101 had effective efflux.

Example 15: Kinetic Solubility of Compounds 100, 101 and 102

TABLE 9

| Compound | Mean Solubility (μM) | Mean Solubility (μg/mL) | % Solubility |
|---|---|---|---|
| 100 | 96.5 | 24.6 | 96 |
| 101 | 116.9 | 58.0 | 100 |
| 102 | 105.3 | 26.9 | 100 |
| Albendazole | 0.66 | 0.2 | QC |
| Flurbiprofen | 110.7 | 27 | QC |

The kinetic solubility for test compounds was measured in aqueous buffer when added from an existing stock solution in DMSO (50 μL 10 mM DMSO stock). The target compound concentration was 100 μM (kinetic), the assay buffer was 0.1 M phosphate buffered saline pH 7.4, the mixing period was 1.5 h (kinetic). The sample was prepared by centrifugation or filtration and the detection method used was HPLC with UV-vis spectrometry.

All tested compounds demonstrated >95% solubility at 100 μM as illustrated in table 9, above. Albendazole and Flurbiprofen (QC compounds) data are consistent with historical data.

Example 16: Human Hepatocyte Clearance of Compounds 100-104

TABLE 10

| Compound | T½ | Intrinsic Clearance (CL Int) (µL/min/106° cells) | Remarks |
|---|---|---|---|
| 100 | 142.50 | 4.86 | Medium |
| 101 | 12.85 | 53.93 | High |
| 102 | 45.67 | 15.17 | Medium |
| 103 | 22.17 | 31.26 | High |
| 104 | 48.13 | 14.4 | Medium |
| Testosterone | 9.14 | 75.79 | High* |
| Warfarin | 335.86 | 2.06 | Low* |

A hepatocyte vial was taken out from the liquid nitrogen tank and was thawed in a water bath maintained at 37° C. The thawed cell suspension was transferred into a torsion tube containing 50 mL of thawing media (Xenotech). The thawing media containing hepatocytes was centrifuged at 1000 rpm for 5 min, the supernatant was discarded and the pellet was resuspended in 2 ml of Xenotech OptiIncubate Media. The cells were counted by using a haemocytometer after mixing an aliquot of cell suspension with equal volume of trypan blue. The cell suspension was diluted to a working density of 2 million cells with DMEM media without FBS/incubation media. 10 mM stock solution of test compound was prepared in DMSO and diluted to a concentration of 1 mM with DMSO. Working concentration of 2 µM was prepared by further dilution with PBS.

The assay was performed in duplicates (n=2). 150 µL of 2 million cell working stock of hepatocyte cell suspension was added to a 24 well plate and incubated in a 37° C. incubator, with speed of 500 RPM for 10 min. 150 µL of 2 µM working stock of test compound was incubated separately. The reaction at 0, 15, 30, 60 and 90 min was stopped by precipitating 20 µL of incubation mixture with 200 µL of acetonitrile containing internal standard. The samples were vortexed for 5 min at 1200 rpm and centrifuged at 4000 rpm for 10 min. The supernatant was separated and diluted 1:1 with water before injecting in LC-MS/MS analysis. Testosterone and warfarin were used as assay controls.

Compounds 100, 102 and 104 demonstrated medium clearance, while compound 101 and 109 demonstrated high clearance in human hepatocytes as illustrated in Table 10, above. Testosterone and Warfarin (QC compounds) data are consistent with reference data.

| Title | Human-Hepatocyte Stability |
|---|---|
| Test Conc (µM) | 1 µM |
| Incubation Time points (min) | 0, 15, 30, 60 and 90 |
| No of Replicates | Two |
| Number of cells in the assay | 1 Million cells/mL |
| Analysis Method | LC-MS/MS |

Example 17: Human Hepatocyte Stability of Compounds 100, 101, 103 and 104

TABLE 11

| Time Point | % Parent Remaining | | | | | |
|---|---|---|---|---|---|---|
| (mins) | 100 | 101 | 103 | 104 | Testosterone | Warfarin |
| 0 | 100 | 100 | 100 | 100 | 100 | 100 |
| 15 | 97 | 43 | 63 | 78 | 28 | 91 |
| 30 | 87.6 | 20.1 | 40 | 65 | 11 | 89 |
| 60 | 73.0 | 6.4 | 15 | 45 | 3 | 96 |
| 90 | 66.4 | 2.0 | 5 | 24 | 1 | 96 |

10 mM stock solution of test compound was prepared in DMSO and diluted to a concentration of 1 mM with DMSO. Working concentration of 2 µM was prepared by further dilution with PBS. Preincubation mixture of 150 µL of hepatocyte cell suspension (1,000,000 cells/mL, INVITROGRO HT medium buffer), was added to vials for preincubation for 10 min @37° C.

150 µL of 2 µM working stock of the test compound was added to the cell suspension and incubated at @37 C at 500 rpm. The reaction was stopped at 0, 15, 30, 60 and 90 min by precipitating 50 µL of the incubation mixture with 150 µL of acetonitrile. Samples were vortexed for 5 min at 1200 rpm and centrifuged at 4000 rpm for 10 min. 150 µL of the supernatant was diluted with 150 µL of water and injected in MS system (SCIEX, API 4500 Q Trap) for analysis.

Compounds 100, 102 and 104 demonstrated medium clearance, while compound 101 and 109 demonstrated high clearance in human hepatocytes as illustrated in Table 11, above. Testosterone and Warfarin (QC compounds) data are consistent with reference data. FIGS. 9A-E illustrate the results for compounds 101, 103, 104, testosterone and warfarin in graphical form.

Example 18: Human Plasma Protein Binding of Compounds 100, 101 and 102

The test compounds were weighed and prepared as 10 mM stocks in 100% DMSO. 10 µM is the final test concentration for all compounds. The base plate of the RED Chamber was rinsed with 20% ethanol for 10 min, rinsed twice with water dried and either used immediately or covered using the protocol suggested by the manufacturer.

The samples were prepared by spiking test compound(s) in plasma at 10 µM final concentration. 200 µL of plasma containing the test compound was added into the donor well (RED Chamber) of the insert. Simultaneously 350 µL of dialysis buffer (1xPBS) was added into the receiver well (white chamber). Two measurements were made for each test compound. The plate was covered with a sealer and incubated at 37° C. degrees on an orbital shaker at 500 rpm for 5 hours.

After incubation, 25 µl of plasma (RED chamber) and 25 µl of buffer (white chamber) samples were separately collected into separate centrifugation tubes. Plasma and buffer samples were precipitated with 200 µL of 100% acetonitrile containing internal standards. 25 µl of $T_0$ (T Zero) plasma samples (samples before 5 hours incubation) were collected (To samples were processed immediately after the preparation of plasma working stock solution. These samples serve as a measure for calculating the percentage recovery of the test compound and precipitated using 100% acetonitrile containing internal standards). The samples were vortexed at 1000 rpm for 5 min and centrifuged at 4000 rpm for 10 min. The supernatant was diluted 2-fold with water and injected into LC-MS/MS. The reference compound(s) are Atenolol and Warfarin.

The % of Plasma bound/unbound fraction was calculated by the following equation: % Unbound or % free=100*(Fc/Tc); % Recovery=100 (Fc+Tc)/Tc where Tc=Total compound concentration as determined by the calculated concentration on the plasma side of the membrane (concentration in plasma chamber), Fc=Free compound concentration as determined by the calculated concentration on the buffer side of the membrane (concentration in buffer chamber) and $T_0$=Total compound concentration as determined before dialysis.

TABLE 12

| Compound | % Unbound in plasma | % Bound in plasma | Fraction unbound | Remarks |
|---|---|---|---|---|
| 100 | ND | ND | ND | |
| 101 | 30.59 | 69.41 | 0.31 | Medium binding |
| 102 | ND | ND | ND | |
| Warfarin | 0.54 | 99.56 | 0.005 | High binding |
| Atenolol | 83.52 | 16.48 | 0.84 | Low binding |

Compounds 100 and 102 were not detected indicating no protein binding as shown in Table 12, above.
Atenolol and warfarin data is consistent with reference data.

Example 19: Plasma Stability of Compounds 101, 102, 103 and 104

Fresh plasma was incubated at 37° C. for 10 min, mixed and centrifuged to remove any aggregated protein. The clear supernatant was aliquoted into an assay plate. The plasma was equilibrated to 37° C. and biotransformation was initiated by addition of compound solution (1 µL of 200× compound was added to 200 µl of plasma and mixed well (final concentration-1 µM)).

The $T_0$ samples were immediately collected after mixing the compound. The assay plate was placed on a shaker at 37° C. and samples were collected at 15 min, 30 min, 60 min and 120 min. At each time point, 20 µl of sample was added to 300 µl of acetonitrile with internal standard. The samples were vortexed for 5 min at 1200 rpm and centrifuged at 4000 rpm for 10 min and the supernatant was diluted with water before injecting into a LC-MS/MS for analysis.

% Remaining=100*(peak area ratio at timepoint/peak area ratio at $T_0$). Peak area ratio=Peak area of analyte/Peak area of Internal standard Plasma half-life $(T_{1/2})$=0.693/K where K is the slope found in the linear fit of the natural logarithm of the fraction remaining of the parent compound vs. incubation time.

TABLE 13

| Time-point (min) | % of compound w.r.t minutes of corresponding treatment | | | | | | | | |
|---|---|---|---|---|---|---|---|---|---|
| | Compound 100 | | | Compound 103 | | | Compound 104 | | |
| | 101 | 100 | NA | 101 | 100 | NA | 101 | 100 | NA |
| 0 | 2.6 | 100 | 41 | 143 | 5 | 44 | 137 | 7 | 20 |
| 15 | 3.5 | 118 | 166 | 135 | 12 | 73 | 112 | 10 | 31 |
| 30 | 2.4 | 75 | 93 | 135 | 38 | 54 | 114 | 10 | 28 |
| 60 | 2.5 | 33 | 43 | 108 | 11 | 17 | 100 | 10 | 15 |
| 120 | 2.0 | 15 | 79 | 102 | 12 | 66 | 97 | 10 | 14 |

TABLE 14

| Timepoint (min) | % of compound w.r.t minutes of corresponding treatment | | | | | |
|---|---|---|---|---|---|---|
| | Compound 101 | | | Nicotinic Acid | | |
| | 101 | 100 | NA | 101 | 100 | NA |
| 0 | 100 | 7 | 34 | 2 | 9 | 100 |
| 15 | 93 | 6 | 22 | 2 | 9 | 102 |
| 30 | 93 | 11 | 73 | 2 | 10 | 112 |
| 60 | 84 | 10 | 50 | 3 | 8 | 139 |
| 120 | 84 | 9 | 0 | 3 | 20 | 99 |

The results are shown graphically in FIGS. 8A-8E and in tabular form in Tables 13 and 14. Compounds 100-104 and nicotinic acid (NA) were evaluated for human plasma stability at 5 µM from 0-2 Hrs. Compounds 101-104 shows slow degradation of the parent molecule which indicates stability over 2 hrs. All four compounds were converted into nicotinic acid over the 2 hr time course. Compound 100 and nicotinic acid were measured to determine breakdown of the compounds. The compound 101 measurement represents compounds 103 and 104 as the LCMS assay is the same for determining both the compound 101 isomers.

Example 20: PK Study of Compound 100 in Rats

TABLE 15

| Group | Compound | Dose | Dose volume | Route | Plasma time points | Analyte quantification | Tissues (24 hrs) |
|---|---|---|---|---|---|---|---|
| G1 | 100 | 415 mg/kg | 10 ml/kg | Oral Gavage | Predose, 15 mins, 30 mins, 1 Hr, 2 Hr, 4 Hr, 8 Hr, 12 Hr & 24 Hr | 100 & Nicotinic Acid | Liver & Kidney |
| G2 | 100 | 83 mg/kg | 5 ml/kg | IV by Slow Bolus | Predose, 5 mins, 15 mins, 30 mins, 1 Hr, 2 Hr, 4 Hr, 8 Hr & 24 Hr | 100 & Nicotinic Acid | Liver & Kidney |
| G3 | Nicotinic Acid | 200 mg/kg | 10 ml/kg | Oral Gavage | Predose, 15 mins, 30 mins, 1 Hr, 2 Hr, 4 Hr, 8 Hr, 12 Hr & 24 Hr | 100 & Nicotinic Acid | Liver & Kidney |

TABLE 15-continued

| Group | Compound | Dose | Dose volume | Route | Plasma time points | Analyte quantification | Tissues (24 hrs) |
|---|---|---|---|---|---|---|---|
| G4 | Nicotinic Acid | 40 mg/kg | 5 ml/kg | IV by Slow Bolus | Predose, 5 mins, 15 mins, 30 mins, 1 Hr, 2 Hr, 4 Hr, 8 Hr & 24 Hr | 100 & Nicotinic Acid | Liver & Kidney |

Rats were divided in to 4 groups Group 1-Group 4 (n=3). Compound 100 was administered to Group 1 and Group 2 (Group 1 oral route at 415 mg/kg, Group 2 intravenous route at 83 mg/kg). Nicotinic acid was administered to Group 3 and Group 4 (Group 3 oral route at 200 mg/kg, Group 4 intravenous route at 40 mg/kg). 150 to 200 μL blood was collected in 1.5 mL centrifuge tubes with pre addition of K2-EDTA at predose, 15 mins, 30 mins, 1 hr, 2 hr, 4 hr, 8 Hr, 12 hr & 24 hr for oral and predose, 5 mins 15 mins, 30 mins, 1 hr, 2 hr, 4 hr, 8 hr & 24 hr for intravenous dose. K2EDTA blood samples were immediately (<5 min) centrifuged for 10 minutes at 14000 rpm at 4° C., plasma was separated and the residue stored at −80° C. for analysis for compound 100 and nicotinic acid estimation. The study design is summarized in Table 15 above.

Simultaneously one aliquot (50 μL) of whole blood was collected, crashed immediately after collection with 1 ml crashing solution and vortexed for 2 minutes and stored at −80° C. until analysis for NAD and NADH estimation. Kidney and liver were collected 24 hrs post dose by sacrificing the animal without perfusion. Immediately after collection, the tissue samples were snap frozen in liquid nitrogen and stored at −80° C. until homogenization and analysis (tissues were homogenized in methanol:water (1:1) with the ratio 1 g 19 mL of solvent maintained before analysis.

Other details of the procedure are shown in Table 16 below.

TABLE 16

| Extraction Technique | Protein Precipitation |
|---|---|
| Surrogate matrix | 5% BSA in Water |
| Extraction Solvent or Crashing Solution | Acetonitrile + Methanol + Water (40:40:20)(0.1 M Formic acid) containing internal standard (telmisartan + verapamil) Acetonitrile for 100 and Nicotinic acid. |
| Calibration Curve & QC preparation: | 100/NA-5 μL of working calibration standards add to 45 μL of 5% BSA and precipitated with 0.5 mL of acetonitrile containing internal standard (telmisartan + verapamil) at 500 ng/mL conc. Vortexed for 5 minutes, centrifuged at 14000 rpm for 10 min at 4° C. and 1-5 μL supernatant injected into LCMSMS. |
| Blood, plasma & tissue Sample Preparation: | 100/NA-50 μL of biological sample precipitated with 0.5 mL of acetonitrile containing internal standard (telmisartan + verapamil) at 500 ng/ml conc. Vortexed for 5 minutes, centrifuged at 14000 rpm for 10 min at 4° C. and 1-5 μL supernatant injected into LCMSMS. |

Bio analysis was performed for the analytes in respective samples (NAD, NADH, compound 100 & NA) by using API 4S00 Q trap system. All analyte quantifications were analyzed using Analyst software.

Figure 10A:
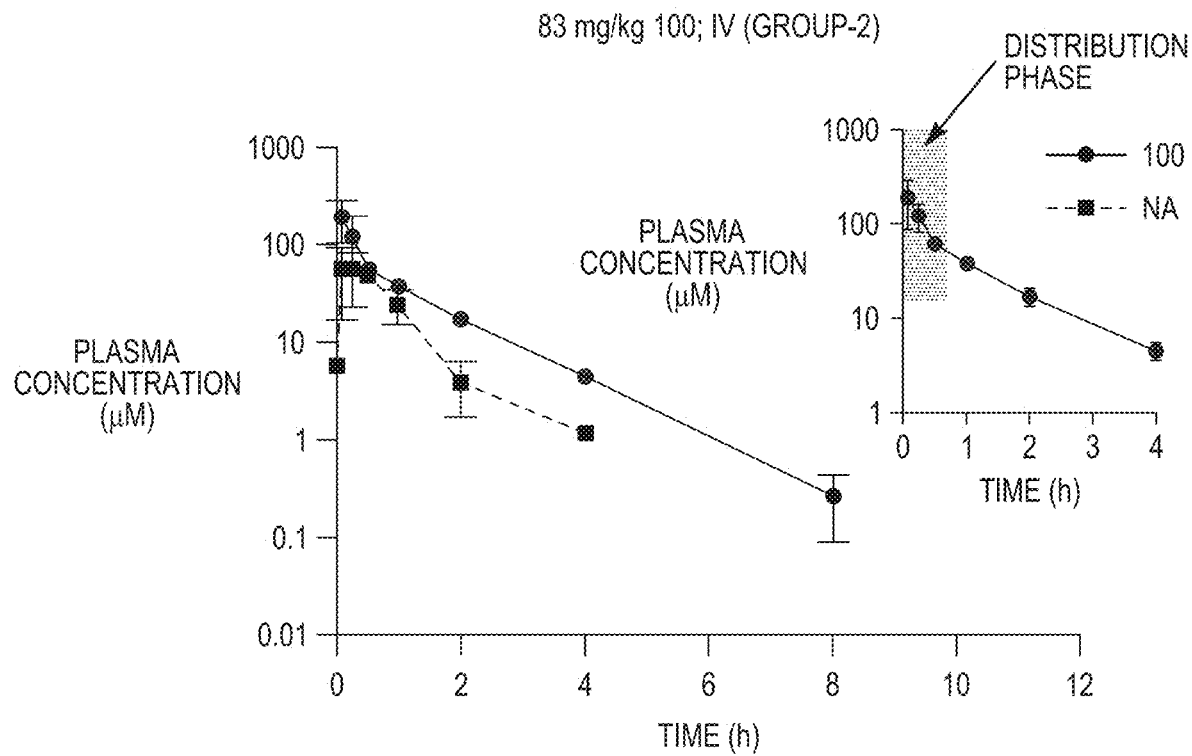
FIG. 10A illustrates pharmacokinetics results for a Group 2 dosage of compound 100 (83 mg/kg).
Figure 10B:
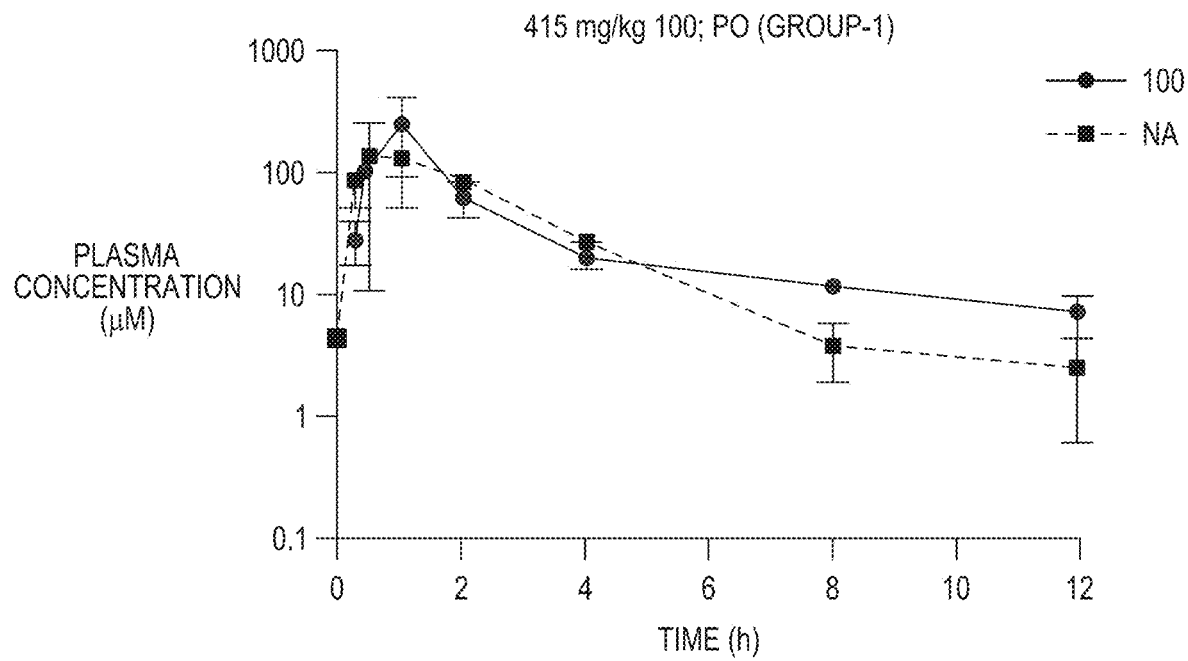
FIG. 10B illustrates pharmacokinetics results for a Group 1 dosage (415 mg/kg) of compound 100.
Figure 11A:
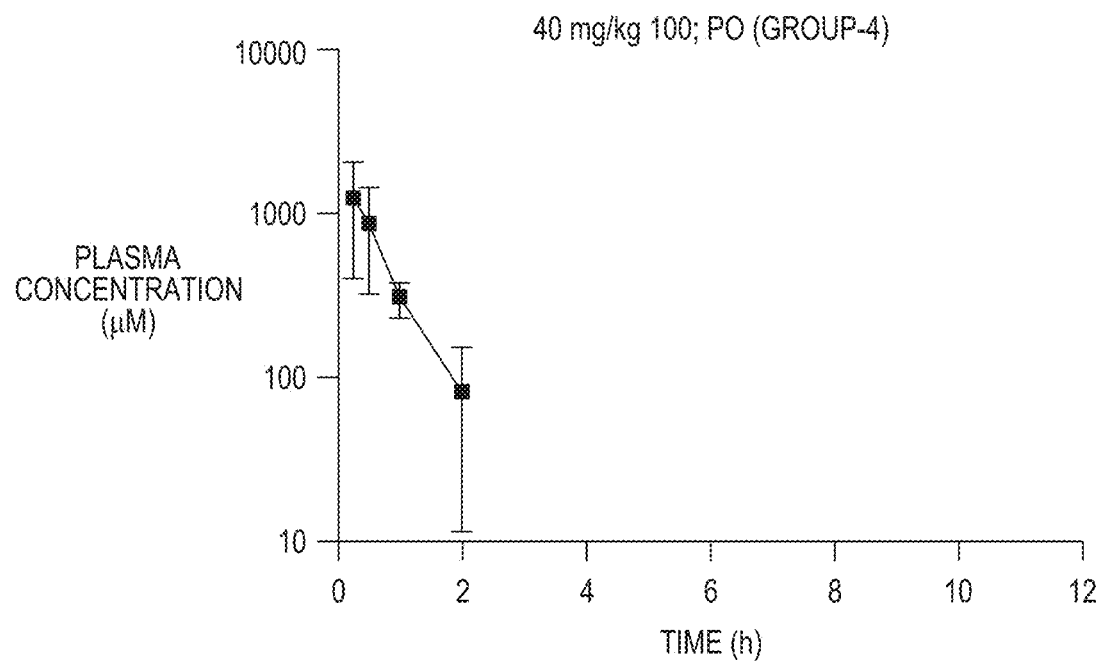
FIG. 11A illustrates pharmacokinetics results for Group 4 dose (40 mg/kg) of nicotinic acid.
Figure 11B:
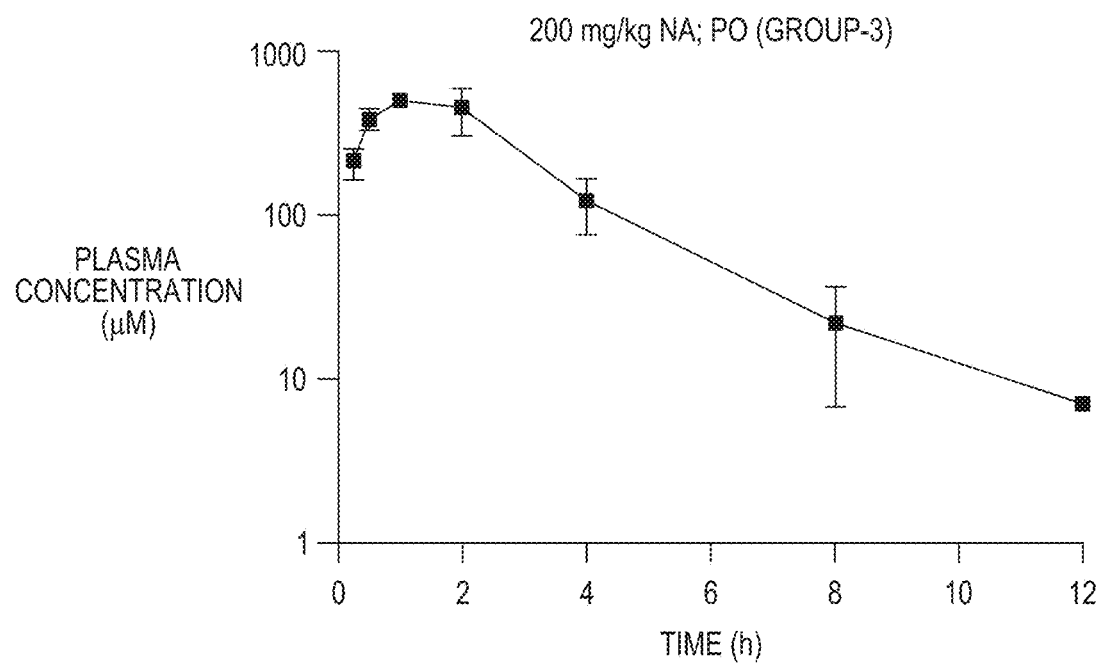
FIG. 11B illustrates pharmacokinetics results Group 3 dose (200 mg/kg) of nicotinic acid.

The results for Group 2 and Group 1 are illustrated in FIGS. 10A and 10B, respectively. The results for Group 4 and Group 3 are illustrated in FIGS. 11A and 11B, respectively.

Pharmacokinetic parameter for Group 2 are tabulated in Table 17.

TABLE 17

| 83/mg/kg IV dosing | Compound 100 | Nicotinic acid |
|---|---|---|
| $T_{1/2}$ (h) | 1.01 ± 0.22 | 0.644 ± 0.038 |
| $T_{max}$ (h) | 0.139 ± 0.096 | 0.389 ± 0.529 |
| $C_{max}$ (μM) | 188.0 ± 97.2 | 66.38 ± 28.70 |
| $AUC_{0-1}$ (μM) | 148.01 ± 34.0 | 70.57 ± 7.53 |
| CL (L/h/kg) | 2.26 ± 0.57 | NA |
| $V_{ss}$(l/kg) | 3.40 ± 1.62 | NA |

Pharmacokinetic parameter for Group 4 are tabulated in Table 18.

TABLE 18

| 40/mg/kg IV dosing | Nicotinic acid |
|---|---|
| $T_{1/2}$ (h) | 0.448 ± 0.277 |
| $T_{max}$ (h) | 0.25 ± 0.00 |
| $C_{max}$ (μM) | 1240 ± 833 |
| $AUC_{0-1}$ (μM) | 1077 ± 426 |
| CL (L/h/kg) | 0.304 ± 0.093 |
| $V_{ss}$(l/kg) | 0.211 ± 0.156 |

Pharmacokinetic parameter for Group 3 are tabulated in Table 19.

TABLE 19

| 200/mg/kg PO dosing | Nicotinic acid |
|---|---|
| $T_{1/2}$ (h) | 1.42 ± 0.43 |
| $T_{max}$ (h) | 1.33 ± 0.58 |
| $C_{max}$ (μM) | 518.6 ± 83.3 |

TABLE 19-continued

| 200/mg/kg PO dosing | Nicotinic acid |
|---|---|
| AUC$_{0-1}$ (µM) | 1682 ± 305 |
| F (%) | 29 |

Compound 100 IV pharmacokinetics depicts a biphasic rapid distribution followed by elimination. Compound 100 delivered by IV is likely degraded in rat plasma at $T_{1/2}$ of 1 hour. The $T_{1/2}$ of compound 100 following oral administration is consistent with the hepatocyte stability in vitro (5-6 h)

Figures 12A, 12B, 12C:
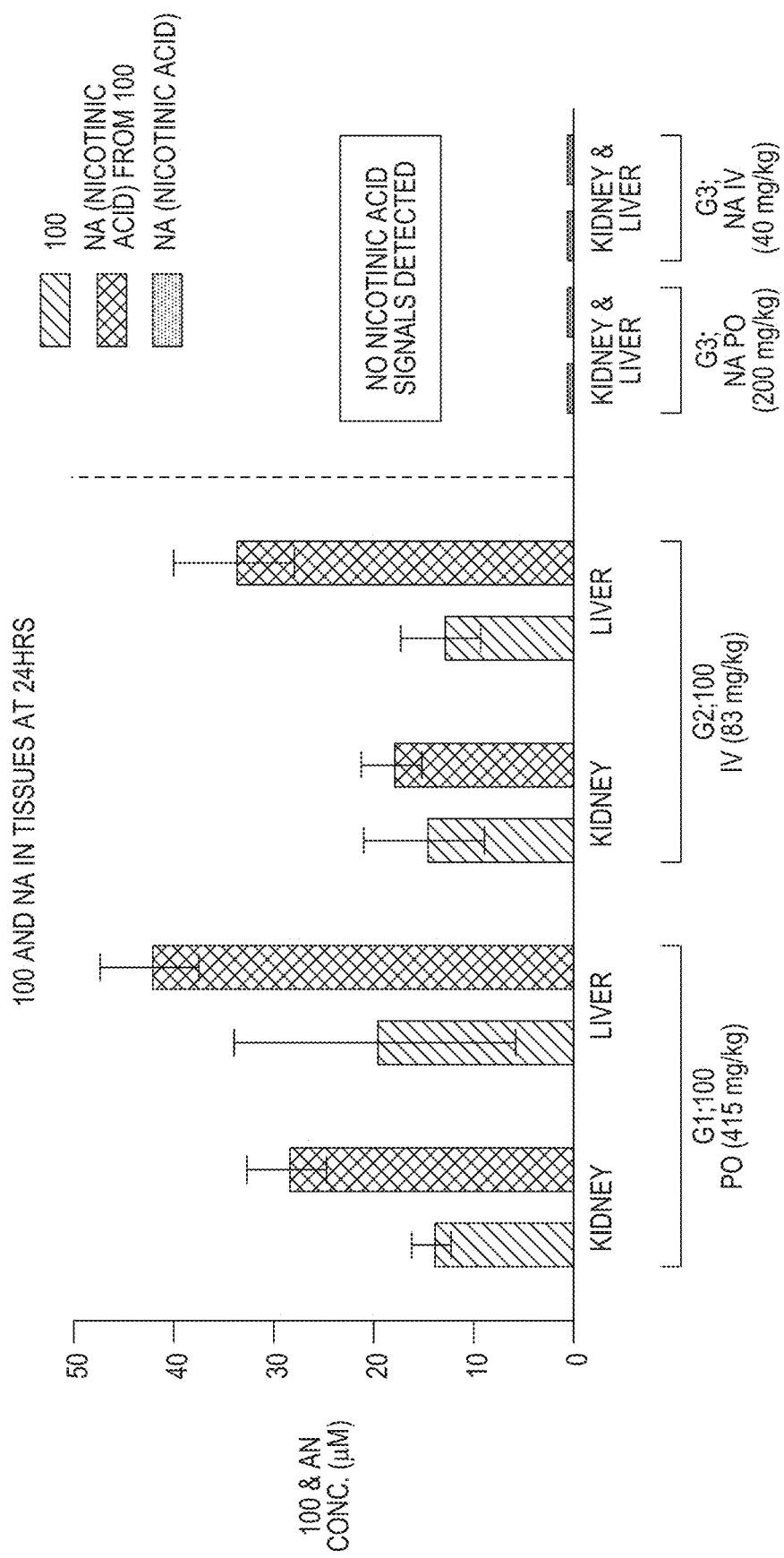
FIG. 12A illustrates the distribution of a Group 1 dose of compound 100 (415 mg/kg) distribution in kidney and liver tissue after 24 hrs.
FIG. 12B illustrates the distribution of a Group 2 dose of compound 100 (83 mg/kg) distribution in kidney and liver tissue after 24 hrs.
FIG. 12C illustrates the distribution of a Group 3 dose of nicotinic acid (200 mg/kg) and a Group 4 dose of nicotinic acid (40 mg/kg) distribution in kidney and liver tissue after 24 hrs.

No distribution phase following IV was seen when nicotinic acid was administered. Both compound 100 and nicotinic acid were detectable after 24 hrs following oral as well as IV administration of compound 100 in the liver and kidney tissues as illustrated in FIGS. 12A-C. Insignificant levels of nicotinic acid were detected in the nicotinic acid treated groups. Compound 100 delivers nicotinic acid into the tissues more efficiently than nicotinic acid as shown in FIGS. 12A-C. In conclusion, compound 100 shows superior in vivo pharmacology than nicotinic acid with a longer half-life, lower maximal concentration (C), better bioavailability and has a depot effect in the kidney and liver.

Example 21: Efficacy of Compound 100 in a Cisplatin Induced Kidney Injury Model in Mice The study was performed using protocols approved by the Institutional Animal Ethics Committee (IAEC) based on CPCSEA guidelines for animal care and use. BALB/c female mice of 6-8 weeks age were divided into 5 groups with each group containing 6 members. Animal room environment were monitored for temperature and relative humidity twice a day. The temperature range was 22° C.±3° C. and the humidity range was 30-70%, although the upper range for humidity may be exceeded during room cleaning. Animals were housed in IVC systems and provided with cycles of 12 hours of light and 12 hours of darkness through the study. SDS Feed (M/s. SDS diets services) and autoclaved drinking water was provided ad libitum.

The group parameters are provided in Table 20 below.

TABLE 20

| Group 1 | Group 2 | Group 3 | Group 4 | Group 4 |
|---|---|---|---|---|
| PBS PO bid (6 days) | PBS PO bid (6 days) + Cisplatin (25 mg/kg IP, single dose (Day 3)) | Compound 100 50 mg/kg PO bid (6 days) + Cisplatin (25 mg/kg IP, single dose (Day 3)) | Compound 100 250 mg/kg PO bid (6 days) + Cisplatin (25 mg/kg IP, single dose (Day 3)) | Compound 100 500 mg/kg PO bid (6 days) + Cisplatin (25 mg/kg IP, single dose (Day 3)) |

The vehicle for cisplatin was 0.9% saline while the vehicle for compound 100 was PBS at pH 6. The compound 100 formulations were prepared just prior to doing each time. The study was performed in 5 groups.

Animals were acclimatized prior to the study. Pretreatment with compound 100 was administered for 3 days before cisplatin dosing. Animals were weighed and administered vehicle in group 1 and cisplatin was administered at a single dose of 25 mg/kg to groups 2, 3, 4 and 5 intraperitonially on day-3 of the study. The oral dose groups (groups 3-5) were dosed with compound 100 twice daily for 6 days (3 days pre-dose and 3 days post-dose cisplatin).

Blood samples were collected at end of the study (12 h, post last dose terminal sampling, cardiac puncture) in 2 ml Eppendorf tubes, and serum was separated and stored at −20° C. for clinical chemistry analysis.

Figure 13:
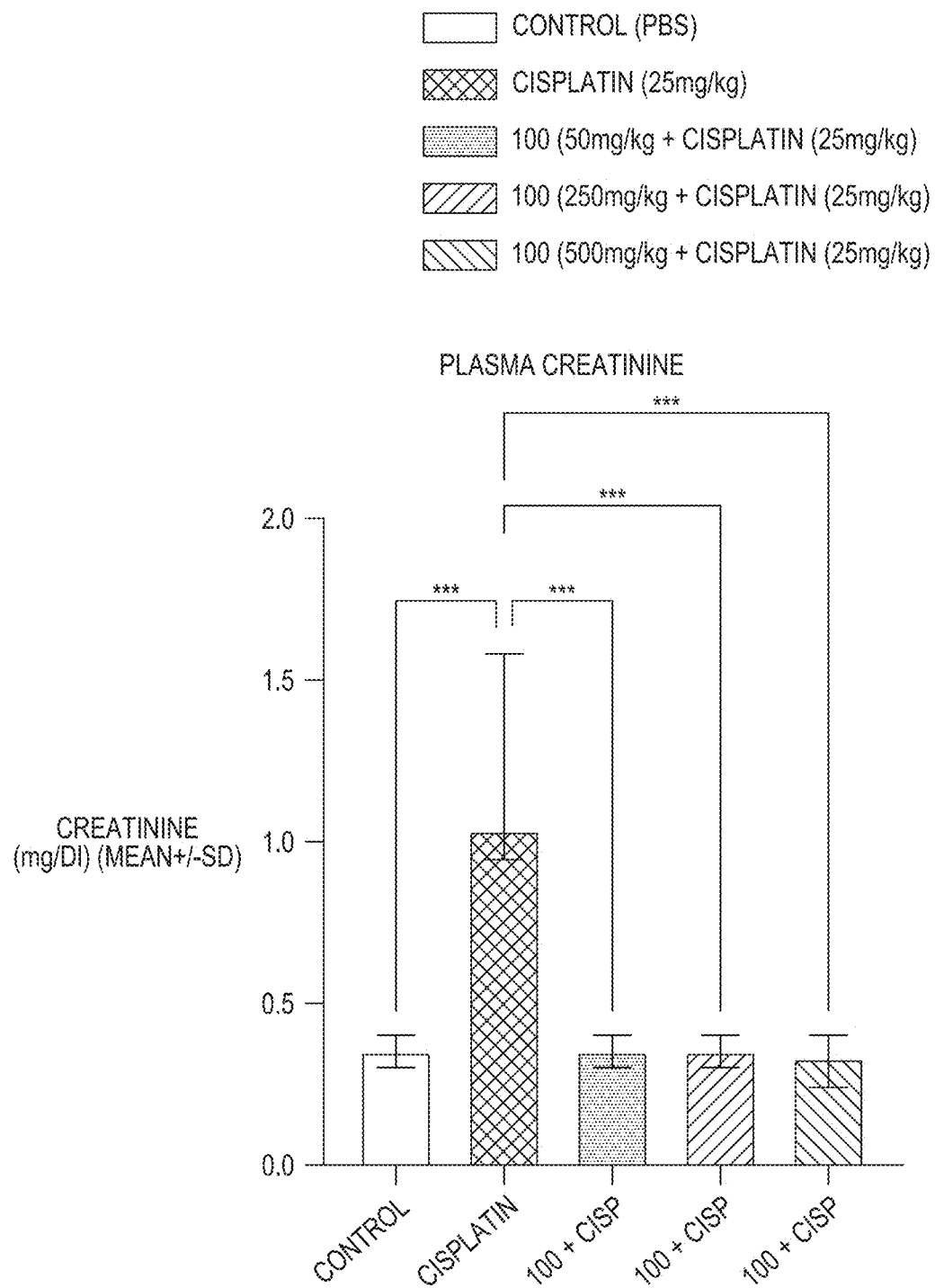
FIG. 13 illustrated the plasma creatine level of mice are dosed with a control, cisplatin (25 mg/kg), compound 100 (50 mg/kg) and cisplatin (25 mg/kg), compound 100 (250 mg/kg) and cisplatin (25 mg/kg) and compound 100 (500 mg/kg) and cisplatin (25 mg/kg).
Figure 14:
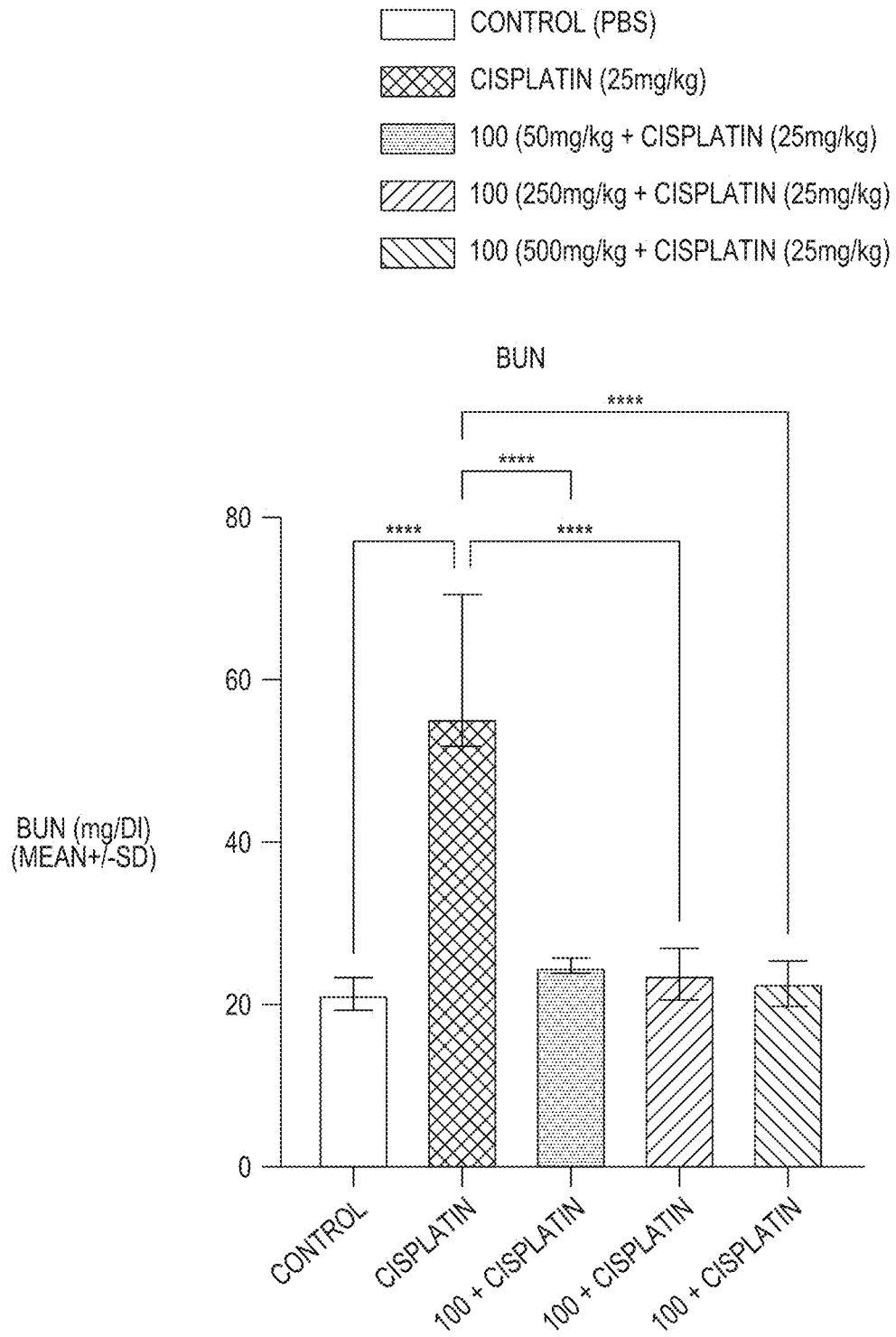
FIG. 14 illustrated the blood urea nitrogen (BUN) of mice are dosed with a control, cisplatin (25 mg/kg), compound 100 (50 mg/kg) and cisplatin (25 mg/kg), compound 100 (250 mg/kg) and cisplatin (25 mg/kg) and compound 100 (500 mg/kg) and cisplatin (25 mg/kg).

All animals survived and were sacrificed at end of the study (12 hours post last test compound dose) with an overdose of $CO_2$. Liver, kidneys & muscle (gastrocnemius and soleus/vastus lateralis) were collected, weighed and snap frozen in liquid nitrogen and stored at −80° C. for analysis. Serum creatinine and blood urea nitrogen (BUN) was determined using a clinical chemistry analyzer on the final day of blood collection and the results are graphically illustrated for groups 1-5 in FIG. 13 and FIG. 14, respectively.

Mice in group 2 were dull from day 5 to time of sacrifice. Body weight loss was observed in groups 2 and 5 with the group 2 showing the most weight loss. Mild to moderate kidney discoloration was observed in group 2. No observable abnormalities in kidneys were detected in the other groups.

Mice in group 2 showed significant increases in serum creatinine and BUN when compared to group 1 [$p<0.05$]. Treatment with compound 100 showed significant reduction in serum creatinine and BUN [$p<0.05$] at all three doses (i.e., groups 3-5), when compared to group 2, when administered orally twice daily for 6 days. No apparent differences in serum creatinine and BUN were observed between groups 3, 4 and 5. In conclusion, all three oral doses of compound 100, showed nephroprotection in a cisplatin induced acute kidney injury (AKI) mouse model.

Example 22: Long Term Solid Stability of Compound 100

Compound 100 was kept in a well-sealed glass vial at −15° C. in order to assess solid state stability at in a deep freezer. The compound from this vial was assessed for purity by UPLC at two different timepoints: Day 0 and Day 93 (3 months). Table 21 depicts the results obtained for solid state stability based on the purity measurements were made at day 0.

TABLE 21

100: Solid State Stability @ −15° C. (freezer

| Sl. No. | Day | Date | Purity % by UP LC |
|---|---|---|---|
| 1 | 0 | 19 Oct. 2022 | 98.92 |
| 2 | 93 | 20 Jan. 2023 | 99.62 |

Compound 100 is stable in its solid state when stored at −15° C. for up to three months.

What is claimed is:

1. A compound having the structure:

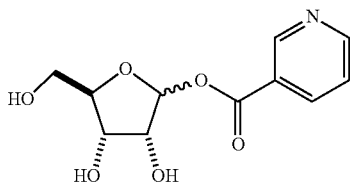 [SMILES: O=C(OC1O[C@H](CO)[C@@H](O)[C@H]1O)c1cccnc1]

or pharmaceutically acceptable salts, hydrates or solvates thereof.

2. A pharmaceutical composition comprising the compound of claim 1 and a pharmaceutically acceptable excipient.

3. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the compound of claim 1.

4. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the pharmaceutical composition of claim 2.

5. A compound having the structure:

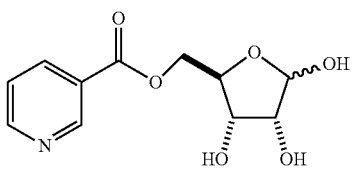 [SMILES: O=C(OC[C@H]1OC(O)[C@H](O)[C@@H]1O)c1cccnc1]

or pharmaceutically acceptable salts, hydrates or solvates thereof.

6. A pharmaceutical composition comprising the compound of claim 5 and a pharmaceutically acceptable excipient.

7. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the compound of claim 5.

8. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the pharmaceutical composition of claim 6.

9. A compound having the structure:

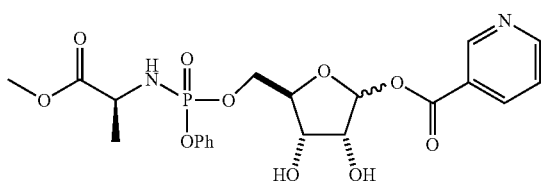 [SMILES: COC(=O)[C@H](C)NP(=O)(OC[C@H]1OC(OC(=O)c2cccnc2)[C@H](O)[C@@H]1O)Oc1ccccc1]

or pharmaceutically acceptable salts, hydrates or solvates thereof.

10. A pharmaceutical composition comprising the compound of claim 9 and a pharmaceutically acceptable excipient.

11. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the compound of claim 9.

12. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the pharmaceutical composition of claim 10.

13. A compound having the structure:

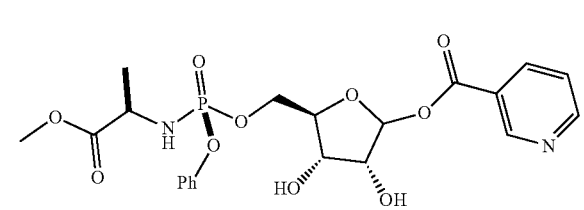 [SMILES: COC(=O)[C@@H](C)N[P@](=O)(OC[C@H]1OC(OC(=O)c2cccnc2)[C@H](O)[C@@H]1O)Oc1ccccc1]

or pharmaceutically acceptable salts, hydrates or solvates thereof.

14. A pharmaceutical composition comprising the compound of claim 13 and a pharmaceutically acceptable excipient.

15. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the compound of claim 13.

16. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the pharmaceutical composition of claim 14.

17. A compound having the structure:

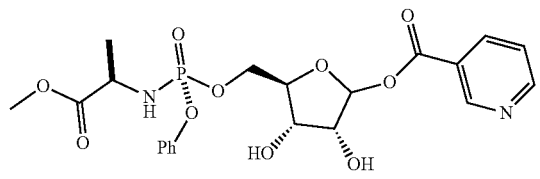 [SMILES: COC(=O)[C@@H](C)N[P@@](=O)(OC[C@H]1OC(OC(=O)c2cccnc2)[C@H](O)[C@@H]1O)Oc1ccccc1]

or pharmaceutically acceptable salts, hydrates or solvates thereof.

18. A pharmaceutical composition comprising the compound of claim 17 and a pharmaceutically acceptable excipient.

19. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the compound of claim 17.

20. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the pharmaceutical composition of claim 18.

21. A compound having the structure:

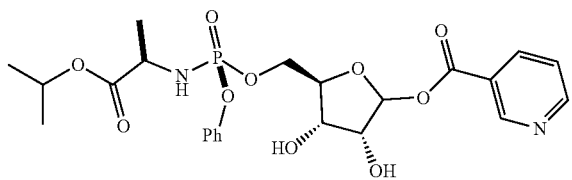 [SMILES: CC(C)OC(=O)[C@@H](C)N[P@](=O)(OC[C@H]1OC(OC(=O)c2cccnc2)[C@H](O)[C@@H]1O)Oc1ccccc1]

or pharmaceutically acceptable salts, hydrates or solvates thereof.

22. A pharmaceutical composition comprising the compound of claim 21 and a pharmaceutically acceptable excipient.

23. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the compound of claim 21.

24. A method of treating a metabolic disorder, a cardiovascular disorder, a cerebrovascular disorder, a liver disorder, a kidney disorder or a muscle disorder in a subject in need thereof comprising administering to the subject a therapeutically effective amount of the pharmaceutical composition of claim 22.

* * * * *